(12) United States Patent
Edge et al.

(10) Patent No.: US 12,161,647 B2
(45) Date of Patent: *Dec. 10, 2024

(54) TREATING HEARING LOSS

(71) Applicant: Massachusetts Eye and Ear Infirmary, Boston, MA (US)

(72) Inventors: Albert Edge, Brookline, MA (US); Hideyuki Okano, Tokyo (JP); Masato Fujioka, Tokyo (JP); Kunio Mizutari, Tokyo (JP)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/118,111

(22) Filed: Dec. 10, 2020

(65) Prior Publication Data
US 2021/0299138 A1    Sep. 30, 2021

Related U.S. Application Data

(63) Continuation of application No. 16/007,586, filed on Jun. 13, 2018, now Pat. No. 10,898,492, which is a continuation of application No. 14/426,629, filed as application No. PCT/US2013/058446 on Sep. 6, 2013, now abandoned.

(60) Provisional application No. 61/698,475, filed on Sep. 7, 2012.

(51) Int. Cl.
   *A61K 31/55* (2006.01)
   *A61K 9/00* (2006.01)
   *A61K 47/10* (2017.01)
   *A61K 47/34* (2017.01)

(52) U.S. Cl.
CPC ............ *A61K 31/55* (2013.01); *A61K 9/0046* (2013.01); *A61K 47/10* (2013.01); *A61K 47/34* (2013.01)

(58) Field of Classification Search
CPC ........ A61K 31/55; A61K 47/10; A61K 47/34; A61K 9/0046; A61P 27/16
See application file for complete search history.

(56) References Cited

U.S. PATENT DOCUMENTS

| | | |
|---|---|---|
| 4,522,811 A | 6/1985 | Eppstein et al. |
| D309,535 S | 7/1990 | Wilson |
| D360,535 S | 7/1995 | Sjoberg |
| D447,031 S | 8/2001 | Oh |
| 6,417,185 B1 | 7/2002 | Goff et al. |
| 6,489,344 B1 | 12/2002 | Nuss et al. |
| 6,608,063 B2 | 8/2003 | Nuss et al. |
| 6,756,511 B2 | 6/2004 | Castro Pineiro et al. |
| 6,890,956 B2 | 5/2005 | Churcher et al. |
| 6,984,626 B2 | 1/2006 | Nadin et al. |
| 7,049,296 B2 | 5/2006 | Castro Pineiro et al. |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Castro Pineiro et al. |
| 7,206,639 B2 | 4/2007 | Jacobsen et al. |
| 7,399,633 B2 | 7/2008 | Bernstein et al. |
| D646,625 S | 10/2011 | Youn |
| 8,188,069 B2 | 5/2012 | Miller et al. |
| 8,518,944 B2 | 8/2013 | Subramanyam et al. |
| 8,617,810 B2 | 12/2013 | Heller et al. |
| 8,673,634 B2 | 3/2014 | Li et al. |
| 10,406,163 B2 | 9/2019 | Edge et al. |
| 10,603,295 B2 | 3/2020 | Edge et al. |
| 10,898,492 B2 * | 1/2021 | Edge ................. A61K 9/0046 |
| 10,925,872 B2 | 2/2021 | Lorrain et al. |
| 2004/0029862 A1 | 2/2004 | Belanger et al. |
| 2004/0049038 A1 | 3/2004 | Collins et al. |
| 2004/0186147 A1 | 9/2004 | Hannam et al. |
| 2005/0019801 A1 | 1/2005 | Rubin et al. |
| 2005/0119293 A1 | 6/2005 | Collins et al. |
| 2005/0143369 A1 | 6/2005 | Castro Pineiro et al. |
| 2005/0182109 A1 | 8/2005 | Collins et al. |
| 2005/0182111 A1 | 8/2005 | Pineiro et al. |
| 2005/0215602 A1 | 9/2005 | Campbell et al. |
| 2005/0287127 A1 | 12/2005 | Li et al. |
| 2006/0030837 A1 | 2/2006 | McKenna et al. |
| 2007/0093878 A1 | 4/2007 | Edge et al. |
| 2008/0146617 A1 | 6/2008 | Aud et al. |
| 2008/0267929 A1 | 10/2008 | Li et al. |
| 2009/0098093 A1 | 4/2009 | Edge |
| 2009/0099237 A1 | 4/2009 | Aud et al. |
| 2009/0124568 A1 * | 5/2009 | Heller ................... A61P 27/16 435/6.12 |
| 2009/0232780 A1 | 9/2009 | Edge et al. |
| 2009/0297533 A1 * | 12/2009 | Lichter ............... C07K 16/241 424/142.1 |

(Continued)

FOREIGN PATENT DOCUMENTS

| | | |
|---|---|---|
| CN | 1441841 | 9/2003 |
| GB | 2459910 | 11/2009 |

(Continued)

OTHER PUBLICATIONS

Kehrle (Arch Otolaryngol Head Neck Surg., 2008; 134(6):647-651).*
Extended European Search Report in European Appln No. 21181586.5, dated Nov. 26, 2021, 8 pages.
Extended European Search Report in European Appln No. 21190313.3, dated Feb. 16, 2022, 11 pages.
JP Office Action in Japanese Appln. No. 2018-540010, dated Sep. 21, 2021, 5 pages (with English translation).
Office Action in Canadian Appln. No. 2,883,896, dated Dec. 13, 2021, 4 pages.
Office Action in Chinese Appln. No. 201780017058.9, dated Nov. 15, 2021, 23 pages (with English translation).
Office Action in Japanese Appln. No. 2020-180340, dated Dec. 21, 2021, 10 pages (with English Translation).

(Continued)

*Primary Examiner* — Pancham Bakshi
(74) *Attorney, Agent, or Firm* — Fish & Richardson P.C.

(57) ABSTRACT

This invention relates to methods for treating hearing loss associated with loss of cochlear hair cells, e.g., caused by noise exposure, using certain gamma secretase inhibitors, in post-neonatal animals, e.g., adolescents and adults.

20 Claims, 11 Drawing Sheets

Specification includes a Sequence Listing.

(56) References Cited

U.S. PATENT DOCUMENTS

| | | |
|---|---|---|
| 2009/0306225 A1 | 12/2009 | Lichter et al. |
| 2010/0273864 A1 | 10/2010 | Lichter et al. |
| 2011/0020232 A1 | 1/2011 | Eberhart et al. |
| 2011/0033480 A1 | 2/2011 | Sarkar et al. |
| 2011/0305674 A1 | 12/2011 | Edge et al. |
| 2011/0319377 A1 | 12/2011 | Lichter et al. |
| 2013/0085112 A1 | 4/2013 | Collard et al. |
| 2013/0210145 A1 | 8/2013 | Edge |
| 2013/0225543 A1 | 8/2013 | Jones et al. |
| 2014/0044763 A1 | 2/2014 | Kustov et al. |
| 2015/0030568 A1 | 1/2015 | Li et al. |
| 2015/0209406 A1 | 7/2015 | Chen |
| 2017/0349884 A1 | 12/2017 | Karp et al. |
| 2018/0148456 A1 | 5/2018 | Clay et al. |
| 2019/0010449 A1 | 1/2019 | Edge et al. |
| 2019/0203210 A1 | 7/2019 | Edge et al. |
| 2019/0247381 A1 | 8/2019 | Edge et al. |
| 2020/0255800 A1 | 8/2020 | Edge |
| 2021/0290686 A1 | 9/2021 | Edge et al. |
| 2022/0008433 A1 | 1/2022 | Edge et al. |

FOREIGN PATENT DOCUMENTS

| | | |
|---|---|---|
| JP | 2006-117536 | 5/2006 |
| JP | 2006/520386 | 9/2006 |
| JP | 2007/503816 | 3/2007 |
| JP | 2007/526248 | 9/2007 |
| JP | 2011-518195 | 6/2011 |
| JP | 2012-509899 | 4/2012 |
| WO | WO 1998/028268 | 7/1998 |
| WO | WO 2000/053632 | 9/2000 |
| WO | WO 2000/059939 | 10/2000 |
| WO | WO 2001/070677 | 9/2001 |
| WO | WO 2002/049038 | 6/2002 |
| WO | WO 2003/093251 | 11/2003 |
| WO | WO 2003/093252 | 11/2003 |
| WO | WO 2003/093253 | 11/2003 |
| WO | WO 2003/093264 | 11/2003 |
| WO | WO 2004/039370 | 5/2004 |
| WO | WO 2004/039800 | 5/2004 |
| WO | WO 2005/014553 | 2/2005 |
| WO | WO 2005/030731 | 4/2005 |
| WO | WO 2006/026570 | 3/2006 |
| WO | WO 2007/075911 | 7/2007 |
| WO | WO 2008/076556 | 6/2008 |
| WO | WO 2009/087130 | 7/2009 |
| WO | WO 2009/132050 | 10/2009 |
| WO | WO 2010/060088 | 5/2010 |
| WO | WO 2012/005805 | 1/2012 |
| WO | WO 2014/145205 | 9/2014 |
| WO | WO 2014/159356 | 10/2014 |
| WO | WO 2015/168149 | 11/2015 |
| WO | WO 2016/022776 | 2/2016 |
| WO | WO 2018/111926 | 6/2018 |

OTHER PUBLICATIONS

Wislet-Gendebien et al., "Plasticity of cultured mesenchymal stem cells: switch from nestin-positive to excitable neuron-like phenotype," Stem Cells, 2005, 23:392-402.

Feng et al., "Blocking caspase-3-dependent pathway preserves hair cells from salicylate-induced apoptosis in the guinea pig cochlea," Mol Cell Biochem., 2011, 353:291-303.

JP Office Action in Japanese Appln. No. 2020-180340, dated Jul. 6, 2021, 10 pages (with English translation).

Li et al., "Round Window Membrane Delivery of L-Methionine Provides Protection from Cisplatin Ototoxicity Without Compromising Chemotherapeutic Efficacy," NeuroToxicology, 2001, 22:163-176.

Xia et al., "Ototoxicity of cisplatin administered to guinea pigs via the round window membrane," J Toxicol Sci., 2012, 37(4):823-830.

Yang et al., "EGb 761 (Ginkgo biloba) protects cochlear hair cells against ototoxicity induced by gentamicin via reducing reactive oxygen species and nitric oxide-related apoptosis," J Nutr Biochem., 2011, 22:886-894.

CA Office Action in Canadian Appln. No. 2,883,896, dated Apr. 1, 2021, 4 pages.

Abbott et al., "Coordinated regulation of Toll-like receptor and NOD2 signaling by K63-linked polyubiquitin chains," Molecular and Cellular Biology, 2007, 27:6012-6025.

Adam et al., "Cell fate choices and the expression of Notch, Delta and Serrate homologues in the chick inner ear: parallels with *Drosophila* sense-organ development," Development, 125(23):4645-54 (Dec. 1998).

Adhikary et al., The ubiquitin ligase HectH9 regulates transcriptional activation by Myc and is essential for tumor cell proliferation, Cell, 2005, 123 :409-421.

Adler and Raphael "New hair cells arise from supporting cell conversion in the acoustically damaged chick inner ear," Neuroscience Letters, Feb. 1996, 205: 17-20.

Aletsee et al., "The disintegrin Kistrin inhibits neurite extension from spiral ganglion explants cultured on laminin," Audiol. Neurootol., 6:57-65 (2001).

Artavanis-Tsakonas et al., "Notch Signaling," Sci., 268: 225-232 (1995).

Barker et al., "Identification of stem cells in small intestine and colon by marker gene Lgf5," Nature, 2007, 449: 1003-1007.

Barker, "Wnt Signaling: vol. 1: Pathway Methods and Mammalian Models," in Methods in Molecular Biology, Nov. 2008, 5-15.

Bartolami et al., "Appearance and Distribution of the 275 kD Hair-Cell Antigen During Development of the Avian Inner Ear," J. Comp. Neurol., 314:777-788 (1991).

Basi et al., "Amyloid precursor protein selective gamma-secretase inhibitors for treatment Amyloid precursor protein selective gamma-secretase of Alzheimer's disease," Alzheimer's Research & Therapy, 2:36 (2010) pp. 1-21.

Batts et al., "Notch signaling and Hes labeling in the normal and drug-damaged organ of Corti," Hear Res., 249:15-22 (Mar. 2009).

Becvarovski et al., "Round Window Gentamicin Absorption: An In Vivo Human Model," Laryngoscope, Sep. 2002, 112: 1610-1613.

Ben-Arie et al., "Math1 is essential for genesis of cerebellar granule neurons." Nature, 19987, 390: 169-172.

Ben-Arie et al., "Functional conservation of atonal and Math1 in the CNS and PNS," Development, 2000, 127:1039-1048.

Bermingham et al., "Math1: An Essential Gene for the Generation of Inner Ear Hair Cells," Science, 1999, 284: 1837-1841.

Bertrand et al., "Proneural genes and the specification of neural cell types," Nature Reviews Neuroscience, 2002, 3:517-530.

Beurel et al., "Glycogen synthase kinase-3 (GSIG): Regulation, actions, and diseases," Pharmacology & Therapeutics, 2015, 148:114-131.

Bodson et al., "Hair cell progenitors: identification and regulatory genes," Acta Otolaryngol, Mar. 2010, 130(3):312-7.

Bossuyt et al., "Atonal homolog 1 is a tumor suppressor gene," PLoS Biology, 2009, 7:e39.

Bouchard et al., "Pax2 and homeodomain proteins cooperatively regulate a 435 bp enhancer of the mouse Pax5 gene at the midbrain-hindbrain boundary," Develop., 127:1017-28 (2000).

Bramhall, "Lgr5-Positive Supporting Cells Generate New Hair Cells in the Postnatal Cochlea," Stem Cell Reports, Mar. 2014, 2:1-12.

Breuskin et al., "Strategies to regenerate hair cells: identification of progenitors and critical genes," Hear Res, 2008, 236(1-2):1-10.

Brooker et al., "Notch ligands with contrasting functions: Jagged1 and Delta1 in the mouse inner ear," Development, 2006, 133:1277-1286.

Brors et al., "EphA4 Provides Repulsive Signals to Developing Cochlear Ganglion Neurites Mediated through Ephrin-B2 and -B3," J. Comp. Neurol., 462:90-100 (2003).

Bryant et al., "Sensory organ development in the inner ear: Molecular and cellular mechanisms," British Medical Bulletin, 63:39-57 (2002).

Burns and Stone, "Development and regeneration of vestibular hair cells in mammals," Semin Cell Dev Biol, 2017, 65: 96-105.

(56) References Cited

OTHER PUBLICATIONS

Burns et al., "MYC Gene Delivery to Adult Mouse Utricles Stimulates Proliferation of Postmitotic Supporting Cells In Vitro," Plos One, Oct. 2012, 7: 248704.

Burton et al., "The role of Pax2 in mouse inner ear development," Dev. Biol., 272:161-175 (2004).

Cafaro et al., "Atoh1 expression defines activated progenitors and differentiating hair cells during avian hair cell regeneration," Developmental dynamics, 2007, 236:156-170.

Cai et al., "Conditional deletion of Atoh1 reveals distinct critical periods for survival and function of hair cells in the organ of Corti," The Journal of Neuroscience, 2013, 10110-10122.

Caiazzo et al., "Direct generation of functional dopaminergic neurons from mouse and human fibroblasts," Nature, 476:224-7 (Jul. 2011).

Cau et al., "Mash1 activates a cascade of bHLH regulators in olfactory neuron progenitors," Develop., 124:1611-1621 (1997).

Chai et al., "Wnt signaling induces proliferation of sensory precursors in the postnatal mouse cochlea," PNAS, 2012, 109: 8167-8172.

Charron et al., "The Morphogen Sonic Hedgehog is an Axonal Chemoattractant that Collaborates with Netrin-1 in Midline Axon Guidance," Cell., 113:11-23 (2003).

Chen et al., "ARF-BPI/Mule is a critical mediator of the ARF tumor suppressor," Cell, 2005. 121: 1071-1083.

Chen et al., "The role of Math1 in inner ear development: Uncoupling the establishment of the sensory primordium from hair cell fate determination," Develop., 129:2495-2505 (2002).

Cheng et al., "Destabilization of Atoh1 by E3 Ubiquitin Ligase Huwe1 and Casein Kinase Is Essential for Normal Sensory Hair Cell Development," Journal of Biological Chemistry, Sep. 2016, 291(40):21096-21109.

Cheng, "Role of the Ubiquitin-Proteasome Pathway in the Inner Ear: Identification of an E3 Ubiquitin Ligase for Atoh1," Thesis for the Degree of Doctor of Philosophy in Health Sciences and Technology, Harvard-Massachusetts Institute of Technology, Aug. 29, 2014, 1-99.

Chim et al., "Deafness associated with the use of Bortezomib in multiple myeloma," Acta Oncologica, Jan. 2008, 47(2):323-324.

Clevers, "Wnt/beta-catenin signaling in development and disease," Cell, 2006, 127:469-480.

Colter et al., "Rapid expansion of recycling stem cells in cultures of plastic-adherent cells from human bone marrow," Proc. Natl. Acad. Sci. U.S.A , 97:3213-3218 (2000).

Corrales et al., "Engraftment and Differentiation of Embryonic Stem Cell-Derived Neural Progenitor Cells in the Cochlear Nerve Trunk: Growth of Processes into the Organ of Corti," J. Neurobiol., 66:1489-500 (2006).

Corwin et al., "Regeneration of Sensory Hair Cells After Acoustic Trauma," Science, Jun. 1988, 240:1772-1774.

Cosgrove et al., Am. J. Pathol., 157:1649-59 (2000).

Cox et al., "Spontaneous hair cell regeneration in the neonatal mouse cochlea in vivo," Development, 2014, 141: 816-829.

Crowder and Freeman, "Glycogen Synthase Kinase-3b Activity Is Critical for Neuronal Death Caused by Inhibiting Phosphatidylinositol 3-Kinase or Akt but Not for Death Caused by Nerve Growth Factor Withdrawal," The Journal of Biological Chemistry, Nov. 2000, 275: 34266-34271.

Dabdoub et al., "Abstract # 443: WNt/B-Catenin Signaling in the Developing Mammalian Cochlea," ARO 31st Annual Midwinter Meeting, Phoenix, Arizona, Feb. 16-21, 2008, 3 pages.

Dabdoub et al., "Abstract # 8: Wnt Signaling in the Developing Mammalian Cochlea," ARO 30th Annual Midwinter Meeting, Denver, Colorado, Feb. 10-15, 2007, 2 pages.

D'Arca et al., "Huwe 1 ubiquitin ligase is essential to synchronize neuronal and glial differentiation in the developing cerebellum," PNAS, 2010, 107:5875-5880.

Daudet and Lewis, "Two contrasting roles for Notch activity in chick inner ear development: specification of pro sensory patches and lateral inhibition of hair-cell differentiation," Development, 132:541-51 (Feb. 2005).

Daudet et al., "Notch regulation of progenitor cell behavior in quiescent and regenerating auditory epithelium of mature birds," Dev Biol., 326(1):86-100 (Feb. 1, 2009).

Davis, "Hearing disorders in the population: first phase findings of the MRC National Study of Hearing," Hearing Science and Hearing Disorders, 1983, 35-60.

De Groot et al., "Huwel-mediated ubiquitylation of dishevelled defines a negative feedback loop in the Wnt signaling pathway," Science Signaling, Mar. 2014, 7:ra26.

Declaration of Non-Establishment of International Search Report for PCT/US2009/065747, mailed Apr. 8, 2010.

Deshaies and Joazeiro, "RING domain E3 ubiquitin ligases," Annual Review of Biochemistry, 2009, 78:399-434.

Dezawa et al., "Specific induction of neuronal cells from bone marrow stromal cells and application for autologous transplantation," J. Clin. Invest., 113:1701-1710 (2004).

Doetzlhofer et al., "Hey2 regulation by FGF provides a Notch-independent mechanism for maintaining pillar cell fate in the organ of Corti," Dev Cell, 16:58-69 (Jan. 2009).

Dong et al., "Calpain inhibitor MDL28170 modulates Aβ formation by inhibiting the formation of intermediate $A\alpha_{46}$ and protecting Aβ from degradation," The FASEB Journal, Dec. 2005, 21 pages.

D'Onofrio et al., "Advances in the identification of γ-secretase inhibitors for the treatment of Alzheimer's disease," Expert Opinion on Drug Discovery, Jan. 1, 2012, 7(1):19-37.

Doyonnas et al., "Hematopoietic contribution to skeletal muscle regeneration by myelomoncytic precursors," Proc. Natl. Acad. Sci. U.S.A, 101:13507-13512 (2004).

Eatock and Rusch, "Developmental changes in the physiology of hair cells," Cell & Developmental Biology, 1997, 8:265-275.

Edge and Chen, "Hair cell regeneration," Curr. Opin. Neurobiol, 2008, 18: 377-382.

Edge et al., "Current Applications of Cellular Xenografts," Trans. Proc., 32:1169-1171 (2000).

Eng et al., "An approach to correlate tandem mass spectral data of peptides with amino acid sequences in a protein database," Journal of the American Society for Mass Spectrometry, 1994, 5:976-989.

EP Brief Communication in European Appln. No. 13836099.5, dated Jan. 19, 2021, 9 pages.

EP Office Action in European Appl. No. 17744987, dated May 14, 2020, 3 pages.

European Search Report in Application No. 13836099, dated Mar. 8, 2016, 9 Pages.

Examination Report issued in Australian Patent Application No. 2007334260 on Aug. 23, 2012 (5 pages).

Extended European Search Report issued in corresponding European Patent Application No. 07871464.9, mailed Nov. 17, 2010.

Extended European Search Report issued in EP 0982830, mailed Dec. 7, 2012.

Flora et al., "Deletion of Atoh1 disrupts Sonic Hedgehog signaling in the developing cerebellum and prevents medulloblastoma," Science, 2009, 326:1424-1427.

Flora et al., "The E-protein Tcf4 interacts with Math 1 to regulate differentiation of a specific subset of neuronal progenitors," PNAS, 2007, 104: 15382-15387.

Forge et al., "Hair Cell Recovery in the Vestibular Sensory Epithelia of Mature Guinea Pigs," The Journal of Comparative Neurology, 1998, 397: 69-88.

Forge et al., "Ultrastructural evidence for hair cell regeneration in the mammalian inner ear," Science, 1993, 259: 1616-1619.

Forget et al., "Shh Signaling Protects Atoh1 from Degradation Mediated by the E3 Ubiquitin Ligase Huwel in Neural Precursors," Developmental Cell, Jun. 2014, 29: 649-661.

Frisina, "Age-related hearing loss: ear and brain mechanisms," Annals of the New York Academy of Sciences, 2009, 1170: 708-717.

Fritzsch et al., "Atoh1 Null Mice Show Directed Afferent Fiber Growth to Undifferentiated Ear Sensory Epithelia Followed by Incomplete Fiber Retention," Dev. Dyn., 233:570-583 (2005).

Fritzsch et al., "Lack of Neurotrophin 3 Causes Losses of Both Classes of Spiral Ganglion Neurons in the Cochlea in a Region-Specific Fashion," J. Neurosci., 17:6213-6225 (1997).

(56) References Cited

OTHER PUBLICATIONS

Fritzsch, "Development of inner ear afferent connections: forming primaly neurons and connecting them to the developing sensory epithelia," Brain Research Bulletin, 2003, 60:423-433.
Fujioka et al., "SY3A-H5 A novel y-secretase inhibitor, LY411575, replaced auditory hair cells and recovered hearing loss after severe acoustic trauma in mice," Neurosci Res., 2008, 61(Suppl):S25.
Fujioka et al., "In vivo differentiation toward hair cell: A novel gamma-secretase inhibitor, LY411575, replaced auditory hair cells and ameliorated hearing impairment after severe acoustic trauma in mice," Presented at the 31st Annual Meeting of the Japan Neuroscience Society Symposium "Regeneration of Sensory Cells in the Inner Ear—From Bench to Bedside," Jul. 7, 2008, 30 pages.
Fujioka et al., "Manipulating cell fate in the cochlea: a feasible therapy for hearing loss," Trends Neurosci, 2015, 38: 139-144.
Gage, "Cell therapy," Nature, 392(6679 Suppl):18-24 (1998).
Gao et al., "mTOR drives its own activation via SCF(~TrCP)dependent degradation of the mTOR inhibitor DEPTOR," Molecular Cell, 2011, 44:290-303.
Gao et al., "Quantitative imaging of cochlear soft tissues in wildtype and hearingimpaired transgenic mice by spectral domain optical coherence tomography," Optics Express, 2011, 19:15415-15428.
Garapaty-Rao et al., "Identification of EZH2 and EZH1 Small Molecule Inhibitors with Selective Impact on Diffuse Large B Cell Lymphoma Cell Growth," Chem. Biol, 2013, 20(11):1329-1339.
Geling et al., "A γ-secretase inhibitor blocks Notch signaling in vivo and causes a severe neurogenic phenotype in zebrafish," EMBO report, 2002, 688-694.
Gillespie et al., "LIF is more potent than BDNF in promoting neurite outgrowth of mammalian auditory neurons in vitro," Neuro. Rep., 12:275-279 (2001).
Golub et al., "Hair Cell Replacement in Adult Mouse Utricles after Targeted Ablation of Hair Cells with Diphtheria Toxin," The Journal of Neuroscience, Oct. 2012, 32: 15093-15105.
Gowan et al., "Crossinhibitory Activities of Ngn1 and Math1 Allow Specification of Distinct Dorsal Interneurons," Neuron., 31:219-232 (2001).
Goycoolea and Lundman, "Round window membrane. Structure function and permeability: a review," Microsc Res Tech., 36:201-11 (Feb. 1, 1997).
Gregorieff and Clevers, "Wnt signaling in the intestinal epithelium: from endoderm to cancer," Genes & Development, 2005, 19:877-890.
Gubbels et al., "Functional auditory hair cells produced in the mammalian cochlea by in utero gene transfer," Nature, 2008, 455:537-541.
Guo et al., "Targeting the Notch signaling pathway in cancer therapeutics," Thoracic Cancer, 2014, 5: 473-486.
Haapasalo and Kovacs; "The Many Substrates of Presenilin/γ-Secretase" Journal Alzheimers Disease. 2011: 25(1): 3-28.
Hadland et al., "γ-secretase inhibitors repress thymocyte development," Proc Natl. Acad Sci USA, 98:7487-91 (Jun. 19, 2001).
Han and Shen, "Targeting γ-secretase in breast cancer," Breast Cancer: Targets and Therapy, 2012, 2012: 83-90.
Hartman et al., "Hes5 expression in the postnatal and adult mouse inner ear and the drug-damaged cochlea," J Assoc Res Otolaryngol., 10:321-40 (Sep. 2009).
Hawkins et al., "The developmental genetics of auditory hair cells," Hum. Mol. Genet., 13:R289-296 (2004).
Heller et al., "Parvalbumin 3 is an Abundant $Ca^{2+}$ Buffer in Hair Cells," J. Assoc. Res. Otolaryngol., 3:488-498 (2002).
Helms et al., "Autoregulation and multiple enhancers control Math1 expression in the developing nervous system," Develop., 127:1185-1196 (2000).
Helms et al., "Overexpression of MATH1 Disrupts the Coordination of Neural Differentiation in Cerebellum Development," Mol. Cell. Neurosci., 17:671-682 (2001).

Hermann et al., "Efficient generation of neural stem cell-like cells from adult human bone marrow stromal cells," J. Cell. Sci., 117:4411-4422 (2004).
Herold et al., "Mizl and HectH9 regulate the stability of the checkpoint protein, TopBP1," The EMBO Journal, 2008, 27:2851-2861.
Herzog et al., "Plasticity of marrow-derived stem cells," Blood, 102:3483-3493 (2003).
Hess et al., "Bone marrow-derived stem cells initiate pancreatic regeneration," Nat. Biotechnol., 21:763-770 (2003).
Hirabayashi et al., "The Wnt/beta-catenin pathway directs neuronal differentiation of cortical neural precursor cells," Development, 2004, 131: 2791-2801.
Hosoya et al., "Method for efficient screening of substances inducing differentiation into inner ear hair cells with the use of spheres derived from inner ear cells," Otol Jpn, 2008, 18(4): 275 (with Englsih translation).
Hosoya et al., "An efficient screening method using inner-ear derived spheres for selection of compounds that induce hair cell differentiation," Neurosci. Res., 2008, 61S:S57 Abstract, 2 pages.
Hu and Ulfendahl, "Cell replacement therapy in the inner ear," Stem Cell and Development, 15:449- 459 (2006).
Hu et al., "Neural cograft stimulates the survival and differentiation of embryonic stem cells in the adult mammalian auditory System,". Brain Research, 2005, 1051:137-144.
Hu et al., "Survival and neural differentiation of adult neural stem cells transplanted into the mature inner ear," Exper. Cell. Res., 302:40-47 (2005).
Huang et al., "Lysine 63-linked polyubiquitination is required for EGF receptor degradation," PNAS, Sep. 2013, 110(39):15722-15727.
Huang, "Age-related hearing loss," Minn Med, 2007, 90(10):48-50.
Huibregtse et al., A family of proteins structurally and functionally related to the E6-AP ubiquitin-protein ligase, PNAS, 19995, 92:5249.
Hume et al., "Expression of LHX3 and SOX2 during mouse inner ear development," Gene Expression Patterns, 2007, 7:798-807.
Husseman and Raphael, Gene therapy in the inner ear using adenovirus vectors. Advances in Oto-Rhino-Laryngology, 2009, 66:37-51.
Huynh et al., "The novel gamma secretase inhibitor RO4929097 reduces the tumor initiating potential of melanoma," PLoS One, 6(9):e25264, (2011) 10 pages.
Hyde et al., "Studies to investigate the in vivo therapeutic window of the γ-secretase inhibitor $N^2$-[(2S)-2-(3,5-difluorophenyl)-2-hydroxyethanoyl]-$N^1$-[(7S)-5-methyl-6-oxo-6,7-dihydro-5H-dibenzo[b,d]azepin-7-yl]-$_L$-alaninamide (LY411,575) in the CRND8 mouse," J Pharmacol Exp Ther., 319:1133-43 (Dec. 2006).
Ikeda and Dikic, "Atypical ubiquitin chains: new molecular signals. "Protein Modifications: Beyond the Usual Suspects" review series," EMBO Reports, 2008, 9:536-542.
Incesulu and Nadal, "Correlation of acoustic threshold measures and spiral ganglion cell survival in severe to profound sensorineural hearing loss: implications for cochlear implantation," The Annals of Otology, Rhinology, and Laryngology, 1998, 107:906-911.
Inoue et al., "Mule/Huwel/Arf-BP1 suppresses Ras-driven tumorigenesis by preventing c-Myc/Mizl-mediated down-regulation ofp21 and p15," Genes & Development, 2013, 27: 1101-1114.
International Preliminary Report on Patentability for PCT/US2009/065747, issued May 24, 2011'.
International Preliminary Report on Patentability in International Application No. PCT/US2013/058446, issued Mar. 10, 2015, 11 pages.
International Preliminary Report on Patentability in International Application No. PCT/US2016/064727, mailed on Jun. 14, 2018, 9 pages.
International Preliminary Report on Patentability in International Application No. PCT/US2017/015379, mailed on Aug. 9, 2018, 11 pages.
International Preliminary Report on Patentability issued in corresponding International Application No. PCT/US2007/084654, mailed May 28, 2009.

(56) References Cited

OTHER PUBLICATIONS

International Search Report and Written Opinion in International Application No. PCT/US15/43976, mailed on Jan. 20, 2016, 16 pages.
International Search Report and Written Opinion in International Application No. PCT/US2013/058446, mailed Dec. 26, 2013, 8 pages.
International Search Report and Written Opinion in International Application No. PCT/US2016/064727, mailed on May 1, 2017, 18 pages.
International Search Report and Written Opinion in International application No. PCT/US2017/015379, mailed on May 31, 2017, 18 pages.
International Search Report issued in corresponding International Application No. PCT/US2007/84654, mailed Oct. 3, 2008.
Inuzuka et al., "SCFFBW7 regulates cellular apoptosis by targeting MCL1 for ubiquitylation and destruction," Nature, 2012, 470:104-109.
Ito et al., "Neurotrophins Facilitate Neuronal Differentiation of Cultured Neural Stem Cells via Induction of mRNA Expression of Basic Helix-Loop-Helix Transcription Factors Mash1 and Math1," J. Neurosci. Res., 71:648-658 (2003).
Ivan et al., "HIFalpha targeted for VHL-mediated destruction by praline hydroxylation: implications for 02 sensing," Science, 2001,292:464-468.
Ivanov et al., "Genes required for Drosophila nervous system development identified by RNA interference," Proc. Nat. Acad. Sci., 101:16216-16221 (2004).
Izumikawa et al., "Auditory hair cell replacement and hearing improvement by Atoh1 gene therapy in deaf mammals," Nat Med., 11(3)271-6 (Mar. 2005).
Izumikawa et al., "Auditory hair cell replacement and hearing improvement by Atoh1 gene therapy in deaf mammals," Natl. Med., 11(3):271-276 (Mar. 2005).
Jaakkola et al., "Targeting ofHIF-alpha to the von Hippel-Lindau ubiquitylation complex by 02-regulated prolyl hydroxylation," Science, 2001, 292:468-472.
Jahan et al., "Beyond generalized hair cells: molecular cues for hair cell types," Hear Res, Mar. 2013, 297:30-41.
Jarriault et al., "Delta-1 Activation of Notch-1 Signaling Results in HES-1 Transactivation," Mol. Cell. Biol, 1998, 18:7423-7431.
Jarriault et al., "Signalling downstream of activated mammalian Notch," Nature, 1995, 377:355-358.
Jeon et al., "Notch Signaling Alters Sensory or Neuronal Cell Fate Specification of Inner Ear Stem Cells," J. Neurosci, 2011, 31:8351-8358.
Jeon et al., "Bone marrow mesenchymal stem cells are progenitors in vitro for inner ear hair cells," Molecular and Cellular Neurosciences, 2007, 34:59-68.
Jeon et al., "Bone marrow mesenchymal stem cells are progenitors in vitro for inner ear hair cells," Molecular and Cellular Neurosciences, 34:59-68 (2007).
Jeon et al., "Notch signaling alters sensory or neuronal cell fate specification of inner ear stem cells," J. Neurosci., 31:8351-8 (Jun. 8, 2011).
Jiang et al., "Neuroectodermal differentiation from mouse multipotent adult progenitor cells," Proc. Natl. Acad. Sci .U.S.A, 100:11854-11860 (2003).
Jiang et al., "Pluripotency of mesenchymal stem cells derived from adult marrow," Nature, 418:41-49 (2002).
Jin et al., "Systematic analysis and nomenclature of mammalian F-box proteins," Genes Dev, 2004, 18(21):2573-2580.
JP Office Action in Japanese Appln. No. 2015-531223, dated Sep. 11, 2019, 5 pages (with English translation).
JP Office Action in Japanese Appln. No. 2015-531223, dated Jan. 5, 2021, 20 pages (with English translation).
JP Office Action in Japanese Appln. No. 2018-540010, dated Mar. 2, 2021, 6 pages (with English translation).
JP Office Action in Japanese Appln. No. 2019-091552, dated Apr. 28, 2020, 8 pages (with English translation).
JP Office Action in Japanese Appln. No. 2019-228284, dated Jan. 26, 2021, 5 pages (with English translation).
Kaneko et al., "Musashi1: an evolutionally conserved marker for CNS progenitor cells including neural stem cells," Dev Neurosci., 22:139-53 (2000).
Kawamoto et al., "Spontaneous hair cell regeneration in the mouse utricle following gentamicin ototoxicity," Hearing Research, 2009, 247: 17-26.
Kelley et al., "Regulation of cell fate in the sensory epithelia of the inner ear," Nat Rev Neurosci, 2006, 7: 837-849.
Kicic et al., "Differentiation of Marrow Stromal Cells into Photoreceptors in the Rat Eye," J. Neurosci., 23:7742-7749 (2003).
Kiernan et al., "Sox2 is required for sensory organ development in the mammalian inner ear," Nature, 434:1031-1035 (2005).
Kim et al., "Dopamine neurons derived from embryonic stem cells function in an animal model of Parkinson's disease," Nature, 418:50-6 (2002).
Kim et al., "NeuroD-null mice are deaf due to a severe loss of the inner ear sensory neurons during development," Develop., 128:417-426 (2001).
Klisch et al., "In vivo Atohl targetome reveals how a proneural transcription factor regulates cerebellar development," PNAS, 2011.
Knippschild et al., "The CK1 family: contribution to cellular stress response and its role in carcinogenesis," Frontiers in Oncology, May 2014, 4: 32 pages.
Knippschild et al., Metaanalysis to Estimate the Expected Drop Out-Rates Reported in Clinical Trials on Cataract Surgery, 2014, 231: 151-157 (with English abstract).
Kondo et al., "Sonic Hedgehog and retinoic acid synergistically promote sensory fate specification from bone marrow-derived pluripotent stem cells," Proc. Natl. Acad. Sci. U.S.A., 102(13):4789-4794 (Mar. 2005).
Kondo et al., "Wnt Signaling Promotes Neuronal Differentiation From Mesenchymal Stem Cells Through Activation ofTlx3," Stem Cells, 2011.
Kopan et al., "The Canonical Notch Signaling Pathway: Unfolding the Activation Mechanism," Cell, 2009, 137:216-233.
Kurokawa et al., "A network of substrates of the E3 ubiquitin ligases MDM2 and HUWEI control apoptosis independently ofp53," Science Signaling, 2013, 6:ra32.
Lanford et al., "Notch signalling pathway mediates hair cell development in mammalian cochlea," Nature Genetics, 21:289-292 (1999).
Lang et al., "Contribution of Bone Marrow Hematopoietic Stem Cells to Adult Mouse Inner Ear: Mesenchymal Cells and Fibrocytes," J .Comp. Neurol., 496:187-201 (2006).
Lanzoni et al., "MDL 28170 Attenuates Gentamicin Ototoxicity," Audiological Medicine, 2005, 3: 82-89.
Latres et al., "The human F box protein beta-Trop associates with the Cull/Skpl complex and regulates the stability ofbeta-catenin," Oncogene, Jan. 1999, 18:849-854.
Ledent et al., "Phylogenetic analysis of the human basic helix-loop-helix proteins," Genome Biology, 2002 3:research0030.1.
Lee et al., "Proteasome inhibitors induce auditory hair cell death through peroxisome dysfunction," Biochem. Biophys. Res. Comm., Jan. 2015, 456(1):269-274.
Lee et al., "Efficient generation of midbrain and hindbrain neurons from mouse embryonic stem cells," Nat. Biotech., 18:675-9, (2000).
Lee et al., "EZH2 generates a methyl degron that is recognized by the DCAF1/DDB1/CUL4 E3 ubiquitin ligase complex," Molecular Cell, 2012, 48:572-586.
Leon et al.,. "Insulin-Like Growth Factor-I Regulates Cell Proliferation in the Developing Inner Ear, Activating Glycosyl-Phosphatidylinositol Hydrolysis and Fos Expression," Endocrinol., 136:3494-3503 (1995).
Li et al., "Correlation of Pax-2 Expression with Cell Proliferation in the Developing Chicken Inner Ear," J. Neurobiol., 60:61-70 (2004).
Li et al., "Generation of hair cells by stepwise differentiation of embryonic stem cells," Proc. Natl. Acad. Sci U.S.A., 100:13495-13500 (2003).
Li et al., "Generation of hair cells by stepwise differentiation of embryonic stem cells," Proc. Natl. Acad. Sci. U.S.A. Nov. 2003, 100(23):13495-13500.

(56) References Cited

OTHER PUBLICATIONS

Li et al., "Pluripotent stem cells from the adult mouse inner ear," Nat. Med., 9:1293-1299 (2003).
Li et al., "Specification of motoneurons from human embryonic stem cells," Nat. Biotechnol., 23:215-21 (2005).
Li et al., "Stem cells as therapy for hearing loss," Trends Mol. Med., 10:309-315 (2004).
Lin et al., "Hair cell damage recruited Lgr5-expressing cells are hair cell progenitors in neonatal mouse utricle," Front Cell Neurosci, Apr. 2015, 9: 1-11.
Lin et al., "Inhibition of notch activity promotes non-mitotic regeneration of hair cells in the adult mouse utricles," J Neurosci., 31(43):15329-15339 (Oct. 26, 2011).
Lo et al., "Mammalian achaete-scute homolog 1 is transiently expressed by spatially restricted subsets of early neuroepithelial and neural crest cells," Genes & Development, 1991, 5: 1524-1537.
Lu et al., "Abstract #: 774: The Influence of Glycogen Synthase Kinase 3 on Cell Proliferation in the Murine Vestibular Sensory Epithelium," ARO 31st Annual Midwinter Meeting, Phoenix, Arizona, Feb. 16-21, 2008, 3 pages.
Lu et al., "The Influence of Glycogen Synthase Kinase 3 in Limiting Cell Addition in the Mammalian Ear," Develop. Neurobiol., 68:1059-1075 (2008).
Luistro et al., "Preclinical Profile of a Potent γ-Secretase Inhibitor Targeting Notch Signaling with In vivo Efficacy and Pharmacodynamic Properties," Cancer Res, Oct. 2009, 69(19):7672-7690.
Lumpkin et al., "Math1-driven GFP expression in the developing nervous system of transgenic mice," Gene Expr Patterns, 3:389-95 (Aug. 2003).
Lumpkin et al., "Math1-driven GFP expression in the developing nervous system of transgenic mice," Gene. Expr. Patterns, 3:389-395 (2003).
Ma and Raible, "Signaling pathways regulating zebrafish lateral line development," Current Biology, 2009, 19:R381-386.
Ma et al., "Neurogenin 1 Null Mutant Ears Develop Fewer, Morphologically Normal Hair Cells in Smaller Sensory Epithelia Devoid of Innervation," Assoc. Res. Otolaryngol., 1:129-143 (2000).
Madisen et al., "A robust and high-throughput Cre reporting and characterization system for the whole mouse brain," Nat Neurosci, 2010, 13: 133-140.
Maksimovic et al., "Epidermal Merkel cells are mechanosensory cells that tune mammalian touch receptors," Nature, 2014, 509:617-621.
Mangi et al., "Mesenchymal stem cells modified with Akt prevent remodeling and restore performance of infarcted hearts," Nat. Med., 9:1195-201 (2003).
Markkanen et al., "Regulation of oxidative DNA damage repair by DNA polymerase A and MutYH by cross-talk of phosphorylation and ubiquitination," PNAS, 2012, 109:437-442.
Masuda et al., "Dual antitumor mechanisms of notch signaling inhibitor in a T-cell acute lymphoblastic leukemia xenograft model," Cancer Sci., 100(12):2444-2450 (Dec. 2009).
Matei et al., "Smaller Inner Ear Sensory Epithelia in Neurog1 Null Mice Are Related to Earlier Hair Cell Cycle Exit," Dev. Dyn., 234:633-50 (2005).
Matsui et al., "Regeneration and replacement in the vertebrate inner ear," Drug Discov. Today, 10:1307-12 (2005).
Meierhofer et al., "Quantitative analysis of global ubiquitination in HeLa cells by mass spectrometry," Journal of Proteome Research, 2008, 7:4566-4576.
Mezey et al., "Transplanted bone marrow generates new neurons in human brains," Proc. Natl. Acad. Sci. U.S.A., 100:1364-1369 (2003).
Miesegaes et al., "Identification and subclassification of new Atoh1 derived cell populations during mouse spinal cord development," Developmental Biology, Mar. 2009, 327:339-351.
Mikulec et al., "Permeability of the round window membrane is influenced by the composition of applied drug solutions and by common surgical procedures," Otol Neurotol., 29:1020-6 (Oct. 2008).
Mitani et al., "Differential Effects between γ-Secretase Inhibitors and Modulators on Cognitive Function in Amyloid Precursor Protein-Transgenic and Nontransgenic Mice," J. Neuroscience, Feb. 2012.
Mizutari et al., "Notch inhibition induces cochlear hair cell regeneration and recovery of hearing after acoustic trauma," Neuron, 2013, 77: 58-69.
Mizutari et al., "Notch Inhibition induces cochlear hair cell regeneration and recovery of hearing after acoustic trauma," Neuron, Jan. 2013, 77(1): 58-69.
Moon et al., "WNT and B-catenin signalling: diseases and therapies," Nature Reviews, Sep. 2004, 5: 689-699.
Morrison et al., "Mammalian Merkel cells are descended from the epidermal lineage," Developmental Biology, 2009, 336:76-83.
Murre et al., "Interactions between heterologous helixloop-helix proteins generate complexes that bind specifically to a common DNA sequence.," Cell, 1989, 58:537-544.
Murry et al., "Haematopoietic stem cells do not transdifferentiate into cardiac myocytes in myocardial infarcts," Nature., 428:664-668 (2004).
Nadol, Jr. et al., "Degenerative Changes in the Organ of Corti and Lateral Cochlear Wall in Experimental Endolymphatic Hydrops and Human Meniere's Disease," Acta Otolaryngol, 1995, Suppl 519: 47-59.
Naito Yasushi et al., "Transplantation of bone marrow stromal cells into the cochlea of chinchillas," NeuroReport, Lippincott Williams & Wilkins, 15:1-4 (2004).
Nakagawa, "Aiming for the treatment of inner ear diseases—the forefront of basic research," Bulletin of the Japan Otolaryngology Society, 2008, 11(10):655-663 (with machine abstract).
Naujokat and Saric, "Concise review: role and function of the ubiquitinproteasome system in mammalian stem and progenitor cells," Stem Cells, 2007, 25 :2408-2418.
Noy et al., "HUWEL ubiquitinates MyoD and targets it for proteasomal degradation," Biochemical and Biophysical Research Communications, 2012, 418:408-413.
Oesterle et al., "Sox2 and JAGGED1 expression in normal and drug-damaged adult mouse inner ear," J Assoc Res Otolaryngol., 9:65-89 (Mar. 2008).
Office Action in European Application No. 13836099.5, dated Jul. 25, 2018, 5 pages.
Office Action in Japanese Application No. 2015-178811, dated Jun. 5, 2018, 12 pages (with English translation).
Office Action in Japanese Application No. 2015-178811, dated Oct. 17, 2017, 6 pages (with English translation).
Office Action in Japanese Application No. 2015-531223, dated Jan. 15, 2019, 6 pages (with English translation).
Office Action in Japanese Application No. 2015-531223, dated Jul. 11, 2017, 8 pages (with English translation).
Office Action in Japanese Application No. 2015-531223, dated Jun. 19, 2018, 7 pages (with English translation).
Office Action issued in AU2009316264 on Jan. 16, 2015, 5 pages.
Office Action issued in CA2,669,693 on Apr. 4, 2014, 4 pages.
Office Action issued in EP07871464.9 on May 6, 2014, 5 pages.
Office Action issued in European Application No. 09828380.7 on Mar. 26, 2014, 6 pages.
Office Action issued in Japanese Application No. 2011-537715 issued on Feb. 4, 2014 (translation) 4 pages.
Office Action issued in JP2009-537328 on Feb. 12, 2013 (7 pages).
Office Action issued in JP2011-537715 on Jan. 20, 2015 with English translation (7 pages).
Office Action issued in JP2015-178811 on Mar. 7, 2017 with English translation (5 pages).
Ohyama et al., "Wnt signals mediate a fate decision between otic placode and epidermis," Development, 2006, 133:865-875.
Okubo and Hogan, "Hyperactive Wnt signaling changes the developmental potential of embryonic lung endoderm, " Journal of Biology, 2004, 3: 11.
Oshima et al., "Differential distribution of stem cells in the auditory and vestibular organs of the inner ear," J Assoc Res Otolaryngol., 8:18-31 (Mar. 2007).
Oshima et al., "Mechanosensitive hair cell-like cells from embryonic and induced pluripotent stem cells," Cell, 2010, 141(4): 704-716.

(56) References Cited

OTHER PUBLICATIONS

Pagani et al., "Autologous Skeletal Myoblasts Transplanted to Ischemia-Damaged Myocardium in Humans," J. Am. Coll. Cardiol., 41:879-888 (2003).
Pan et al., "A novel Atohl "self-terminating" mouse model reveals the necessity of proper Atoh1 level and duration for hair cell differentiation and viability," PloS One, 2012, 7:e30358.
Pandya et al., "A structural element within the HUWEL HECT domain modulates self-ubiquitination and substrate ubiquitination activities," The Journal of Biological Chemistry, 2010, 285:5664-5673.
Parker et al., "An independent construct for conditional expression of atonal homolog-1," Human Gene Therapy Methods, 2014, 25:1-13.
Parker et al., "Primary culture and plasmid electroporation of the murine organ of Corti," Journal of Visualized Experiments, 2010.
Parker, "Biotechnology in the treatment of sensorineural hearing loss: foundations and future of hair cell regeneration," Journal of Speech, Language, and Hearing Research, 2011, 54: 1 709-1731.
Patzel et al., "Design of siRNAs producing unstructured guide-RNAs results in improved RNA interference efficiency," Nature Biotechnol., 23:1440-1444 (2005).
Pauley et al., "Expression and Function of FGF10 in Mammalian Inner Ear Development," Dev. Dyn., 227:203-215 (2003).
Pedersen, "Cells for Medicine," Scientif. Am., 280:68-73 (1999).
Peng et al., "A proteomics approach to understanding protein ubiquitination," Nature Biotechnology, 2003, 21:921-926.
Petit, "Usher syndrome: from genetics to pathogenesis," Annu Rev Genomics Hum Genet., 2:271-97 (2001).
Pickart, "Ubiquitin enters the new millennium," Molecular Cell, Sep. 2001, 8(3):499-504.
Pirvola et al., "Neurotrophic Factors during Inner Ear Development," Curr. Top. Dev. Biol., 57:207-223 (2003).
Pittenger et al., "Multilineage Potential of Adult Human Mesenchymal Stem Cells," Sci., 284:143-147 (1999).
Plum et al., "Connexin31-deficiency in mice causes transient placental dysmorphogenesis but does not impair hearing and skin differentiation," Dev Biol., 231:334-47 (2001).
Presente et al., "Notch is required for long-term memory in Drosophila," Proc. Nat. Acad. Sci., 101:1764-1768 (2004).
Price, "CKI, there's more than one: casein kinase I family members in Wnt and Hedgehog signaling," Genes & Development, 20: 399-410.
Purow et al., "Expression of Notch-1 and Its Ligands, Delta-Like-1 and Jagged-1, Is Critical for Glioma Cell Survival and Proliferation," Cancer Res., 65:2353-2363 (2005).
Qyang et al., "The renewal and differentiation of Isl 1 + cardiovascular progenitors are controlled by a Wnt/beta-catenin pathway," Cell Stem Cell, 2007, 1: 165-179.
Rask-Andersen et al., "Regeneration of human auditory nerve. In vitro/in video demonstration of neural progenitor cells in adult human and guinea pig spiral ganglion," Hear. Res., 203:180-191 (2005).
Ravid and Hochstrasser, "Diversity of degradation signals in the ubiquitin-proteasome system," Nat Rev Mol Cell Biol, 2008, 9(9):679-90.
RCE and Response to Final Office Action issued in U.S. Appl. No. 13/130,607, filed Apr. 21, 2014.
Rena et al., "D4476, a cell-permeant inhibitor of CK1, suppresses the site-specific phosphorylation and nuclear exclusion of FOXOIa," EMBO reports, 2004, 5: 60-65.
Response to Non-Final Office Action issued in U.S. Appl. No. 13/130,607, filed Jul. 19, 2013.
Response to Non-Final Office Action issued in U.S. Appl. No. 13/130,607 on Oct. 23, 2014 filed Apr. 23, 2015 (10 pages).
Response to Restriction Requirement issued in U.S. Appl. No. 13/130,607, filed Dec. 12, 2012.
Response to Restriction Requirement issued in U.S. Appl. No. 13/759,441 on Dec. 22, 2014 filed Mar. 19, 2015 (4 pages).
Response to U.S. Final Office Action in U.S. Appl. No. 13/130,607, dated Jan. 15, 2016.
Restriction Requirement issued in U.S. Appl. No. 13/130,607on Oct. 12, 2012.
Restriction Requirement issued in U.S. Appl. No. 13/759,441 on Dec. 22, 2014 (4 pages).
Riccomagno et al., "Wnt-dependent regulation of inner ear morphogenesis is balanced by the opposing and supporting roles of Shh," Genes & Development, 2005, 19: 1612-1623.
Roberson et al., "Direct transdifferentiation gives rise to the earliest new hair cells in regenerating avian auditory epithelium," Journal of Neuroscience Research, 2004,7 8: 461-4 71.
Roccio et al., "Cell cycle reactivation of cochlear progenitor cells in neonatal FUCCI mice by a GSK3 small molecule inhibitor," Sci Rep, Dec. 2015, 5: 1-11.
Ross et al., "Basic helix-loop-helix factors in cortical development," Neuron, Jul. 2003, 39: 13-25.
Rotin and Kumar, "Physiological functions of the HECT family ofubiquitin Ligases," Nature Reviews Molecular Cell Biology, 2009, 10:398-409.
Rubel et al., "Mammalian Vestibular Hair Cell Regeneration," Science, Feb. 1995, 267(5198):701-707.
Ryals and Rubel, "Hair Cell Regeneration After Acoustic Trauma in Adult Coturnix Quail," Science, Jun. 1988, 240:1774-1776.
Ryusuke et al., "Pharmacological inhibition of Notch signaling in the mature guinea pig cochlea" Neuroreport, Lippincott Williams and Wilkins, UK, Dec. 2007, 18(18): 1911-1914.
Sakaguchi et al., "Spatiotemporal patterns of Musashi1 expression during inner ear development," Neuroreport, 15:997-1001 (Apr. 29, 2004).
Sakamoto et al., "Fates of mouse embryonic stem cells transplanted into the inner ears of adult mice and embryonic chickens," Acta Otolarynol Suppl., 551:48-52 (2004).
Salt and Plontke, "Principles of local drug delivery to the inner ear," Audiol Neurootol., 14:350-60 (2009).
Samon et al., "Preclinical analysis of the γ-secretase inhibitor PF-03084014 in combination with glucocorticoids in T-cell acute lymphoblastic leukemia," Mol Cancer Ther., 11(7):1565-1575 (Jul. 2012).
Samstein an Platt, "Physiologic and immunologic hurdles to xenotransplantation," Journal of American Society of Nephrology, 12:182-193 (2001).
Sarrazin et al., "Proneural gene requirement for hair cell differentiation in the zebrafish lateral line," Dev. Biol., 295:534-545 (2006).
Satoh and Fekete, "Clonal analysis of the relationships between mechanosensory cells and the neurons that innervate them in the chicken ear," Develop., 132:1687-1697 (2005).
Scheffner and Staub, "HECT E3s and human disease," BMC Biochemistry, Nov. 2007, 8 Suppl 1:S6.
Schwarz et al., "Characterization of human hect domain family members and their interaction with UbcH5 and UbcH7," The Journal of Biological Chemistry, 1998, 273: 12148-12154.
Shakoori et al., "Deregulated GSK3b activity in colorectal cancer: Its association with tumor cell survival and proliferation," Biochem and Biophys Research Comm, 2005, 334: 1365-1373.
Shi et al., "Abstract #: 732: Interaction of B-Catenin with an Atohl 3' Enhancer Upregulates Atohl Expression and Increases Differentiation of Progenitors to Hair Cells," ARO 32nd Annual Midwinter Meeting, Baltimore, Maryland, Feb. 14-19, 2009, 3 pages.
Shi et al., "Generation of hair cells in neonatal mice by beta-catenin overexpression in Lgr5-positive cochlear progenitors," PNAS, 2013, 110: 13851-13856.
Shi et al., "Wnt-responsive lgr5-expressing stem cells are hair cell progenitors in the cochlea," J Neurosci, 2012, 32: 9639-9648.
Shi et al., "β-Catenin Up-regulates Atoh1 Expression in Neural Progenitor Cells by Interaction with an Atoh1 3' Enhancer," J Biol Chem, Jan. 2010, 285(1):392-400.
Shi et al., "β-Catenin Is Required for Hair-Cell Differentiation in the Cochlea," The Journal of Neuroscience, 2014, 34:6470-6479.
Skowyra et al., "F-box proteins are receptors that recruit phosphorylated substrates to the SCF ubiquitin-ligase complex," Cell, 1997, 91:209-219.

(56) References Cited

OTHER PUBLICATIONS

Sowa et al., "Defining the human deubiquitinating enzyme interaction landscape," Cell, 2009, 138:389-403.
Sparling et al., "Adipocyte-specific blockade of gamma-secretase, but not inhibition of Notch activity, reduces adipose insulin sensitivity," Molecular Metabolism, 2016, 5: 113-121.
Spence et al., "A ubiquitin mutant with specific defects in DNA repair and multiubiquitination," Molecular and Cellular Biology, 1995, 15:1265-1273.
Staecker et al., "Vestibular hair cell regeneration and restoration of balance function induced by math1 gene transfer," Otology & Neurotology, 2007, 28:223-231.
Stahle et al., "Long-term Progression of Meniere's Disease," Acta Otolaryngol, 1991, Suppl. 485: 78-83.
Stallwood et al., "Small Interfering RNA-Mediated Knockdown of Notch Ligands in Primary $CD4^+$ T Cells and Dendritic Cells Enhances Cytokine Production," J. Immunol., 177:885-895 (2006).
Stambolic et al., "Lithium inhihits glycogen synthase kinase-3 activity and mimics Wingless signalling in intact cells," Current Biology, 1996, 6: 1664-1668.
Stevens et al., "Forced activation of Wnt signaling alters morphogenesis and sensory organ identity in the chicken inner ear," Dev. Biol, 2003, 261: 149-164.
Stone and Cotanche, "Identification of the timing of S phase and the patterns of cell proliferation during hair cell regeneration in the chick cochlea," The Journal of Comparative Neurology 341:50-67.
Supplementary European Search Report issued in EP09828380 on Nov. 30, 2012 (8 pages).
Swan et al., "Inner ear drug delivery for auditory applications," Advanced Drug Delivery Reviews, 2008, 60: 1583-1599.
Sziklai et al., "Otosclerosis: an organ-specific inflammatory disease with sensorineural hearing loss," Eur. Arch. Otorhinolaryngol., 2009, 266:1711-1718.
Tai and Schuman, "Ubiquitin, the proteasome and protein degradation in neuronal function and dysfunction," Nature Reviews Neuroscience, 2008, 9:826-838.
Takebayashi et al., "Multiple roles of Notch signaling in cochlear development," Developmental Biology, 2007, 307: 165-178.
Tan et al., "Parallel SCF adaptor capture proteomics reveals a role for SCFFBXL1 7 in NRF2 activation via BACH1 repressor turnover," Molecular Cell, 2013, 52:9-24.
Tiveron et al., "Role of Phox2b and Mash1 in the generation of the vestibular efferent nucleus," Developmental Biology, 2003, 260:46-57.
Tsuchiya et al., "Reciprocal targeting ofHath1 and beta-catenin by Wnt glycogen synthase kinase 3beta in human colon cancer," Gastroenterology, 2007, 132:208-220.
Varshavsky, "Naming a targeting signal," Cell, 1991, 64:13-15.
Vierbuchen et al., "Direct conversion of fibroblasts to functional neurons by defined factors," Nature, 463:1035-41 (Feb. 25, 2010).
Wagers et al., "Little Evidence for Developmental Plasticity of Adult Hematopoietic Stem Cells," Science, 297:2256-2259 (2002).
Wagner and Jung, "New lysine methyltransferase drug targets in cancer," Nature Biotechnology, 2012, 30:622-623.
Wang et al., "Cell fusion is the principal source of bone-marrow-derived hepatocytes," Nature, 422:897-901 (2003).
Wang et al., "Dynamics of noise-induced cellular injury and repair in the mouse cochlea," J Assoc Res Otolaryngol., 3:248-68 (Sep. 2002).
Wang et al., "HUWE1 interacts with BRCA1 and promotes its degradation in the ubiquitin-proteasome pathway," Biochemical and Biophysical Research Communications, 2013.
Warchol et al., "Regenerative proliferation in inner ear sensory epithelia from adult guinea pigs and humans," Science, 1993, 259: 1619-1622.
Warner et al., "Expression of ZIC Genes in the Development of the Chick Inner Ear and Nervous System," Dev. Dyn., 226:702-712 (2003).
Weimann et al., "Contribution of transplanted bone marrow cells to Purkinje neurons in human adult brains," Proc. Natl. Acad. Sci. U.S.A., 100:2088-2093 (2003).
White et al., "Mammalian cochlear supporting cells can divide and trans-differentiate into hair cells," Nature, 441:984-987 (2006).
Wolfe, "γ-secretase Inhibition and Modulation for Alzheimer's Disease," Curr Alzheimer Res., 5(2):158-164 (Apr. 2008) (Author Manuscript).
Wong et al., "Chronic treatment with the gamma-secretase inhibitor L Y -411,575 inhibits beta-amyloid peptide production and alters lymphopoiesis and intestinal cell differentiation," J Biol Chem., 279:12876-82 (Mar. 26, 2004).
Woods et al., "Math1 regulates development of the sensory epithelium in the mammalian cochlea," Nat. Neurosci., 7:1310-1318 (2004).
Written Opinion of the International Searching Authority for PCT/US2009/065747, mailed Apr. 8, 2010.
Written Opinion of the International Searching Authority issued in corresponding International Application No. PCT/US2007/84654, mailed Oct. 3, 2008.
Wu et al., "Structure of a beta-TrCP 1-Skp 1-beta-catenin complex: destruction motif binding and lysine specificity of the SCF(beta-TrCP 1) ubiquitin ligase," Molecular Cell, 2003, 11:1445-1456.
Yamamoto et al., "Inhibition of Notch/RBP-J signaling induces hair cell formation in neonate mouse cochleas," J. Mol. Med., 84(1):37-45 (Jan. 2006).
Yang et al., "E3 ubiquitin ligase Mule ubiquitinates Miz1 and is required for TNFalphainduced INK activation," PNAS, 2010, 107:13444-13449.
Yang et al., "Generation and characterization of Atoh1-Cre knock-in mouse line," Genesis, 2010, 48:407-413.
Yang et al., "Requirement of Math 1 for Secretory Cell Lineage Commitment in the Mouse Intestine," Science, 2001, 294:2155.
Ye et al., "Recognition ofphosphodegron motifs in human cyclin E by the SCF(Fbw7) ubiquitin ligase," The Journal of biological chemistly, 2004, 279:50110-50119.
Yoneda, "Attempt to regenerate cochlear morphology and function using gene transfer," Otol. Jpn., May 2006, 16(2):135-138 (with machine translation).
Zaragosi et al., "Effects of GSK3 inhibitors on in vitro expansion and differentiation of human adipose-derived stem cells into adipocytes," BMC Cell Biology, 2008, 9: 11.
Zhang et al., "Gene regulatory networks mediating canonical Wnt signal-directed control of pluripotency and differentiation in embryo stem cells," Stem Cells, 2013, 31(12):2667-79.
Zhang et al., "Mule determines the apoptotic response to HDAC inhibitors by targeted ubiquitination and destruction ofHDAC2," Genes & Development, 2011, 25:2610-2618.
Zhao et al., "The HECT-domain ubiquitin ligase Huwe1 controls neural differentiation and proliferation by destabilizing the N-Myc oncoprotein," Nature Cell Biology, 2008, 10:643-653.
Zhao et al., "The N-Myc-DLL3 cascade is suppressed by the ubiquitin ligase Huwe1 to inhibit proliferation and promote neurogenesis in the developing brain," Developmental Cell, 2009, 17:210-221.
Zheng and Gao, "Overexpression of Math1 induces robust production of extra hair cells in postnatal rat inner ears," Nat. Neurosci., 2000, 3:580-586.
Zheng et al., "Induction of Cell Proliferation by Fibroblast and Insulin-Like Growth Factors in Pure Rat Inner Ear Epithelial Cell Cultures," J. Neurosci., 17:216-226 (1997).
Zheng et al., "Overexpression of Math 1 induces robust production of extra hair cells in postnatal rat inner ears," Natl. Neurosci., 3(6):580-586 (Jun. 2000).
Zhong et al., "Mule/ARF-BP1, a BH3-only E3 ubiquitin ligase, catalyzes the polyubiquitination of Mcl-1 and regulates apoptosis," Cell, 2005, 21:1085-1095.
Zine et al., "Hes1 and Hes5 activities are required for the normal development of the hair cells in the mammalian inner ear," J Neurosci., 21:4712-20 (Jul. 1, 2001).
Zine et al., "Notch signaling regulates the pattern of auditory hair cell differentiation in mammals," Development., 2000, 127:3373-3383.

(56) References Cited

OTHER PUBLICATIONS

Adamo et al., "LSD1 regulates the balance between self-renewal and differentiation in human embryonic stem cells, " Nat Cell Biol, Jun. 2011, 13(6):652-659, 20 pages.
Ahmed and Streit, "LSD1 interacts with cMyb to demethylate repressive histone marks and maintain inner ear progenitor identity," Development, 2018, 145(4):dev160325, 9 pages.
Azuara et al., "Chromatin signatures of pluripotent cell lines," Nat Cell Biol, May 2006, 8(5):532-538, 11 pages.
Ballas et al., "Regulation of neuronal traits by a novel transcriptional complex," Neuron, Aug. 2001, 31(3):353-365.
Bernstein et al., "A bivalent chromatin structure marks key developmental genes in embryonic stem cells," Cell, Apr. 2006, 125(2):315-326.
Bernstein et al., "Methylation of histone H3 Lys 4 in coding regions of active genes," Proc Natl Acad Sci U S A, Jun. 2002, 99(13):8695-8700.
Borden et al., "Hyaluronic Acid Hydrogel Sustains the Delivery of Dexamethasone across the Round Window Membrane," Audiol Neurootol., 2011, 16(1):1-11.
Cai et al., "Characterization of the transcriptome of nascent hair cells and identification of direct targets of the Atoh1 transcription factor," J Neurosci, Apr. 2015, 35(14):5870-5883.
Carlisle et al., "Specific expression of Kcna10, Pxn and Odf2 in the organ of Corti," Gene Expr Patterns, May 2012, 12:172-179.
Chen and Segil, "p27$^{Kip1}$ links cell proliferation to morphogenesis in the developing organ of Corti," Development, 1999, 126(8):1581-1590.
Chen et al., "Histone Demethylase LSD1 Promotes Adipocyte Differentiation through Repressing Wnt Signaling," Cell Chem Biol, Sep. 2016, 23(10):1228-1240.
Chonko et al., "Atoh1 directs hair cell differentiation and survival in the late embryonic mouse inner ear," Dev Biol, Sep. 2013, 381(2):401-410.
Dobin et al., "STAR: ultrafast universal RNAseq aligner," Bioinformatics, Jan. 2013, 29(1):15-21.
Escobar-Chávez et al., "Applications of thermo-reversible pluronic F-127 gels in pharmaceutical formulations," J Pharm Pharm Sci., 2006, 9(3):339-58.
Ferrer-Vaquer et al., "A sensitive and bright single-cell resolution live imaging reporter of Wnt/ss-catenin signaling in the mouse," BMC Dev Biol, Dec. 2010, 10:121, 18 pages.
Forneris et al., "Histone demethylation catalysed by LSD1 is a flavin-dependent oxidative process," FEBS Lett, Apr. 2005, 579(10):2203-2207.
Fuerer and Nusse, "Lentiviral vectors to probe and manipulate the Wnt signaling pathway," PLoS One, 2010, 5(2):e9370, 7 pages.
Ge et al., "Distribution of PLGA nanoparticles in chinchilla cochleae," Otolaryngol Head Neck Surg., Oct. 2007, 137(4):619-23.
Geng et al., "Comprehensive Expression of Wnt Signaling Pathway Genes during Development and Maturation of the Mouse Cochlea," PLoS One, Feb. 2016, 11(2):e0148339, 18 pages.
Groves, "The challenge of hair cell regeneration," Exp Biol Med (Maywood), Apr. 2010, 235(4):434-446.
Hanna et al., "Pluripotency and cellular reprogramming: facts, hypotheses, unresolved issues," Cell, Nov. 2010, 143(4):508-525.
Havenith et al., "Spiral ganglion cell survival after round window membrane application of brain-derived neurotrophic factor using gelfoam as carrier," Hearing Research, Feb. 2011, 272(1-2):168-177.
Heintzman et al., "Distinct and predictive chromatin signatures of transcriptional promoters and enhancers in the human genome," Nat Genet, Mar. 2007, 39(3):311-318.
Hödar et al., "Genome-wide identification of new Wnt/beta-catenin target genes in the human genome using CART method," BMC Genomics, 2010, 11:348, 15 pages.
Horie et al., "Sustained delivery of lidocaine into the cochlea using poly lactic/glycolic acid microparticles," Laryngoscope, 2010, 120(2):377-83.
Hu et al., "Diphtheria Toxin-Induced Cell Death Triggers Wnt-Dependent Hair Cell Regeneration in Neonatal Mice," J Neurosci, 2016, 36:9479-9489.
Hu et al., "Wnt/beta-catenin signaling in murine hepatic transit amplifying progenitor cells," Gastroenterology, Nov. 2007, 133(5):1579-1591.
Hyun et al., "In Vitro and in Vivo Release of Albumin Using a Biodegradable MPEG-PCL Diblock Copolymer as an in Situ Gel-Forming Carrier," Biomacromolecules, Apr. 2007, 8(4):1093-100.
Inaoka et al., "Local application of hepatocyte growth factor using gelatin hydrogels attenuates noise-induced hearing loss in guinea pigs," Acta Otolaryngol., Apr. 2009, 129(4):453-7.
International Preliminary Report on Patentability in International Appln. No. PCT/US2019/063418, mailed on Jun. 10, 2021, 9 pages.
International Search Report and Written Opinion in International Appln. No. PCT/US2019/063418, mailed on Apr. 23, 2020, 12 pages.
Invitation to Pay Additional Fees and, Where Applicable, Protest Fee in International Appln. No. PCT/US2019/063418, mailed on Feb. 24, 2020, 2 pages.
Jacques et al., "A dual function for canonical Wnt/beta-catenin signaling in the developing mammalian cochlea," Development, Dec. 2012, 139(23):4395-4404, 18 pages.
Jaenisch and Bird, "Epigenetic regulation of gene expression: how the genome integrates intrinsic and environmental signals," Nat Genet, Mar. 2003, 33 Suppl:245-254.
Jorstad et al., "Stimulation of functional neuronal regeneration from Müller glia in adult mice," Nature, Aug. 2017, 548(7665):103-107.
Kearns et al., "Functional annotation of native enhancers with a Cas9-histone demethylase fusion," Nat Methods, 2015, 12:401-403, 6 pages.
Kerenyi et al., "Histone demethylase LSD1 represses hematopoietic stem and progenitor cell signatures during blood cell maturation," eLife, 2013, 2:e00633, 23 pages.
Koch et al., "The landscape of histone modifications across 1% of the human genome in five human cell lines," Genome Res, 2007, 17(6):691-707.
Laurent et al., "A specific LSD1/KDM1A isoform regulates neuronal differentiation through H3K9 demethylation," Mol Cell, Mar. 2015, 57(6):957-970.
Lei et al., "Lysine-specific demethylase 1 promotes the sternness and chemoresistance of Lgr5(+) liver cancer initiating cells by suppressing negative regulators of beta-catenin signaling," Oncogene, Jun. 2015, 34(24):3188-98.
Loo et al., "From short peptides to nanofibers to macromolecular assemblies in biomedicine," Biotechnol Adv., 2012, 30(3):593-603.
Love et al., "Moderated estimation of fold change and dispersion for RNA-seq data with DESeq2," Genome Biol, 2014, 15(12):550, 21 pages.
Maiques-Diaz et al., "Enhancer Activation by Pharmacologic Displacement of LSD1 from GFI1 Induces Differentiation in Acute Myeloid Leukemia," Cell Rep, Mar. 2018, 22:3641-3659, 40 pages.
Maru et al., "Lentivirus-Based Stable Gene Delivery into Intestinal Organoids," Methods Mol Biol, 2016, 1422:13-21.
Metzger et al., "LSD1 demethylates repressive histone marks to promote androgen-receptor-dependent transcription," Nature, Sep. 2005, 437(7057):436-439, 5 pages.
Moore et al., "Modulation of Wnt Signaling Through Inhibition of Secreted Frizzled-Related Protein I (sFRP-1) with N-Substituted Piperidinyl Diphenylsulfonyl Sulfonamides," J Med.Chem., 2009, 52(1):105-116.
Ocampo et al., "In Vivo Amelioration of Age-Associated Hallmarks by Partial Reprogramming," Cell, Dec. 2016, 167(7):1719-1733. e12, 28 pages.
Orford et al., "Differential H3K4 methylation identifies developmentally poised hematopoietic genes," Dev Cell, May 2008, 14(5):798-809.
Pan et al., "Understanding the evolution and development of neurosensory transcription factors of the ear to enhance therapeutic translation," Cell Tissue Res, Jun. 2012, 349:415-432.

(56) References Cited

OTHER PUBLICATIONS

Park et al., "H3K27 Demethylase JMJD3 Employs the NF-kappaB and BMP Signaling Pathways to Modulate the Tumor Microenvironment and Promote Melanoma Progression and Metastasis," Cancer Res, Jan. 2016, 76(1):161-170.
Patel et al., "The histone demethylase LSD1 regulates inner ear progenitor differentiation through interactions with Pax2 and the NuRD repressor complex," PLoS One, Jan. 2018, 13(1):e0191689, 20 pages.
Paulson et al., "A Novel Controlled Local Drug Delivery System for Inner Ear Disease," Laryngoscope, Apr. 2008, 118(4):706-11.
Piu et al., "OTO-104: A Sustained-Release Dexamethasone Hydrogel for the Treatment of Otic Disorders," Otol Neurotol., Jan. 2011, 32(1):171-9.
Railo et al., "Genomic response to Wnt signalling is highly context-dependent—evidence from DNA microarray and chromatin immunoprecipitation screens ofWnt/TCF targets," Exp Cell Res, Oct. 2009, 315(26):2690-2704.
Sakamoto et al., "Inner ear drug delivery system from the clinical point of view," Acta Otolaryngol Suppl., Nov. 2010, 563:101-4.
Samarajeewa et al., "Transcriptional response to Wnt activation regulates the regenerative capacity of the mammalian cochlea," Development, Nov. 2018, 145(23):dev166579, 27 pages.
Stojanova et al., "Epigenetic regulation of Atoh1 guides hair cell development in the mammalian cochlea," Development, 2015, 142(20):3529-3536.
Subramanian et al., "Gene set enrichment analysis: a knowledge-based approach for interpreting genome wide expression profiles," PNAS, Oct. 2005, 102(43):15545-15550.
Sun et al., "Histone demethylase LSD1 regulates neural stem cell proliferation," Mol Cell Biol, Apr. 2010, 30(8): 1997-2005.
Tamura et al., "Drug Delivery to the Cochlea Using PLGA Nanoparticles," Laryngoscope, Nov. 2005, 115(11):2000-5.
Wang et al., "Dose-dependent sustained release of dexamethasone in inner ear cochlear fluids using a novel local delivery approach," Audiol Neurootol., 2009, 14(6):393-401.
Wang et al., "LSD1 co-repressor Rcor2 orchestrates neurogenesis in the developing mouse brain," Nat Commun, Jan. 2016, 7:10481, 14 pages.
Wang et al., "Principles of inner ear sustained release following intratympanic administration," Laryngoscope, Feb. 2011, 121(2):385-91.
Watanabe et al., "Conditioned mesenchymal stem cells produce pleiotropic gut trophic factors," J Gastroenterol, 2014, 49:270-282, 13 pages.
Web.Stanford.Edu [online], "Wnt Target genes," 2018, retrieved on Sep. 9, 2022, retrieved from URL<web.stanford.edu/group/nusselab/cgi-bin/wnt/target_genes>, 4 pages.
Whyte et al., "Enhancer decommissioning by LSD1 during embryonic stem cell differentiation," Nature, Feb. 2012, 482(7384):221-225.
Wu et al., "A systematic survey of carbonic anhydrase mRNA expression during mammalian inner ear development," Dev Dyn, Mar. 2013, 242(3):269-280.
Yamada et al., "Rest promotes the early differentiation of mouse ESCs but is not required for their maintenance," Cell Stem Cell, Jan. 2010, 6(1):10-15.
Zhou et al., "Nuclear GSK3β promotes tumorigenesis by phosphorylating KDM1A and inducing its deubiquitylation by USP22," Nat Cell Biol, Sep. 2016, 18(9):954-966, 28 pages.

Zibetti et al., "Alternative splicing of the histone demethylase LSD1/KDM1 contributes to the modulation of neurite morphogenesis in the mammalian nervous system," J Neurosci, Feb. 2010, 30(7):2521-2532.
Notice of Allowance in Japanese Appln. No. 2018-540010, dated Apr. 18, 2022, 6 pages (with English translation).
Costa et al., "Atoh1 in sensory hair cell development: constraints and cofactors," Seminars in Cell & Developmental Biology, May 2017, 65:60-68.
Office Action in Japanese Appln. No. 2022-069599, dated Jun. 6, 2023, 3 pages (with English translation).
Agrup et al., "The inner ear and the neurologist," J Neurol Neurosurg Psychiatry, Feb. 2007, 78(2):114-22.
Arnold et al., "Sox2+ adult stem and progenitor cells are important for tissue regeneration and survival of mice," Cell Stem Cell, Oct. 2011, 9(4):317-29.
Cohen-Salmon et al., "Targeted ablation of connexin26 in the inner ear epithelial gap junction network causes hearing impairment and cell death," Curr Biol., Jul. 2002, 12(13):1106-11.
Elgoyhen and Franchini, "Prestin and the cholinergic receptor of hair cells: positively-selected proteins in mammals," HHS Public Access Author Manuscript, doi: 10.1016/j.heares.2009.12.028, published online Jan. 6, 2010, published in final edited form as: Hear Res, Mar. 2011, 273(1-2):100-8, 19 pages.
Fritzsch et al., "The molecular basis of neurosensory cell formation in ear development: a blueprint for hair cell and sensory neuron regeneration?," Bioessays, Dec. 2006, 28(12):1181-93, 13 pages.
Fujioka et al., "Generating mouse models of degenerative diseases using cre/lox-mediated in vivo mosaic cell ablation," J Clin Invest, Jun. 2011, 121(6):2462-9.
Harding et al., "The effect of an age-related hearing loss gene (Ah1) on noise-induced hearing loss and cochlear damage from low-frequency noise," Hear Res, Jun. 2005, 204(1-2):90-100, 5 pages (Abstract only).
Hudspeth, "Making an effort to listen: mechanical amplification in the ear," Neuron, Aug. 2008, 59(4):530-45.
Kujawa and Liberman, "Conditioning-related protection from 15 acoustic injury: effects of chronic deefferentation and sham surgery," J Neurophysiol, Dec. 1997, 78(6):3095-106.
Löwenheim et al., "Gene disruption of $p27^{Kip1}$ allows cell 15 proliferation in the postnatal and adult organ of corti," Proc Natl Acad Sci U S A, Mar. 1999, 96(7):4084-8.
Maison et al., "Loss of αCGRP reduces sound-evoked activity in the cochlear nerve," J Neurophysiol, Nov. 2003, 90(5):2941-9.
Mantela et al., "The retinoblastoma gene pathway regulates the postmitotic state of hair cells of the mouse inner ear," Development, May 2005, 132(10):2377-2388.
Martinez-Monedero et al., "Differentiation of inner ear stem cells to functional sensory neurons," Dev Neurobiol., Apr. 2008, 68(5):669-684.
Muzumdar et al., "A global double-fluorescent Cre reporter mouse," Genesis, Sep. 2007, 45(9):593-605.
Nayak et al., "Development of the hair bundle and mechanotransduction," Int J Dev Biol., 2007, 51(6-7):597-608.
Richardson et al., "How the genetics of deafness illuminates auditory physiology," Annu Rev Physiol., 2011, 73:311-34.
Sage et al., "Essential role of retinoblastoma protein in mammalian hair cell development and hearing," Proc Natl Acad Sci U S A, May 2006, 103(19):7345-50.
Sage et al., "Proliferation of functional hair cells in vivo in the absence of the retinoblastoma protein," Science, Feb. 2005, 307(5712):1114-8.
Warchol, "Sensory regeneration in the vertebrate inner ear: Differences at the levels of cells and species," Hear Res, Mar. 2011, 273(1-2):72-9, 5 pages (Abstract only).

* cited by examiner

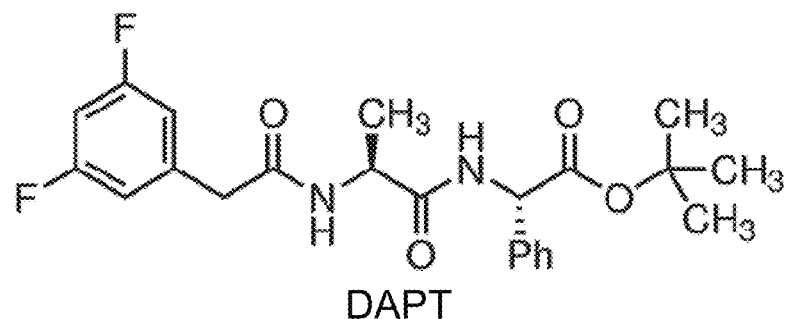
DAPT
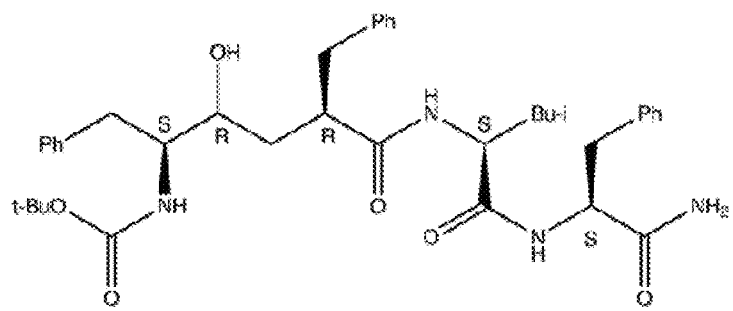
L-685,458
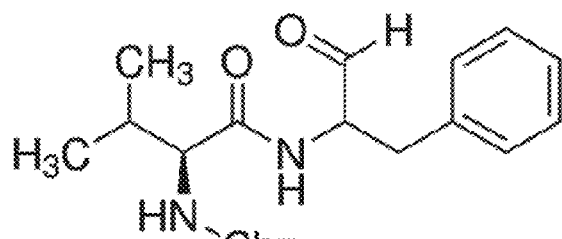
MDL 28170
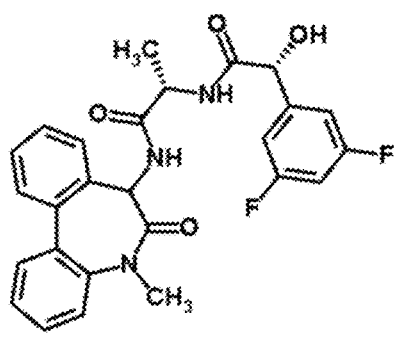
LY-411575
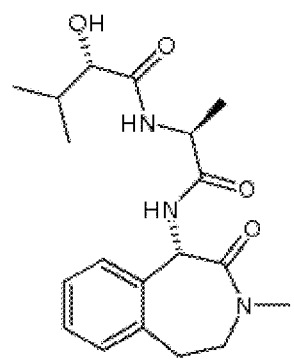
Semagacestat (LY450139)
FIG. 10A

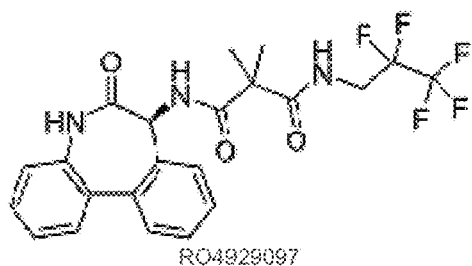
RO4929097
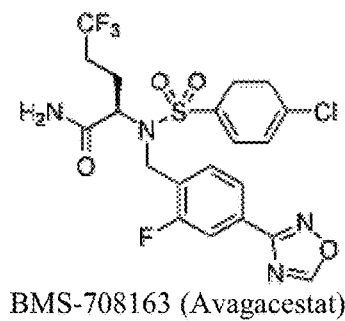
BMS-708163 (Avagacestat)
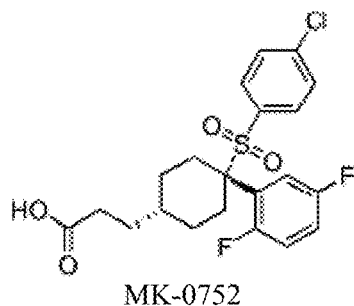
MK-0752
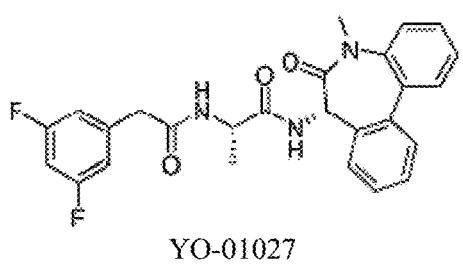
YO-01027
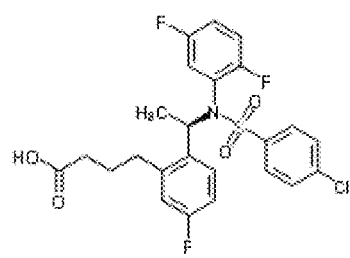
BMS 299897
FIG. 10B

TREATING HEARING LOSS

CLAIM OF PRIORITY

This application is a continuation of U.S. patent application Ser. No. 16/007,586, filed Jun. 13, 2018, which is a continuation of U.S. patent application Ser. No. 14/426,629, filed Mar. 6, 2015, which is the National Stage of International Application Serial No. PCT/US2013/058446, filed Sep. 6, 2013, which claims the benefit of U.S. Provisional Application Ser. No. 61/698,475, filed on Sep. 7, 2012. The entire contents of the foregoing are incorporated herein by reference.

FEDERALLY SPONSORED RESEARCH OR DEVELOPMENT

This invention was made with Government support under Grant Nos. RO1 DC007174, R21 DC010440-01 and P30 DC05209 awarded by the National Institutes of Health. The Government has certain rights in the invention.

TECHNICAL FIELD

This invention relates to methods for treating hearing loss associated with loss of cochlear hair cells, e.g., caused by noise exposure, in post neonatal animals, e.g., adolescent or adult animals, using certain Notch inhibitors, e.g., gamma secretase inhibitors.

BACKGROUND

The cochlear sensory epithelium contains hair cells adapted for the detection of sound, which is transduced by stereocilia at their apical surfaces (1, 2). Hair cells produced during development are post-mitotic and are not replaced after loss (3-6) or as part of normal cell turnover in mammals (7-9). As a result, deafness due to hair cell loss is irreversible. Hair cell development during the embryonic period includes a complex series of fate decisions, in which prosensory epithelial cells acquire different fates, either hair cell or supporting cell, through a process of lateral inhibition which is mediated by Notch signaling (5, 10, 11). Supporting cells are prevented from differentiating into hair cells by active Notch signaling stimulated by ligands on adjacent hair cells. This active Notch signaling ends shortly after birth, given the loss of an effect of γ-secretase inhibitors on hair cell number in the early postnatal period (13) and other data suggesting that Notch signaling is extinguished after birth (14).

SUMMARY

Hearing loss due to damage to auditory hair cells is normally irreversible because mammalian hair cells do not regenerate after the newborn period. At least in part, the present invention is based on the discovery that blocking Notch signaling with certain gamma-secretase inhibitors resulted in regeneration of cochlear hair cells in adult animals that correlated with recovery of hearing after noise-induced hearing loss.

Thus, in one aspect the invention features methods for treating hearing loss caused by loss of cochlear hair cells in a post-neonatal mammal. The methods include systemically or locally administering to the ear of the mammal a composition comprising a therapeutically effective amount of a Notch inhibitor, e.g., a gamma secretase inhibitor, wherein the therapeutically effective amount is an amount sufficient to restore hearing at one or more frequencies.

In some embodiments, the hearing loss was caused by exposure to a physical or chemical ototoxic insult, e.g., repeated (chronic) exposure or one or more acute exposures.

In some embodiments, the physical ototoxic insult is noise.

In some embodiments, the composition is administered to the ear within four weeks, two weeks, one week, or one day of the exposure to the insult.

In some embodiments, the composition is applied topically to the round window.

In some embodiments, the composition further comprises a carrier, e.g., a sustained release carrier. In some embodiments, the carrier is a polyoxyethylene-polyoxypropylene triblock copolymer.

In some embodiments, the composition comprises at least 10 mM of the Notch inhibitor.

In some embodiments, the methods further include determining a baseline level of hearing at one or more frequencies before administering the composition, and a subsequent level of hearing at the same one or more frequencies after administering the composition, and administering one or more additional doses of the composition until a desired level of hearing at the one or more frequencies is recovered. In some embodiments, the subsequent level of hearing is determined one week, two weeks, three weeks, one month, two months, three months, four months, six months, and/or twelve months after administering the composition.

In some embodiments, the gamma secretase inhibitor is selected from the group consisting of RO4929097; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide, see U.S. Pat. No. 6,541,466); ELN-46719 (2-hydroxy-valeric acid amide analog of LY411575 (where LY411575 is the 3,5-difluoro-mandelic acid amide) (U.S. Pat. No. 6,541,466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl) pentanamide, Samon et al., Mol Cancer Ther 2012; 11:1565-1575); Compound E ((2S)-2-{[(3,5-Difluorophenyl)acetyl] amino}-N-[(3S)-1-methyl-2-oxo-5-phenyl-2,3-dihydro-1H-1,4-benzodiazepin-3-yl]propanamide; see WO 98/28268 and Samon et al., Mol Cancer Ther 2012; 11:1565-1575); and Semagacestat (LY450139; (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide), or pharmaceutically acceptable salts thereof.

In some embodiments, the gamma secretase inhibitor is LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide).

In some embodiments, the post-neonatal mammal is a child, adolescent or adult, e.g., above the age of 6 months, 1, 2, 3, 4, 5, 6, 7, 8, 9, 10, 11, 12 or 13 years.

In some embodiments, the mammal is an adult of at least 40 years of age, e.g., at least 45, 50, 55, 60, 65, 70 years of age.

In some embodiments, the mammal is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

(B) Ratio of myosin VIIa (labels hair cells) to Hoechst-positive cells induced by LY411575 was calculated relative to DMSO-treated spheres from organ of Corti.

(C) Explant cultures of the organ of Corti from P1 mice cultured for 72 h in the presence of DMSO or LY411575 (1 μM) had ectopic hair cells (myosin VIIa; light grey (green in original) in top row of images) in the outer hair cell region (white bracket). Ectopic hair cells were positive for phalloidin (labels the hair bundle and cuticular plate; shown in light grey (red in original) in middle row of images). Inset is a high-power view (scale bar is 2 μM) of a phalloidin-stained hair cell showing bundle structure.

(D) An increase in myosin VIIa-positive cells per 100 μm of the cultured organ of Corti explants from P1 mice was found 72 h after LY411575 treatment.

In all graphs, error bars show the standard error of the mean. Scale bar is 50 μm.

FIGS. 2A-D. Hair cell replacement after LY411575 treatment of organ of Corti explants from mice subjected to ablation of hair cells (A) Hair cells can be seen throughout the neonatal organ of Corti in a whole mount labeled for myosin VIIa.

(B) Three rows of outer (white bracket; OHC1-3) and one row of inner hair cells (IHC) can be seen in a P3 organ of Corti explant after staining for myosin VIIa. Deiters' cells (DC1-3) and Hensen cells (HC) in the outer hair cell region are positive for Sox2.

(C) Organ of Corti explants from Pou4f3-Cre; Mos-iCsp3 double-transgenic mice subjected to dimerizer-induced hair cell ablation and cultured for 3 d in the presence of LY411575 had an increased number of myosin VIIa-positive cells in the outer hair cell region (white bracket) compared to the carrier-treated explant. The same region had a decreased number of Sox2-positive cells relative to the control. A high power view (scale bar, 2 μM) of phalloidin-stained tissue shows the hair cell stereociliary bundles (inset).

(D) The number of outer hair cells at the mid-apex and mid-base was increased in the LY411575 treated as compared to the control cochleae in the hair cell-ablated samples (Csp Tg). Increased numbers of hair cells were also seen after LY411575 treatment of wild-type organ of Corti (Wt) at the apex, mid-apex and mid-base. In both cases the increase in the number of hair cells was accompanied by a decrease in the number of supporting cells.

The error bars are standard error of the mean (n=7 in each group). Asterisks indicate $p<0.05$. All scale bars are 50 μm.

Figure 3:
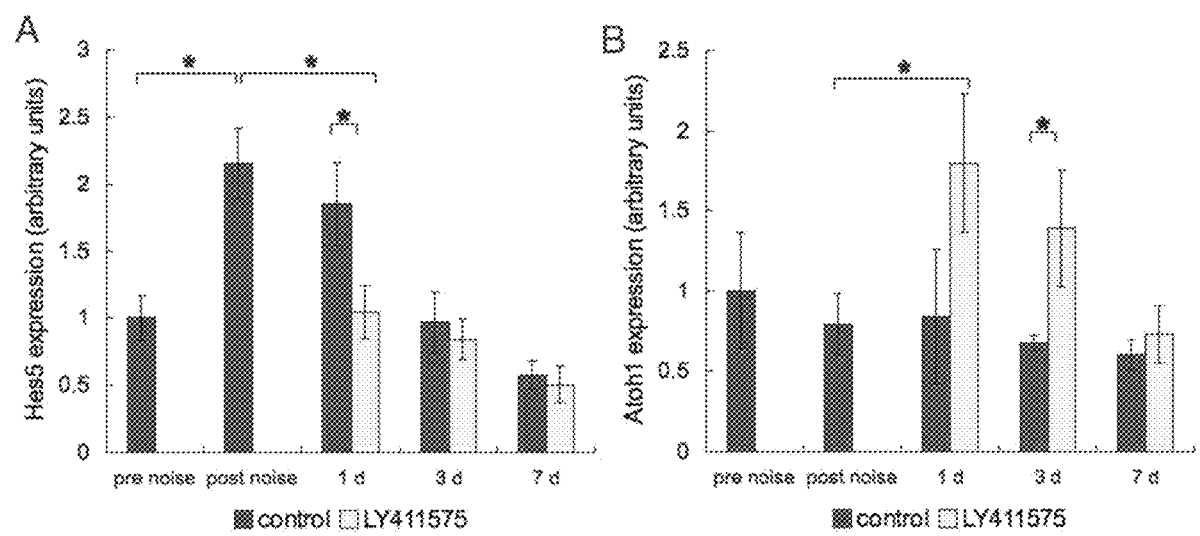

FIGS. 3A-B. Time course of Hes5 and Atoh1 mRNA expression in the cochlea with or without LY411575 after noise exposure (A) Elevated levels of Hes5 after noise exposure were diminished in response to LY411575 treatment and reached the pre noise level. Without inhibitor, expression levels of Hes5 in the cochlea increased 1 d after noise exposure and remained elevated compared to the pre noise level for up to 2 d. Samples for qRT-PCR were taken before exposure to noise (pre noise), at the time (day 0) of drug treatment (post noise), at day 1 of drug treatment (d 1), day 3 of drug treatment (d 3), and day 7 of drug treatment (d 7). mRNA expression levels were calculated relative to the pre-noise level.

(B) Treatment with LY411575 significantly increased the expression of Atoh1 compared to the opposite, untreated ear 1 d after noise exposure. Increased levels were detected 1 d after drug treatment (d 1) and remained elevated 3 d after drug treatment (d 3; n=9 in each group).

Error bars are standard error of the mean. Asterisks indicate $p<0.05$.

FIGS. 4A-G. Lineage tracing of supporting cells in noise-exposed cochleae treated in vivo with a γ-secretase inhibitor (A) Double-labeled cells (arrowheads) positive for Sox2 lineage (GFP) and myosin VIIa (blue in original) were observed in the outer hair cell area (white bracket) in cochlear tissues from deafened mice carrying the Sox2-CreER as well as the Cre reporter transgene, mT/mG, 1 month after LY411575 treatment. Hair cell co-labeling with the lineage tag indicates derivation from a Sox2-positive cell and is thus evidence for regenerated hair cells after deafening in the mature mouse cochlea by transdifferentiation of supporting cells. These confocal xy-projection images of LY411575-treated ears from Sox2-CreER; mT/mG double transgenic mice are in the 8 kHz area of the cochlear longitudinal frequency map.

(B) Confocal xz-projections from the same area as A show that myosin VIIa-positive cells in the medial part of the outer hair cell area (white bracket) had GFP-positive hair bundle structures, indicating a Sox2 lineage (arrowhead). The cell shown was attached to the basement membrane (arrow) similar to a supporting cell.

(C) Cells double-labeled for myosin VIIa (blue in original) and Sox2 lineage (green in original) were observed (arrowheads) in the outer hair cell area (white bracket) in the 11.3 kHz region in this xy projection from a deafened cochlea 1 month after LY411575 treatment. Original hair cells have red (in original) hair bundles and new, Sox2-lineage hair cells have green (in original; GFP-positive) bundles. The higher power view (inset, scale bar is 2 μM) shows hair cells with their original (red in original) bundles adjacent to cells derived from Sox2-positive cells (bundles, green in original).

(D) Cross section from the same area as C show that myosin VIIa-positive cells in the outer hair cell area (white bracket) had GFP-positive hair bundle structures. The cell shown is attached to the basement membrane (arrow). Note position of the nucleus close to the basement membrane.

(E) No double-labeled cells were found in the xy-projection images from the control (contralateral to A) ear in the 8 kHz area. White bracket shows the outer hair cell region.

(F) xz-projections confirm the lack of double-labeled hair cells in the control, contralateral ear.

All scale bars are 50 µm.

(G) Quantification of the GFP (Sox2 lineage) and myosin VIIa double-labeled cells in the outer hair cell region 1 month after treatment with LY411575 in deafened mice at frequency-specific cochlear areas (n=5 in each group). Error bars are standard error of mean.

Figure 5:
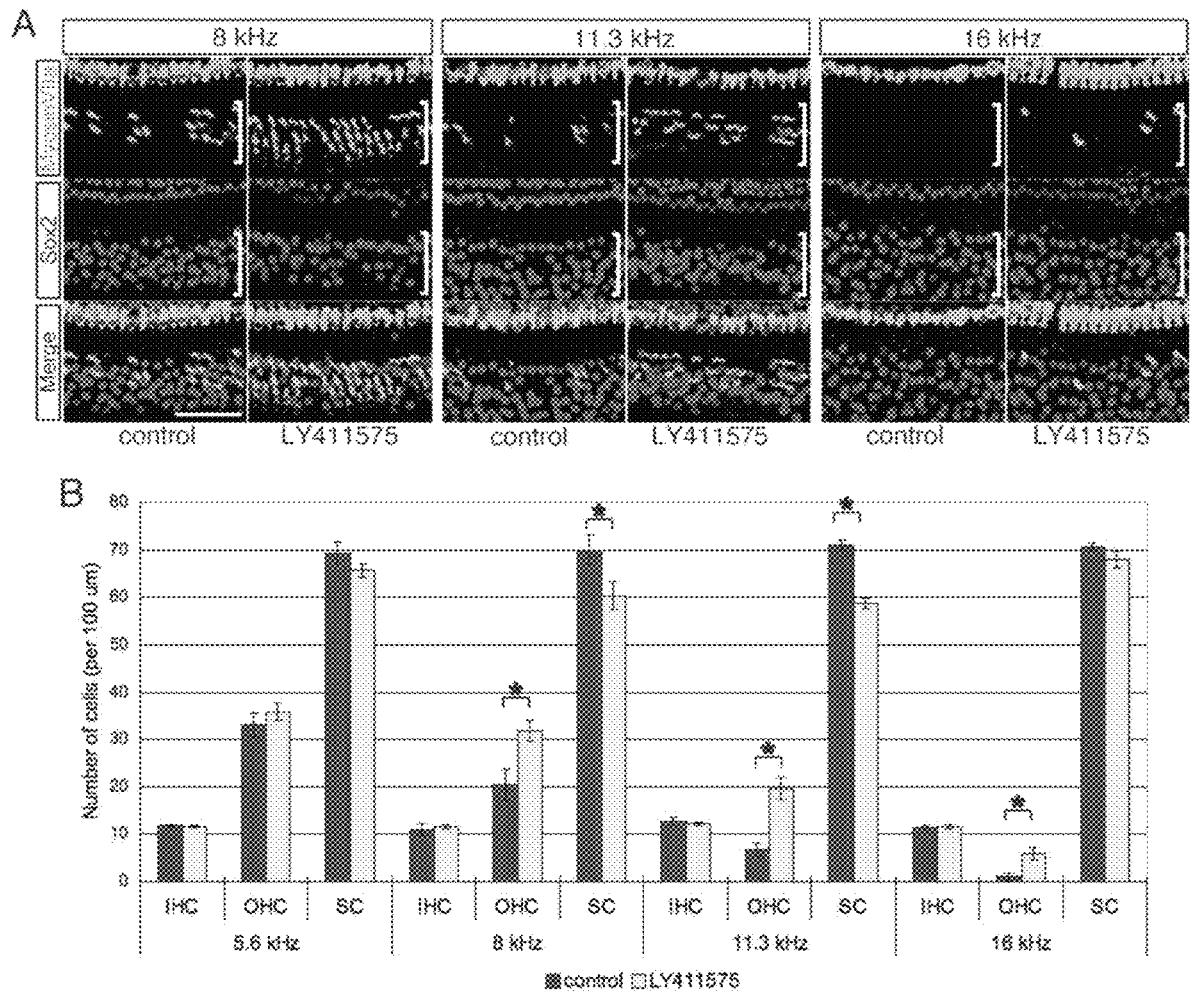

FIGS. 5A-B. Hair cells in damaged mature cochlea treated with LY411575 in vivo (A) The number of hair cells (green in original; myosin VIIa) in the outer hair cell region (white brackets) of deafened cochleae at 8, 11.3, and 16 kHz areas was increased compared to the control ear (right ear treated with carrier) 3 months after treatment with LY411575 (left ear), and the increase was accompanied by a decrease in the number of supporting cells (blue in original: Sox2) in the same regions in these whole mount confocal xy-projections.

(B) Significant differences in the numbers of hair cells and supporting cells were observed in the outer hair cell area at 8 and 11.3 kHz regions of treated (left) ears 3 months after treatment with LY411575 as compared to the values in the contralateral carrier-treated ear of deafened mice (n=5 in each group).

All scale bars are 50 µm. Error bars are standard error of the mean and asterisks indicate p<0.05.

FIGS. 6A-E. Measurement of ABR in deafened ears after LY411575 treatment (A, B) A decrease in ABR thresholds at low frequencies (up to 16 kHz) in the left, LY411575-treated ear (B) compared to the right, control ear (A) was apparent in ABR thresholds in recordings made at 7 frequencies from 5.66 to 45.25 kHz with the following time course. Before noise exposure (Pre Noise: open circles), 1 d after noise exposure (Post Noise: filled circles), 1 week after drug treatment (1 W: open squares), 1 month after treatment (1 Mo: crosses), and 3 months after treatment (3 Mo: filled triangles) (n=5 in each group). When no response was observed at 80 dB (maximum acoustic output of the system) the threshold was designated as 85 dB.

(C) An example of 8 kHz ABR waves recorded 3 months after drug treatment from the same mouse. Arrowheads show the peaks with the largest peak-to-peak amplitude. In the LY411575-treated ear, the peak could first be detected at 65 dB, while on the control side the peak could first be detected at 75 dB.

(D, E) The differences in threshold (D) and wave I amplitude (E) 3 months after drug treatment compared to 1 d after noise exposure between control and LY411575-treated ears at 8, 11.33, and 16 kHz (asterisks) were significant (n=5 in each group).

Error bars are standard error of the mean.

Figure 7:
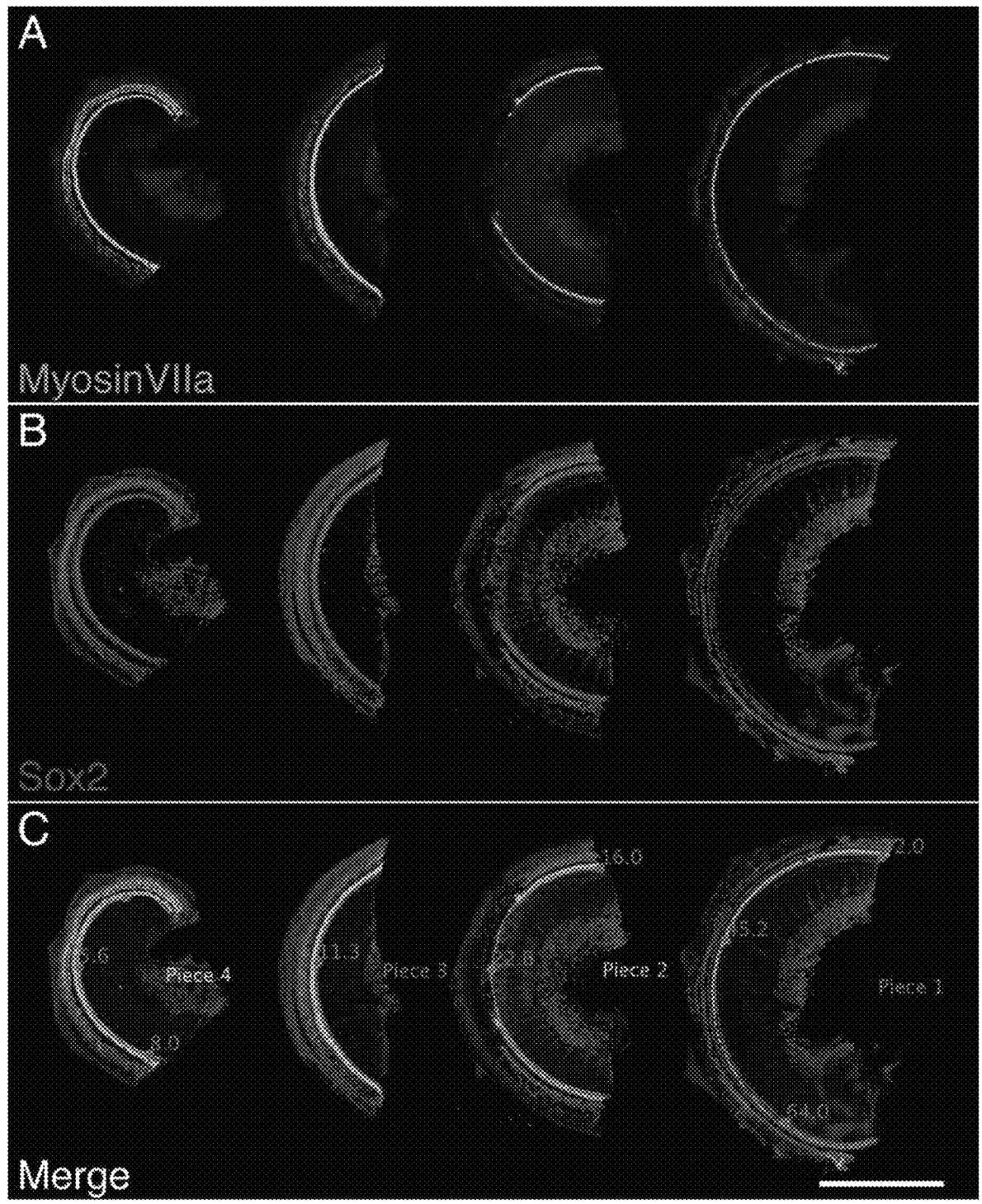

FIGS. 7A-C. Cochlear architecture in a mouse exposed to 8-16 kHz octave-band noise at 116 dB SPL for 2 h (A) The loss of hair cells (myosin VIIa) was apparent throughout the cochlea with the greatest loss seen in outer hair cells as well as a loss of inner hair cells in the 22 kHz region.

(B) At this noise exposure intensity loss of hair cells was accompanied by preservation of supporting cells (Sox2) in most of the cochlea, with the exception of the 22 kHz region, where inner hair cell damage was also seen.

(C) Merged images show the base (Piece 1), mid-base (Piece 2), mid-apex (Piece 3), and apex (Piece 4) and the corresponding frequencies.

Scale bar is 500 µm.

Figure 8:
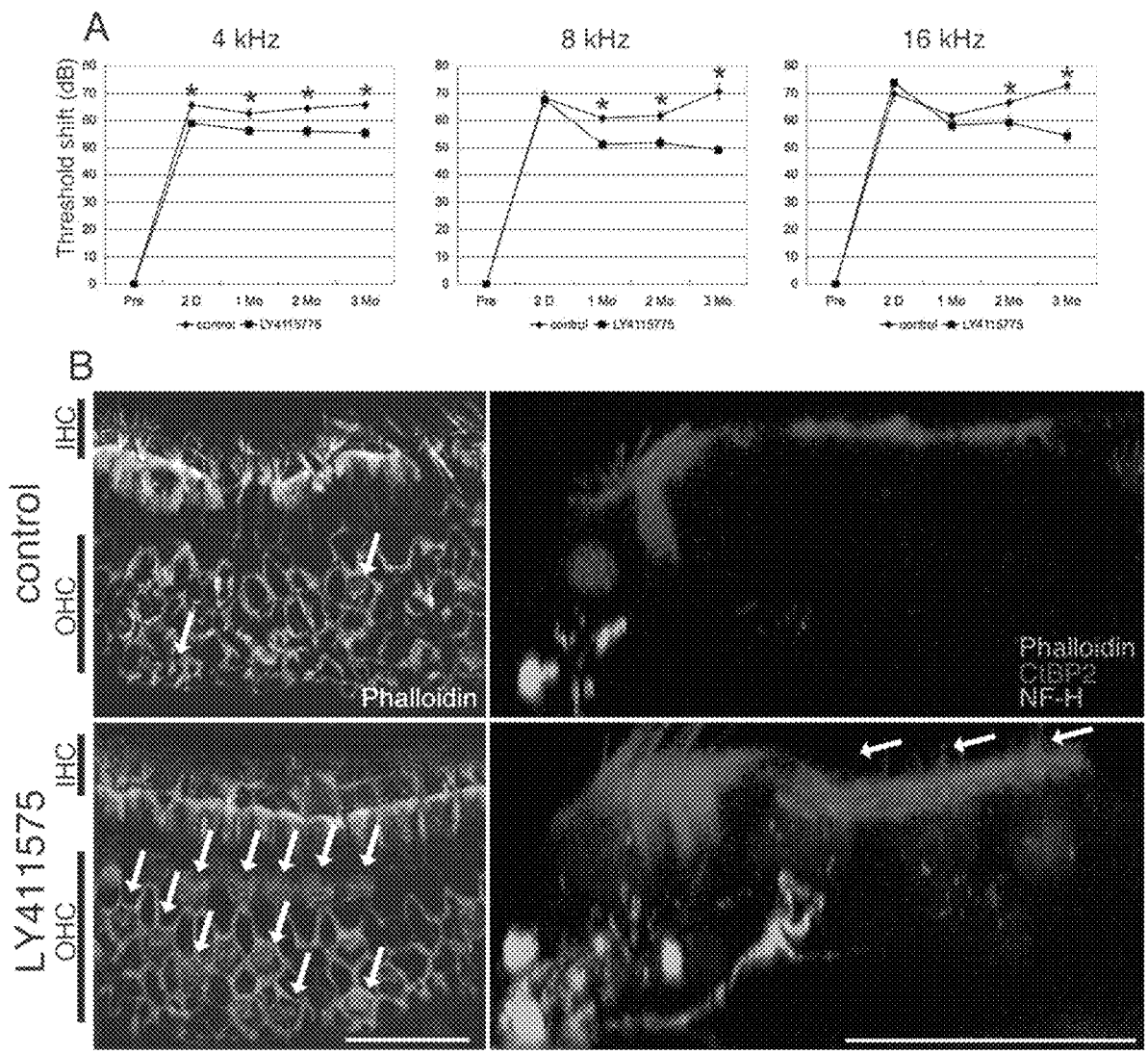

FIGS. 8A-B. Analysis of the effect in vivo on the brainstem response and hair cell morphology of LY411575 administered systemically to young adult noise-damaged mice (A) Treatment with LY411575 by injection intraperitoneally at 50 mg/kg daily for 5 d increased the responsiveness of the ear at low frequency after 2-4 months. Significant improvements in threshold of the ABR were found between 1 and 3 months at 4, 8 and 16 kHz.

(B) Stereociliary bundles could be detected on hair cells after phalloidin staining (white arrows). Cells stained for myosin VIIa were increased in the apex of the cochlea where outer hair cell loss was incomplete.

Asterisks indicate p<0.05. Scale bars are 50 µm.

Figure 9:
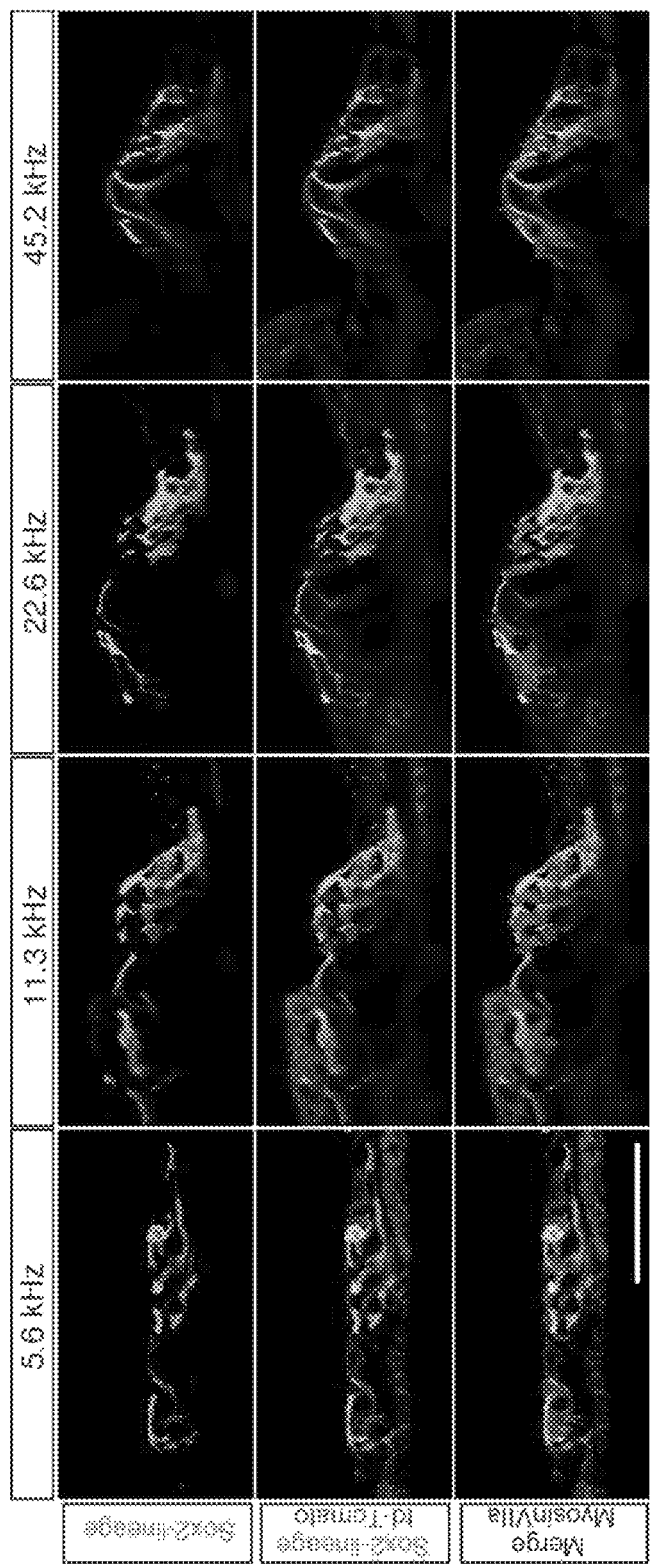

FIG. 9. Labeling of a mature mouse cochlea with the reporter strain

The Sox2-CreER mouse crossed to the reporter line, mT/mG, treated with tamoxifen at P1 was examined as a whole mount after dissection. Any cells that express Sox2 at P1 would be expected to be GFP-positive after removal of the STOP sequence, whereas cells that do not will retain the tomato label. Supporting cells from the 5 to the 45 kHz regions are labeled by GFP from the Sox2-Cre reporter (Sox2-lineage; green in original). In contrast, myosin VIIa-labeled hair cells (blue in original) display td-Tomato labeling (td-Tomato; red in original), and this pattern is retained from the 5 to the 45 kHz region (see bundles in the merged image; Merge). Note that some pillar cells are not labeled by the GFP from the reporter (22.6 kHz for example), presumably due to incomplete Cre activity.

Scale bar is 50 µm.

FIGS. 10A-B. Structures of Gamma-Secretase Inhibitors.

The structures of DAPT (N-[(3,5-Difluorophenyl)acetyl]-L-alanyl-2-phenyl]glycine-1,1-dimethylethyl ester), L-685458 ((5S)-(t-Butoxycarbonylamino)-6-phenyl-(4R) hydroxy-(2R)benzylhexanoyl)-L-leu-L-phe-amide), BMS-708163 (Avagacestat); MK-0752; YO-01027; MDL28170 (Sigma), LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide), and Semagacestat (LY450139; (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide) are shown.

DETAILED DESCRIPTION

The generation of physiologically active hair cells in an adult mammal has been a sought-after but elusive goal. Transfection of bHLH transcription factor, Atoh1, which drives hair cell differentiation during development, is one approach that increases hair cell number in embryonic or newborn tissue, but cells that were competent to become hair cells in the embryo lost their responsiveness as the animal matured (13, 17, 26). Delivery of Atoh1 in an adenovirus to the damaged, adult cochlea (16) showed some hair cell differentiation, but the number of new hair cells was not clear and new hair cells could not be traced from their precursors, making it difficult to distinguish between "new" hair cells and hair cells that had recovered from trauma due to a toxin or noise damage. Stimulation of cell division by silencing cell cycle inhibitors has been suggested as an alternative route to hair cell regeneration (6), but hair cells, due to their highly differentiated state, tend to activate suicide programs after they divide and proliferation can cause deafness (3, 27, 28). Regeneration of hair cells is made difficult by the cellular organization of the cochlea: minute changes in the interactions between cells of the epithelium are a cause of deafness (29). Tight junctions are required for maintaining the ionic milieu of endolymph that bathes the surface of hair cells, and the flexibility and spacing of outer hair cells has an impact on the function of the cochlear amplifier, which is achieved by outer hair cell contraction, and together with sound detection by the transduction apparatus of inner hair cells, accounts for the sensitivity and broad dynamic range of mammalian hearing (1, 30, 31).

The present inventors had recently shown that inhibition of Notch increased hair cell differentiation from stem cells and that the mechanism was dependent on Atoh1, since silencing the transcription factor in the γ-secretase inhibitor-treated stem cells prevented the induction of hair cell fate (15). As described herein, inner ear stem cells were used to select a potent γ-secretase inhibitor. The Notch pathway was targeted, as a strategy that would only be effective on cells that were actively signaling through Notch. Although increased Notch signaling in the adult after damage had been suggested by some (12), the loss of an effect of γ-secretase inhibitors on hair cell number in the early postnatal period (13) and data suggesting that Notch signaling was extinguished after birth (14) both suggested that γ-secretase inhibitors would have no effect on hair cell number in the adult mammalian cochlea. Thus, treating hearing loss by generating new hair cells would be difficult, particularly in light of the failures of previous attempts to make new hair cells by manipulating the cell cycle or by Notch gene knockouts in the embryo, which lead to the presence of large numbers of extra hair cells—but deaf animals, as the supernumerary hair cells are not functional and can in fact damage the structures of the inner ear.

Surprisingly, as described herein, inhibition of Notch after noise damage leads to recovery of hearing ability; without wishing to be bound by theory, it is believed that this occurs by transdifferentiation of supporting cells into hair cells in post-neonatal animals. The basal location of the nucleus in the new hair cells was consistent with derivation from supporting cells, which are normally located in a plane below that of the hair cells. Supporting cell transdifferentiation was induced by Atoh1, which may be acting in a similar capacity to transcription factors, some of which are somewhat related to Atoh1, that allow cellular reprogramming and transdifferentiation to neurons (32, 33). The supporting cells express stem cell markers such as Sox2, Musashi1, and GLAST (34-36) and have the capacity for proliferation and transdifferentiation for a short period postnatally (26). Capacity for neurosphere formation by the sensory epithelial cells in the cochlea is found in a similar postnatal time frame (37).

Drug therapy for restoration of hair cells is a new approach and delivery to the inner ear fluids without actual injection into the cochlea may be an advantage over gene therapy and may also effectively restrict hair cell differentiation to cells in the sensory epithelial area as compared to gene therapy that may convert hair cells in a broader area. A middle ear approach was used for the delivery of LY411575 to the damaged inner ear; surprisingly, this route allowed delivery of a sufficient dose to have a therapeutic effect. Since the round window membrane consists of cell layers, lipid solubility of the drug favors permeability (23, 24).

Surprisingly, though previously it would have been predicted that the new cells would die, recovery lasted for at least 3 months, the longest time point measured.

Novel approaches using inner ear stem cells and transgenic mice were critical for the present demonstration that hair cells could regenerate in the mouse. The caspase-3 mouse provided a model in which hair cells could be selectively deleted without damage to other cells so that new hair cells could be accurately quantified. Lineage tracing with the mT/mG; Sox2-CreER double transgenic mouse allowed the unambiguous demonstration that drug treatment resulted in the generation of new hair cells and not recovery of hair cell bundles that could have accounted for recovery in the absence of lineage tracing. Improved thresholds were found by ABR, showing that hearing was improved by γ-secretase inhibitor administration in the acute damage situation. Hair cell counts showed an increase in the same frequency regions as the improved ABR. Thus the frequency specificity of the improved hearing was used to determine the correlation between the gain in hair cell number and the improved hearing threshold. The damage in the acute noise exposure model reflected hair cell loss in humans, most severe in the base and restricted primarily to the outer hair cells (22). The improvement in threshold at the apex of the cochlea was thought to result from an increase in the number of hair cells to a level that produced a detectable change through outer hair cell activity. As a result of the greater damage at the base of the cochlea, the number of hair cells at the base was not adequate to lower the threshold of the ABR, and the increase in hair cells in the apex could not be detected by a change in DPOAE threshold. The combined physiological and cellular evidence allowed a definitive proof of the regeneration of hair cells that was quantitative, was correlated to frequency, and provided unequivocal evidence as to the genesis of the hair cells by lineage tracing from supporting cells.

Methods of Treatment

The compounds and methods described herein are appropriate for the treatment of post-neonatal (e.g., child, adolescent or adult, e.g., above the age of 1, 2, 3, 4, 5, 6, 7, 8, 9, 10, 11, 12 or 13 years) mammalian (e.g., human) subjects who have or are at risk of developing hearing disorders resulting from cochlear hair cell loss. The methods described herein can be used to treat cochlear hair cell loss and any disorder that arises as a consequence of hair cell loss in the ear, such as hearing impairments or deafness. These subjects can receive treatment with an agent described herein. The approach may be optimal for treatment of acute hearing loss shortly after the damage has occurred, and may be less effective after longer time periods when Notch signaling has returned to its baseline level in the adult.

In some embodiments, the methods include steps of selecting a patient at risk of cochlear hair cell loss and/or a patient with cochlear hair cell loss. Alternatively or in addition, the methods include steps of selecting a patient at risk of hair cell loss and/or a patient with cochlear hair cell loss. For example, any human experiencing or at risk for developing cochlear hair cell loss is a candidate for the treatment methods described herein. A human having or at risk for developing cochlear hair cell loss can hear less well than the average human being, or less well than a human before experiencing the hair cell loss. For example, hearing can be diminished by at least 5, 10, 30, 50% or more.

The subject can have hearing loss associated with cochlear hair cell loss for any reason, or as a result of any type of event. For example, a subject can be deaf or hard-of-hearing as a result of a physical ototoxic insult, e.g., a traumatic event, such as a physical trauma to a structure of the ear. In preferred embodiments, the subject can have (or be at risk of developing) hearing loss as result of exposure to a sudden loud noise, or a prolonged exposure to loud noises. For example, prolonged or repeated exposures to concert venues, airport runways, and construction areas can cause inner ear damage and subsequent hearing loss; subjects who are subjected to high levels of environmental noise, e.g., in the home or workplace, can be treated using the methods described herein. A subject can have a hearing disorder that results from aging, e.g., presbycusis, which is generally associated with normal aging processes; see, e.g., Huang, Minn Med. 90(10):48-50 (2007) and Frisina, Annals of the New York Academy of Sciences, 1170: 708-717 (2009), and can occur in subjects as young as 18, but is generally more marked in older subjects, e.g., subjects over age 40, 45, 50, 55, 60, 65, 70, 75, 80, 85, or 90. A subject can have tinnitus (characterized by ringing in the ears) due to loss of hair cells. A subject can experience a chemical ototoxic insult, wherein ototoxins include therapeutic drugs including antineoplastic agents, salicylates, quinines, and aminoglycoside antibiotics, e.g., as described further below, contaminants in foods or medicinals, and environmental or industrial pollutants.

In some embodiments, the methods include administering to the subject a compound described herein within one, two, three, four, five, six, or seven days, or one, two, three, four, five, or six weeks of exposure to an ototoxic insult, e.g., a physical (noise, trauma) or chemical (ototoxin) insult that results in or could result in a loss of hair cells, and causes an increase in Notch signaling in the subject.

In some embodiments, a subject suitable for the treatment using the compounds and methods featured in the invention can include a subject having a vestibular dysfunction, including bilateral and unilateral vestibular dysfunction; the methods include administering a therapeutically effective amount of an agent described herein, e.g., by systemic administration or administration via the endolymphatic sac (ES). Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunctions that can be treated by the methods described herein can be the result of a genetic or congenital defect; an infection, such as a viral or bacterial infection; or an injury, such as a traumatic or nontraumatic injury, that results in a loss of vestibular hair cells. In some embodiments, balance disorders or Meniere's disease (idiopathic endolymphatic hydrops) may be treated by the methods described herein. Vestibular dysfunction is most commonly tested by measuring individual symptoms of the disorder (e.g., vertigo, nausea, and fuzzy vision).

Alternatively or in addition, the compounds and methods featured in the invention can be used prophylactically, such as to prevent, reduce or delay progression of hearing loss, deafness, or other auditory disorders associated with loss of hair cells. For example, a composition containing one or more compounds can be administered with (e.g., before, after or concurrently with) an ototoxic therapy, i.e., a therapeutic that has a risk of hair cell toxicity and thus a risk of causing a hearing disorder. Ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine. For example, a subject undergoing chemotherapy can be treated using the compounds and methods described herein. The chemotherapeutic agent cisplatin, for example, is known to cause hearing loss. Therefore, a composition containing one or more compounds can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In general, the compounds and methods described herein can be used to generate hair cell growth in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

Where appropriate, following treatment, the subject can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a subject can hear. Hearing tests in humans include behavioral observation audiometry (for infants to seven months), visual reinforcement orientation audiometry (for children 7 months to 3 years); play audiometry for children older than 3 years; and standard audiometric tests for older children and adults, e.g., whispered speech, pure tone audiometry; tuning fork tests; brain stem auditory evoked response (BAER) testing or auditory brain stem evoked potential (ABEP) testing. Oto-acoustic emission testing can be used to test the functioning of the cochlear hair cells, and electro-cochleography provides information about the functioning of the cochlea and the first part of the nerve pathway to the brain. In some embodiments, treatment can be continued with or without modification or can be stopped.

Dosage

An "effective amount" is an amount sufficient to effect beneficial or desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. In some embodiments, e.g., in subjects exposed to prolonged or repeated exposures to noise, e.g., normal noises such as are associated with activities of daily life (such as lawnmowers, trucks, motorcycles, airplanes, music (e.g., from personal listening devices), sporting events, etc.), or loud noises, e.g., at concert venues, airports, and construction areas, that can cause inner ear damage and subsequent hearing loss; e.g., subjects who are subjected to high levels of environmental noise, e.g., in the home or workplace, can be treated with repeated, e.g., periodic, doses of the pharmaceutical compositions, e.g., to prevent (reduce the risk of) or delay progression or hearing loss.

Dosage, toxicity and therapeutic efficacy of the therapeutic compounds can be determined by standard pharmaceutical procedures, e.g., in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. For example, samples of the perilymph or endolymph can be obtained to evaluate pharmacokinetics and approximate an effective dosage, e.g., in animal models, e.g., after administration to the round window. The dosage of such compounds lies preferably within a range of concentrations that include the ED50 with little or no toxicity. The dosage may vary within this range depending upon the dosage form employed and the route of administration utilized. For any compound used in the method of the invention, the therapeutically effective dose can be estimated from cell culture assays, and/or a dose may be formulated in animal models; alternatively, for those compounds that have been previously used in humans, clinically desirable concentrations can be used as a starting point. Such information can be used to more accurately determine useful doses in humans.

Pharmaceutical Compositions and Methods of Administration

The methods described herein include the manufacture and use of pharmaceutical compositions that include compounds identified herein, e.g., Notch inhibitors, e.g., gamma-secretase inhibitors, as active ingredients. Also included are the pharmaceutical compositions themselves.

The compositions include one or more notch inhibitors, e.g., gamma secretase inhibitors, e.g., RO4929097; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide, see U.S. Pat. No. 6,541,466); ELN-46719 (2-hydroxy-valeric acid amide analog of LY411575 (where LY411575 is the 3,5-difluoro-mandelic acid amide) (U.S. Pat. No. 6,541,466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl) pentanamide, Samon et al., Mol Cancer Ther 2012; 11:1565-1575); and Compound E ((2S)-2-{[(3,5-Difluorophenyl) acetyl]amino}-N-[(3S)-1-methyl-2-oxo-5-phenyl-2,3-dihydro-1H-1,4-benzodiazepin-3-yl]propanamide; see WO 98/28268 and Samon et al., Mol Cancer Ther 2012; 11:1565-1575; available from Alexis Biochemicals)), or pharmaceutically acceptable salts thereof.

In some embodiments, suitable gamma secretase inhibitors include: semagacestat (also known as LY450139, (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl] amino]ethyl]butanamide, available from Eli Lilly; WO 02/47671 and U.S. Pat. No. 7,468,365); LY411575 (N-2 ((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide, available from Eli Lilly, Fauq et al., Bioorg Med Chem Lett 17: 6392-5, 2007); begacestat (also known as GSI-953, U.S. Pat. No. 7,300,951); arylsulfonamides (A S, Fuwa et al., Bioorg Med Chem Lett. 16(16):4184-4189, 2006); N—[N-(3,5-difluorophenacetyl)-L-alanyl]-(S)-phenylglycine t-butyl ester (DAPT, Shih and Wang, Cancer Res. 67: 1879-1882, 2007); N—[N-3,5-Difluorophenacetyl]-L-alanyl-S-phenylglycine Methyl Ester (also known as DAPM, gamma-Secretase Inhibitor XVI, available from EMD Millipore); Compound W (3,5-bis(4-Nitrophenoxy) benzoic acid, available from Tocris Bioscience); L-685,458 ((5S)-(tert-Butoxycarbonylamino)-6-phenyl-(4R)-hydroxy-(2R)-benzylhexanoyl)-L-leucyl-L-phenylalaninamide, available from Sigma-Aldrich, Shearmen et al., Biochemistry 39, 8698-8704, 2000); BMS-289948 (4-chloro-N-(2,5-difluorophenyl)-N-((1R)-{4-fluoro-2-[3-(1H-imidazol-1-yl) propyl]phenyl}ethyl)benzenesulfonamide hydrochloride, available from Bristol Myers Squibb); BMS-299897 (4-[2-((1R)-1-{[(4-chlorophenyl)sulfonyl]-2,5-difluoroanilino}ethyl)-5-fluorophenyl]butanoic acid, available from Bristol Myers Squibb, see Zheng et al., Xenobiotica 39(7):544-55, 2009); avagacestat (also known as BMS-708163, (R)-2-(4-chloro-N-(2-fluoro-4-(1,2,4-oxadiazol-3-yl)benzyl)phenylsulfonamido)-5,5,5-trifluoropentanamide, available from Bristol Myers Squibb, Albright et al., J Pharmacol. Exp. Ther. 344(3):686-695, 2013); MK-0752 (3-(4-((4-chlorophenyl)sulfonyl)-4-(2,5-difluorophenyl)cyclohexyl)propanoic acid, available from Merck); MRK-003 ((3'R,6R,9R)-5'-(2,2,2-trifluoroethyl)-2-((E)-3-(4-(trifluoromethyl)piperidin-1-yl)prop-1-en-1-yl)-5,6,7,8,9,10-hexahydrospiro[6,9-methanobenzo[8]annulene-11,3'-[1,2,5]thiadiazolidine] 1',1'-dioxide, available from Merck, Mizuma et al., Mol Cancer Ther. 11(9):1999-2009, 2012); MRK-560 (N-[cis-4-[(4-Chlorophenyl)sulfonyl]-4-(2,5-difluorophenyl)cyclohexyl]-1,1,1-trifluoro-methanesulfonamide, Best et. al., J Pharmacol Exp Ther. 317(2):786-90, 2006); RO-4929097 (also known as R4733, (S)-2,2-dimethyl-N1-(6-oxo-6,7-dihydro-5H-dibenzo[b,d]azepin-7-yl)-N3-(2,2,3,3,3-pentafluoropropyl)malonamide, available from Hoffman-La Roche Inc., Tolcher et al., J Clin. Oncol. 30(19):2348-2353, 2012); JLK6 (also known as 7-Amino-4-chloro-3-methoxyisocoumarin, available from Santa Cruz Biotechnology, Inc., Petit et al., Nat. Cell. Biol. 3: 507-511, 2001); Tarenflurbil (also known as (R)-Flurbiprofen, (2R)-2-(3-fluoro-4-phenylphenyl)propanoic acid); ALX-260-127 (also known as Compound 11, described by Wolfe et al., J. Med. Chem. 41: 6, 1998); Sulindac sulfide (SSide, Takahashi et al., J Biol Chem. 278(20): 18664-70, 2003); 1,1,1- trifluoro-N-(4-[5-fluoro-2-(trifluoromethyl)phenyl]-4-{[4 (trifluoromethyl)phenyl]sulfonyl}cyclohexyl)methanesulfonamide (described in US20110275719); N-[trans-3-[(4-chlorophenyl)sulfonyl]-3-(2,5-difluorophenyl)cyclobutyl]-1,1,1-trifluoromethanesulfonamide (described in US20110263580); N-[cis-3-[(4-chlorophenyl)sulfonyl]-3-(2,5-difluorophenyl)cyclobutyl]-1,1,1-trifluoromethanesulfonamide (described in US20110263580); N-[cis-3-[(4-chlorophenyl)sulfonyl]-3-(2-cyano-5-fluorophenyl)cyclobutyl]-1,1,1-trifluoromethanesulfonamide (described in US20110263580); N-[cis-3-[(4-chlorophenyl)sulfonyl]-3-(2,5-dichlorophenyl)cyclobutyl]-1,1,1-trifluoromethanesulfonamide (described in US20110263580); N-(cis-3-(2,5-difluorophenyl)-3-{[4-(trifluoromethyl)phenyl] sulfonyl}cyclobutyl)-1,1,1-trifluoromethanesulfonamide (described in US20110263580); N-{cis-3-(5-chloro-2-fluorophenyl)-3-[(4-chlorophenyl)sulfonyl]cyclobutyl}-1,1,1-trifluoromethanesulfonamide (described in US20110263580); N-{cis-3-(2,5-difluorophenyl)-3-[(4-fluorophenyl)sulfonyl]cyclobutyl}-1,1,1-trifluoromethanesulfonamide (described in US20110263580); N-{cis-3-(2,5-difluorophenyl)-3-[(3,4-difluorophenyl)sulfonyl]cyclobutyl}-1,1,1-trifluoromethanesulfonamide (described in US20110263580); N-[cis-3-[(4-cyanophenyl)sulfonyl]-3-(2,5-difluorophenyl)cyclobutyl]-1,1,1-trifluoromethanesulfonamide (described in US20110263580); 4-{[cis-3-[(4-chlorophenyl)sulfonyl]-3-(2,5-difluorophenyl)cyclobutyl][trifluoromethyl) sulfonyl]amino}butanoic acid (described in US20110263580); N-[cis-3-[(4-chlorophenyl)sulfonyl]-3-(2,5-difluorophenyl)cyclobutyl]-1,1,1-trifluoro-N-[2-(tetrahydro-2-pyran-2-yloxy)ethyl]methanesulfonamide (described in US20110263580); Methyl{[cis-3-[(4-chlorophenyl)sulfonyl]-3-(2,5-difluorophenyl)cyclobutyl][(trifluoromethyl)sulfonyl]amino}acetate (described in US20110263580); N-[3-[(4-chlorophenyl)sulfonyl]-3-(2,5-difluorophenyl)cyclobutyl]-1,1,1-trifluoro-N-methylmethanesulfonamide (described in US20110263580); N-[3-[(4-chlorophenyl)sulfonyl]-3-(2,5-difluorophenyl)cyclobutyl]-1,1,1-trifluoro-N-methylmethanesulfonamide (described in US20110263580); Methyl 4-{[cis-3-[(4-chlorophenyl)sulfonyl]-3-(2,5-difluorophenyl)cyclobutyl] [(trifluoro-methyl)sulfonyl]amino}butanoate (described in US20110263580); N-[cis-3-[(4-chlorophenyl)sulfonyl]-3-(2,5-difluorophenyl)cyclobutyl]-N-[(trifluoromethyl)sulfonyl]glycine (described in US20110263580); N-[cis-3-[(4-chlorophenyl)sulfonyl]-3-(2,5-difluorophenyl)-1-methylcyclobutyl]-1,1,1-trifluoromethanesulfonamide (described in US20110263580); N-(cis-3-(2,5-difluorophenyl)-1-methyl-3-{[4-(trifluoromethyl)phenyl]sulfonyl}cyclobutyl)-1,1,1-trifluoromethanesulfonamide (described in US20110263580); N-[cis-3-[(4-chlorophenyl)sulfonyl]-3-(2,5-difluorophenyl)cyclobutyl]-1,1,1-trifluoro-N-[(trifluoromethyl)sulfonyl]methanesulfonamide (described in US20110263580); Sodium[cis-3-[(4-chlorophenyl)sulfonyl]-3-(2,5-difluorophenyl)cyclobutyl][(trifluoromethyl)sulfonyl]azanide (described in US20110263580); Potassium[cis-3-[(4-chlorophenyl)sulfonyl]-3-(2,5-difluorophenyl)cyclo butyl] [(trifluoromethyl)sulfonyl]azanide (described in US20110263580); N-[cis-3-[(4-trifluoromethoxyphenyl)sulfonyl]-3-(2,5-difluorophenyl)cyclobutyl]-1,1,1-trifluoromethanesulfonamide (described in US20110263580); 1,1,1-trifluoro-N-(4-[5-fluoro-2-(trifluoromethyl)phenyl]-4-{[4-(trifluoromethyl)phenyl]sulfonyl}cyclohexyl)methanesulfonamide (described in US20110263580); gamma-Secretase Inhibitor I (also known as Z-Leu-Leu-Nle-CHO, benzyloxycarbonyl-leucyl-leucyl-norleucinal, available from Calbiochem); gamma-secretase inhibitor II:

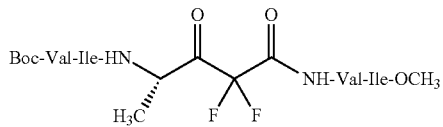

(MOL)(CDX) (available from Calbiochem); gamma secretase inhibitor III, (N-Benzyloxycarbonyl-Leu-leucinal, available from Calbiochem); gamma secretase inhibitor IV, (N-(2-Naphthoyl)-Val-phenylalaninal, available from Calbiochem); gamma-secretase inhibitor V (also known as Z-LF-CHO, N-Benzyloxycarbonyl-Leu-phenylalaninal, available from EMD Millipore); gamma-secretase inhibitor VI (1-(S)-endo-N-(1,3,3)-Trimethylbicyclo[2.2.1]hept-2-yl)-4-fluorophenyl Sulfonamide, available from EMD Millipore); gamma secretase inhibitor VII, (also known as Compound A, MOC-LL-CHO, Menthyloxycarbonyl-LL-CHO, available from Calbiochem); gamma secretase inhibitor X, ({1S-Benzyl-4R-[1-(1S-carbamoyl-2-phenethylcarbamoyl)-1S-3-methylbutylcarbamoyl]-2R-hydroxy-5-phenylpentyl}carbamic acid tert-butyl ester, available from Calbiochem); gamma secretase inhibitor XI, (7-Amino-4-chloro-3-methoxyisocoumarin, available from Calbiochem); gamma secretase inhibitor XII, (also known as Z-Ile-Leu-CHO, Shih and Wang, Cancer Res. 67: 1879-1882, 2007); gamma secretase inhibitor XIII, (Z-Tyr-Ile-Leu-CHO, available from Calbiochem); gamma secretase inhibitor XIV, (Z-Cys(t-Bu)-Ile-Leu-CHO, available from Calbiochem); gamma secretase inhibitor XVII, (also known as WPE-III-31C),

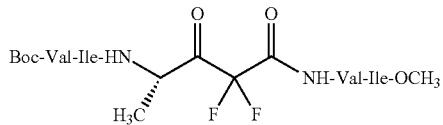

(MOL)(CDX) (available from Calbiochem); gamma secretase inhibitor XIX, (also known as benzodiazepine, (2S,3R)-3-(3,4-Difluorophenyl)-2-(4-fluorophenyl)-4-hydroxy-N-((3S)-2-oxo-5-phenyl-2,3-dihydro-TH-benzo[e][1,4]diazepin-3-yl)-butyramide, Churcher et al., J Med Chem. 46(12):2275-8, 2003); gamma secretase inhibitor XX, (also known as dibenzazepine, (S,S)-2-[2-(3,5-Difluorophenyl) acetylamino]-N-(5-methyl-6-oxo-6,7-dihydro-5H-dibenzo [b,d]azepin-7-yl)propionamide,

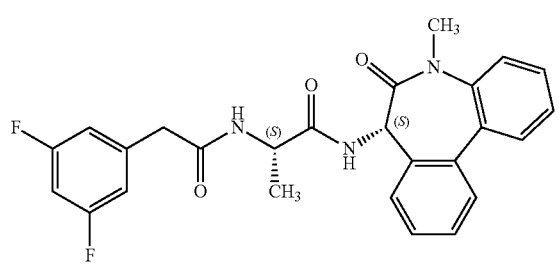

(MOL)(CDX) (Weihofen et al., Science 296: 2215-2218, 2002, available from Calbiochem); gamma secretase inhibitor XXI, ((S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, available from Calbiochem);

5-methyl-2-propan-2-ylcyclohexyl)N-[4-methyl-1-[(4-methyl-1-oxopentan-2-yl)amino]-1-oxopentan-2-yl]carbamate (available from HDH Pharma Inc.); N-trans-3,5-Dimethoxycinnamoyl-Ile-leucinal (available from Calbiochem); N-tert-Butyloxycarbonyl-Gly-Val-Valinal; isovaleryl-V V-Sta-A-Sta-OCH3 (available from Calbiochem); diethyl-(5-phenyl-3H-azepin-2-yl)-amine (described in U.S. Pat. No. 8,188,069); diethyl-(5-isopropyl-3H-azepin-2-yl)-amine (described in U.S. Pat. No. 8,188, 069); diethyl-(4-phenyl-3H-azepin-2-yl)-amine (described in U.S. Pat. No. 8,188,069); diethyl-(6-phenyl-3H-azepin-2-yl)-amine (described in U.S. Pat. No. 8,188,069); 5-pheny1-1,3-dihydro-azepin-2-one (described in U.S. Pat. No. 8,188,069); 5-Isopropyl-l,3-dihydro-azepin-2-one (described in U.S. Pat. No. 8,188,069); 4-phenyl-l,3-dihydro-azepin-2-one (described in U.S. Pat. No. 8,188,069); 6-phenyl-l,3-dihydro-azepin-2-one (described in U.S. Pat. No. 8,188,069); 2-butoxy-5-phenyl-3H-azepine (described in U.S. Pat. No. 8,188,069); 1-methyl-5-phenyl-l,3-dihydro-azepin-2-one (described in U.S. Pat. No. 8,188,069); 5-isopropyl-l-methyl-l,3-dihydro-azepin-2-one (described in U.S. Pat. No. 8,188,069); 1-methyl-4-phenyl-l,3-dihydro-azepin-2-one (described in U.S. Pat. No. 8,188,069); 1-methyl-6-phenyl-l,3-dihydro-azepin-2-one (described in U.S. Pat. No. 8,188,069); 1-methyl-5-phenyl-1H-azepine-2,3-dione-3-oxime (described in U.S. Pat. No. 8,188,069); 5-isopropyl-l-methyl-lH-azepine-2,3-dione-3-oxime (described in U.S. Pat. No. 8,188,069); 1-methyl-6-phenyl-1H-azepine-2,3-dione-3-oxime (described in U.S. Pat. No. 8,188,069); 1-methyl-4-phenyl-1H-azepine-2,3-dione-3-oxime (described in U.S. Pat. No. 8,188,069); 3-amino-l-methyl-5-phenyl-l,3-dihydro-azepin-2-one (described in U.S. Pat. No. 8,188,069); 3-amino-5-isopropyl-l-methyl-l,3-dihydro-azepin-2-one (described in U.S. Pat. No. 8,188, 069); 3-amino-l-methyl-4-phenyl-l,3-dihydro-azepin-2-one (described in U.S. Pat. No. 8,188,069); 3-amino-l-methyl-6-phenyl-l,3-dihydro-azepin-2-one (described in U.S. Pat. No. 8,188,069); (S)-[1-(1-methyl-2-oxo-5-phenyl-2,3-dihydro-lH-azepin-3-ylcarbamoyl)-ethyl]-carbamic acid tert-butyl ester (described in U.S. Pat. No. 8,188,069); [(S)-1-(5-isopropyl-l-methyl-2-oxo-2,3-dihydro-1H-azepin-3-ylcarbamoyl)-ethyl]carbamic acid tert-butyl ester (described in U.S. Pat. No. 8,188,069); [(S)-1-(1-methyl-2-oxo-4-phenyl-2,3-dihydro-1H-azepin-3-ylcarbamoyl)-ethyl]carbamic acid tert-butyl ester (described in U.S. Pat. No. 8,188,069); [(S)-1-(1-methyl-2-oxo-6-phenyl-2,3-dihydro-lH-azepin-3-ylcarbamoyl)-ethyl]-carbamic acid tert-butyl ester (described in U.S. Pat. No. 8,188,069); (S)-2-amino-N-(1-methyl-2-oxo-5-phenyl-2,3-dihydro-1H-azepin-3-yl)-propionamide (described in U.S. Pat. No. 8,188,069); (S)-2-amino-N-(5-isopropyl-l-methyl-2-oxo-2,3-dihydro-lH-azepin-3-yl)propionamide (described in U.S. Pat. No. 8,188, 069); (S)-2-Amino-N—(I-methyl-2-oxo-6-phenyl-2,3-dihydro-lH-azepin-3-yl)propionamide hydrochloride (described in U.S. Pat. No. 8,188,069); (S)-2-Amino-N—(I-methyl-2-oxo-4-phenyl-2,3-dihydro-1 H-azepin-3-yl)propionamide hydrochloride (described in U.S. Pat. No. 8,188,069); (S)-2-fluoro-3-methyl-butyric acid (described in U.S. Pat. No. 8,188,069); (S)-2-hydroxy-3-methyl-N—[(S)-1-((S)-1-methyl-2-oxo-5-phenyl-2,3-dihydro-1H-azepin-3-yl-carbamoyl)-ethyl]-butyramide (described in U.S. Pat. No. 8,188,069); (S)-2-fluoro-3-methyl-N—[(S)-1-(1-methyl-2-oxo-5-phenyl-2,3-dihydro-lH-azepin-3-ylcarbamoyl)-ethyl]-butyramide (described in U.S. Pat. No. 8,188,069); (S)-2-hydroxy-N—[(S)-1-(5-isopropyl-l-methyl-2-oxo-2,3-dihydro-1H-azepin-3-ylcarbamoyl)ethyl]-3-methyl-butyramide (described in U.S. Pat. No. 8,188,069); (S)-2-hydroxy-3-methyl-N—[(S)-1-(1-methyl-2-oxo-4-phenyl-2,3-dihydro-lH-azepin-3-ylcarbamoyl)-ethyl]-butyramide (described in U.S. Pat. No. 8,188,069); (S)-2-hydroxy-3-methyl-N—[(S)-1-(1-methyl-2-oxo-6-phenyl-2,3-dihydro-lH-azepin-3-ylcarbamoyl)-ethyl]-butyramide (described in U.S. Pat. No. 8,188,069); and(S)-2-fluoro-3-methyl-N—[(S)-1-(1-methyl-2-oxo-6-phenyl-2,3-dihydro-lH-azepin-3-ylcarbamoyl)-ethyl]-butyramide (described in U.S. Pat. No. 8,188,069), or pharmaceutically acceptable salts thereof.

Additional examples of gamma-secretase inhibitors are disclosed in U.S. Patent Application Publication Nos. 2004/0029862, 2004/0049038, 2004/0186147, 2005/0215602, 2005/0182111, 2005/0182109, 2005/0143369, 2005/0119293, 2007/0190046, 2008/008316, 2010/0197660 and 2011/0020232; U.S. Pat. Nos. 6,756,511; 6,890,956; 6,984,626; 7,049,296; 7,101,895; 7,138,400; 7,144,910; 7,183,303; 8,188,069; and International Publication Nos. WO 1998/28268; WO 2001/70677, WO 2002/049038, WO 2004/186147, WO 2003/093253, WO 2003/093251, WO 2003/093252, WO 2003/093264, WO 2005/030731, WO 2005/014553, WO 2004/039800, WO 2004/039370, WO 2009/023453, EP 1720909, EP 2178844, EP 2244713.

The entire disclosures of all of the foregoing are hereby incorporated by reference herein.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., dexamethasone; prednisone; gentamicin; brain-derived neurotrophic factor (BDNF); recombinant human insulin-like growth factor 1 (rhIGF-1), FGF, R-spondin, and/or GSK-3beta antagonists or inhibitors, e.g., one or more of the following GSK3β inhibitors: Purvalanol A, olomoucine; lithium chloride (LiCl), alsterpaullone, and kenpaullone. Other GSK3β-inhibitors that are useful in the treatments described herein include benzyl-2-methyl-1,2,4-thiadiazolidine-3,5-dione (TDZD-8); 2-thio(3-iodobenzyl)-5-(1-pyridyl)-[1,3,4]-oxadiazole (GSK3 inhibitor II); 2,4-dibenzyl-5-oxothiadiazolidine-3-thione (OTDZT); (2'Z,3'E)-6-Bromoindirubin-3'-oxime (BIO); α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl) urea (AR-A014418), H-KEAPPAPPQSpP-NH2 (L803; SEQ ID NO:1); Myr-N-GKEAPPAPPQSpP-NH2 (L803-mts; SEQ ID NO:2); and indirubins. Exemplary indirubins include indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5, 5'-dibromoindirubin; 5-nitroindirubin; 5-chloroindirubin; 5-methylindirubin; and 5-bromoindirubin. Other GSK3β-inhibitors that can be used are known in the art, e.g., those disclosed in U.S. Pat. Nos. 6,417,185; 6,489,344; 6,608,063 and Published U.S. application Ser. No. 69/0,497, filed Oct. 20, 2003; Ser. No. 46/8,605, filed Aug. 19, 2003; Ser. No. 64/6,625, filed Aug. 21, 2003; Ser. No. 36/0,535, filed Feb. 6, 2003; Ser. No. 44/7,031, filed May 28, 2003; and Ser. No. 30/9,535 filed Dec. 3, 2002.

The present pharmaceutical compositions are formulated to be compatible with the intended route of administration.

In some embodiments, the compositions are delivered systemically, e.g., by parenteral, e.g., intravenous, intradermal, or subcutaneous administration.

In some embodiments, the compositions are administered by application of a liquid or gel formulation to the round window membrane. Application to the round window membrane can be accomplished using methods known in the art, e.g., intra-tympanic injection of a liquid or gel formulation or by direct delivery into the inner ear fluids, e.g., using a microfluidic device.

In some embodiments, the compositions are delivered via a pump, e.g., a mini-osmotic pump, see, e.g., Takemura et al., Hear Res. 2004 October; 196(1-2):58-68, or a catheter, see, e.g., Charabi et al., Acta Otolaryngol Suppl. 2000; 543:108-10.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the therapeutic compounds are prepared with carriers that will protect the therapeutic compounds against rapid elimination from the body, such as a controlled release formulation, including implants and microencapsulated delivery systems. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. Nanoparticles, e.g., poly lactic/glycolic acid (PLGA) nanoparticles (see Tamura et al., Laryngoscope. 2005 November; 115(11):2000-5; Ge et al., Otolaryngol Head Neck Surg. 2007 October; 137(4):619-23; Horie et al., Laryngoscope. 2010 February; 120(2):377-83; Sakamoto et al., Acta Otolaryngol Suppl. 2010 November; (563):101-4) can also be used.

In some embodiments, the carrier comprises a polymer, e.g., a hydrogel, that increases retention of the compound on the round window and provides local and sustained release of the active ingredient. Such polymers and hydrogels are known in the art, see, e.g., Paulson et al., Laryngoscope. 2008 April; 118(4):706-11 (describing a chitosan-glycerophosphate (CGP)-hydrogel based drug delivery system); other carriers can include thermo-reversible triblock copolymer poloxamer 407 (see, e.g., Wang et al., Audiol Neurootol. 2009; 14(6):393-401. Epub 2009 Nov. 16, and Wang et al., Laryngoscope. 2011 February; 121(2):385-91); poloxamer-based hydrogels such as the one used in OTO-104 (see, e.g., GB2459910; Wang et al., Audiol Neurotol 2009; 14:393-401; and Piu et al., Otol Neurotol. 2011 January; 32(1):171-9); Pluronic F-127 (see, e.g., Escobar-Chavez et al., J Pharm Pharm Sci. 2006; 9(3):339-5); Pluronic F68, F88, or F108; polyoxyethylene-polyoxypropylene triblock copolymer (e.g., a polymer composed of polyoxypropylene and polyoxyethylene, of general formula E106 P70 E106; see GB2459910, US20110319377 and US20100273864); MPEG-PCL diblock copolymers (Hyun et al., Biomacromolecules. 2007 April; 8(4):1093-100. Epub 2007 Feb. 28); hyaluronic acid hydrogels (Borden et al., Audiol Neurootol. 2011; 16(1):1-11); gelfoam cubes (see, e.g., Havenith et al., Hearing Research, February 2011; 272(1-2):168-177); and gelatin hydrogels (see, e.g., Inaoka et al., Acta Otolaryngol. 2009 April; 129(4):453-7); other biodegradable, biocompatible polymers can be used, such as ethylene vinyl acetate, polyanhydrides, polyglycolic acid, collagen, polyorthoesters, and polylactic acid. Tunable self-assembling hydrogels made from natural amino acids L and D can also be used, e.g., as described in Hauser et al e.g. Ac-LD6-COOH (L) e.g. Biotechnol Adv. 2012 May-June; 30(3):593-603. Such formulations can be prepared using standard techniques, or obtained commercially, e.g., from Alza Corporation and Nova Pharmaceuticals, Inc.

The pharmaceutical compositions can be included in a container, pack, or dispenser together with instructions for administration.

EXAMPLES

The invention is further described in the following examples, which do not limit the scope of the invention described in the claims.

Materials and Methods

The following materials and methods were used in the examples set forth herein.

Animals

For the experiments using inner ear spheres, C57BL/6 (Jackson Labs) or Math1-nGFP reporter mouse (19) (a gift from Jane Johnson, University of Texas) of both sexes were used. To create organ of Corti explants with ablated hair cells, Mos-iCsp3 mice (line 17) (20) were crossed with Pou4f3-Cre mice (6) (a gift from Douglas Vetter, Tufts University). For all in vivo experiments, we used 4-week-old Cre reporter line, mT/mG (Jackson Labs), crossed to a Sox2-CreER mouse (47) (a gift from Konrad Hochedlinger, Mass General Hospital). After genotyping, double transgenic animals were used for lineage tracing. We used young adult wild-type littermates of the mT/mG; Sox2-CreER mice to prevent strain effects in the response to noise, which are known to vary depending on background (22, 48). Mice were genotyped by PCR. All protocols were approved by the Institutional Animal Care and Use Committee of Massachusetts Eye and Ear Infirmary or the by the ethics committee of Keio University Union on Laboratory Animal Medicine, in compliance with the Public Health Service policy on humane care and use of laboratory animals.

Isolation of Inner Ear Spheres

The utricles and cochleae of 1- to 3-d-postnatal mice of both sexes were dissected, and after careful removal of the nerve trunk and mesenchymal tissues, were trypsinized and dissociated. Dissociated cells were centrifuged, and the pellet was resuspended and filtered through a 70 µm cell strainer (BD Biosciences Discovery Labware) in DMEM/F12 medium with N2/B27 supplement, EGF (20 ng/ml), IGF1 (50 ng/ml), bFGF (10 ng/ml), and heparan sulfate (50 ng/ml) (Sigma). The single cells were cultured in nonadherent Petri dishes (Greiner Bio-One) to initiate clonal growth of spheres (49). Spheres that formed after 2-3 d in culture were passaged every 4-6 d. The spheres were centrifuged, and the pellet was mechanically dissociated with a pipette tip and resuspended in medium. Passage 3-4 spheres were used for experiments described here. These cells are negative for hair cell markers (37) before the initiation of differentiation. For differentiation, floating spheres were transferred to fibronectin-coated 4 well plates (Greiner Bio-One) as described before (37, 49). Attached spheres were differentiated for 5-7 d in DMEM/F12 medium with N2/B27 supplement but without growth factors.

Gamma-secretase inhibitors, DAPT, L-685458, MDL28170 (Sigma), and LY411575 (Santa Cruz) (See FIGS. 10A-B) were added at several concentrations on the day following cell attachment.

Neonatal Cochlear Explants

Cochleae of 3-d-postnatal C57BL/6 or Mos-iCsp3; Pou4f3-Cre double transgenic mice of both sexes were dissected in Hanks solution (Invitrogen). To obtain a flat cochlear surface preparation, the spiral ganglion, Reissner's membrane, and the most basal cochlear segment were removed. Explants were plated onto 4 well plates (Greiner Bio-One) coated with poly-L-ornithine (0.01%, Sigma) and laminin (50 µg/ml, Becton Dickinson). Cochlear explants were cultured in DMEM (Invitrogen) with 10% fetal bovine serum. All cultures were maintained in a 5% CO2/20% O2-humidified incubator (Forma Scientific).

Acoustic Overexposure 4-week-old mice were exposed free-field, awake and unrestrained, in a small reverberant chamber (22). Acoustic trauma was produced by a 2 h exposure to an 8-16 kHz octave band noise presented at 116 dB SPL. The exposure stimulus was generated by a custom white-noise source, filtered (Brickwall Filter with a 60 dB/octave slope), amplified (Crown power amplifier), and delivered (JBL compression driver) through an exponential horn fitted securely to a hole in the top of a reverberant box. Sound exposure levels were measured at four positions within each cage using a 0.25 inch Brüel and Kjær condenser microphone: sound pressure was found to vary by <0.5 dB across these measurement positions.

Systemic or Round Window Administration of LY411575

4-week-old mice weighing 12 to 16 g were used. Before surgery, the animals were anesthetized with ketamine (20 mg/kg, i.p.) and xylazine (100 mg/kg, i.p.), and an incision was made posterior to the pinna near the external meatus after local administration of lidocaine (1%). The otic bulla was opened to approach the round window niche. The end of a piece of PE 10 tubing (Becton Dickinson) was drawn to a fine tip in a flame and gently inserted into the round window niche. LY411575 was dissolved in DMSO and diluted 10-fold in polyethylene glycol 400 (Sigma) to a final concentration of 4 mM. This solution (total volume 1 µl) was injected into the round window niche of the left ear. Polyethylene glycol 400 with 10% DMSO was injected into the right ear as a control. The solution was administered for 2 min. This approach is presently used clinically (e.g. transtympanic injection of steroids for sudden hearing loss and gentamicin for severe balance disorders) and has the advantage of sparing the inner ear but still taking advantage of the local route provided by the round window membrane for delivery of drug into the inner ear (50). Gelatin was placed on the niche to maintain the solution, and the wound was closed.

For systemic administration, LY411575 (50 mg/kg) dissolved in 0.5% (wt/vol) methylcellulose (WAKO) was injected orally once daily for 5 consecutive d. Hearing was measured by ABR at 1 d before, 2 d, 1, 2 week, 1, 2 and 3 months after noise exposure.

qRT-PCR

The organs of Corti were dissected in HBSS (Invitrogen) and stored in RNAlater (Ambion) at −80° C. until further use. Total RNA was extracted using the RNeasy Mini Kit (Qiagen) according to the manufacturer's instructions. For reverse transcription, SuperScript II (Invitrogen) was used with random hexamers. The reverse transcription conditions were 25° C. for 10 min followed by 37° C. for 60 min. The reaction was terminated at 95° C. for 5 min. cDNAs were mixed with Taqman Gene Expression Mastermix (Applied Biosystems) and Hes5, Atoh1, or 18S primers (Applied Biosystems) according to the manufacturer's instructions. Samples were analyzed in 96 wells in triplicate by qPCR (Applied Biosystems 7900HT), and PCR thermal cycling conditions were as follows: initial denaturation at 95° C. for 2 min, denaturation at 95° C. for 15 s, annealing/extension at 60° C. for 1 min for 45 cycles. Conditions were kept constant for each primer. Each PCR reaction was carried out in triplicate. Relative gene expression was analyzed by using the $\Delta\Delta C_T$ method. Gene expression was calculated relative to 18S RNA, and the amount of cDNA applied was adjusted so that the Ct value for 18S RNA was between 8 and 11.

Immunohistochemistry

For spheres, cells were fixed for 10 min with 4% paraformaldehyde in PBS. Immunostaining was initiated by blocking for 1 h with 0.1% Triton X-100 in PBS supplemented with 1% BSA and 5% goat serum (PBT1). Fixed and permeabilized cells were incubated overnight in PBT1 with polyclonal antibody to myosin VIIa (Proteus Biosciences). Samples were washed three times for 20 min with PBS.

Primary antibodies were detected with secondary antibodies conjugated with Alexa 488 (Molecular Probes), with secondary antibody alone used as a negative control. The samples were counterstained with DAPI (Vector Laboratories) or Hoechst 33258 (Invitrogen) for 10 min and viewed by epifluorescence microscopy (Axioskop 2 Mot Axiocam, Zeiss).

For explants, the organs of Corti were fixed for 15 min with 4% paraformaldehyde in PBS. Immunostaining was initiated by blocking the tissues for 1 h with 0.1% Triton X-100 in PBS supplemented with 5% donkey serum (PBT1). Fixed and permeabilized cells were incubated overnight in PBT1 with polyclonal antibody to myosin VIIa (Proteus Biosciences), Sox2 (Santa Cruz), GFP (Invitrogen), prestin (Santa Cruz), and CtBP2 (BD Biosciences). Samples were washed three times for 20 min with PBS. Primary antibodies were detected with secondary antibodies conjugated with Alexa 488 and 647 (Molecular Probes). The samples were stained with rhodamine phalloidin (Invitrogen) for 15 min and viewed by confocal fluorescence microscopy (TCS SP5, Leica).

For collection of mature mouse cochleae, after being deeply anesthetized with ketamine and xylazine, the mice were transcardially perfused with 0.01 M phosphate buffer (pH 7.4) containing 8.6% sucrose, followed by fixative consisting of freshly depolymerized 4% paraformaldehyde in 0.1 M phosphate buffer (pH 7.4). After decapitation, the temporal bones were removed and immediately placed in the same fixative at 4° C. Small openings were made at the round window, oval window, and apex of the cochlea. After immersion in the fixative overnight at 4° C., temporal bones were decalcified in 0.1 M EDTA (pH 7.4) containing 5% sucrose with stirring at 4° C. for 2 d. After decalcification, cochleae were microdissected into 4 pieces for whole mount preparation. Immunostaining was initiated by blocking the tissues for 1 h with 0.1% Triton X-100 in PBS supplemented with 5% donkey serum (PBT1). Fixed and permeabilized pieces were incubated overnight in PBT1 with polyclonal antibody to myosin VIIa (Proteus Biosciences), Sox2 (Santa Cruz), and GFP (Invitrogen). Samples were washed three times for 20 min with PBS. Primary antibodies were detected with secondary antibodies conjugated with Alexa 488, 568, and 647 (Molecular Probes) and viewed by confocal fluorescence microscopy (TCS SP5, Leica). Cochlear lengths were obtained for each case, and a cochlear frequency map computed to precisely localize inner hair cells from the 5.6, 8.0, 11.3, 16.0, 22.6, 32, and 45.2 kHz regions. For cross-sectioning, fixed temporal bones were sunk in 30% sucrose in PBS at 4° C., incubated in OCT at room temperature for 1 h, and frozen in liquid nitrogen. The staining protocol was the same as described above except for counterstaining with DAPI (Vector Laboratories). Specimens were viewed by epifluorescence microscopy (Axioskop 2 Mot Axiocam, Zeiss).

Cell Counts

Cell counting for spheres was performed with MetaMorph software. The cell number was determined from DAPI- or Hoechst-positive nuclei. Repeat cell counting gave a test variation of <10%. For explants, inner hair cells, outer hair cells, and supporting cells in the outer hair cell region were counted on cochlear whole mounts. Hair cells were identified with myosin VIIa antibodies or endogenous GFP in Math1-nGFP mice. High-power images of the full-length cochlea or cochlear explant cultures were assembled and analyzed in PhotoShop CS4 (Adobe). ImageJ software (NIH) was used to measure the total length of cochlear whole mounts and the length of individual counted segments. The total number of inner hair cells, outer hair cells, and supporting cells in the outer hair cell region was counted in each of four cochlear segments of 1200-1400 µm (apical, mid-apical, mid-basal, and basal). Density (cells per 100 µm) was then calculated for each segment. For mature cochleae, high-power images of frequency-specific regions (5.6, 8.0, 11.3, 16.0 kHz) according to the computed frequency map were assembled and analyzed. The number of inner hair cells, outer hair cells, and supporting cells in the outer hair cell region in 100 µm was counted in each of the four frequency-specific regions of the cochlea. The number of Sox2-lineage-positive cells identified by GFP was counted by the same method.

ABR Measurements

Auditory brain stem responses (51, 52) were measured in each animal at 7 log-spaced frequencies (half-octave steps from 5.6 to 45.2 kHz) before and 1 d after noise exposure, and 1-week, 1-month, and 3-months after surgery. Mice were anesthetized with ketamine (100 mg/kg i.p.) and xylazine (20 mg/kg i.p.). Needle electrodes were inserted at vertex and pinna, with a ground near the tail. ABRs were evoked with 5-ms tone pips (0.5-ms rise-fall with a $\cos^2$ onset envelope delivered at 35/s). The response was amplified, filtered and averaged in a LabVIEW-driven data-acquisition system. Sound level was raised in 5 dB steps from ≥10 dB below threshold <80 dB SPL. At each sound level, 1024 responses were averaged (with stimulus polarity alternated), using an "artifact reject," whereby response waveforms were discarded when peak-to-peak response amplitude exceeded 15 µV. On visual inspection of stacked waveforms, "ABR threshold" was defined as the lowest SPL level at which any wave could be detected, usually corresponding to the level step just below that at which the peak-to-peak response amplitude rose significantly above the noise floor (approximately 0.25 µV). When no response was observed at the highest sound level available, the threshold was designated as being 5 dB greater than that level so that statistical tests could be done. For amplitude versus level functions, the wave I peak was identified by visual inspection at each sound level and the peak-to-peak amplitude computed.

Quantification and Statistical Analysis

The 2-tailed Mann-Whitney U test was used to compare differences among treatment groups. Changes before and after treatment of the same animal were analyzed by 2-tailed Wilcoxon t test. Repeated-measures ANOVA was used to compare time-dependent differences among groups. Data are presented in the text and in figures as mean±SEM. P values less than 0.05 were considered significant.

Genotyping Primers

Mos-iCsp3

LacZ F: 5'-ttcactggccgtcgttttacaacgtcgtga-3' (SEQ ID NO:1)

LacZ R: 5'-atgtgagcgagtaacaacccgtcggattct-3' (SEQ ID NO:2)

Pou4f3Cre, Sox2CreER

Cre F: 5'-tgggcggcatggtgcaagtt-3' (SEQ ID NO:3)

Cre R: 5'-cggtgctaaccagcgttttc-3' (SEQ ID NO:4)

mT/mG oIMR7318 wild-type F: 5'-ctctgctgcctcctggcttct-3' (SEQ ID NO:5)

oIMR7319 wild-type R: 5'-cgaggcggatcacaagcaata-3' (SEQ ID NO:6)

oIMR7320 mutant R: 5'-tcaatgggcggggtcgtt-3' (SEQ ID NO:7)

Figure 1:
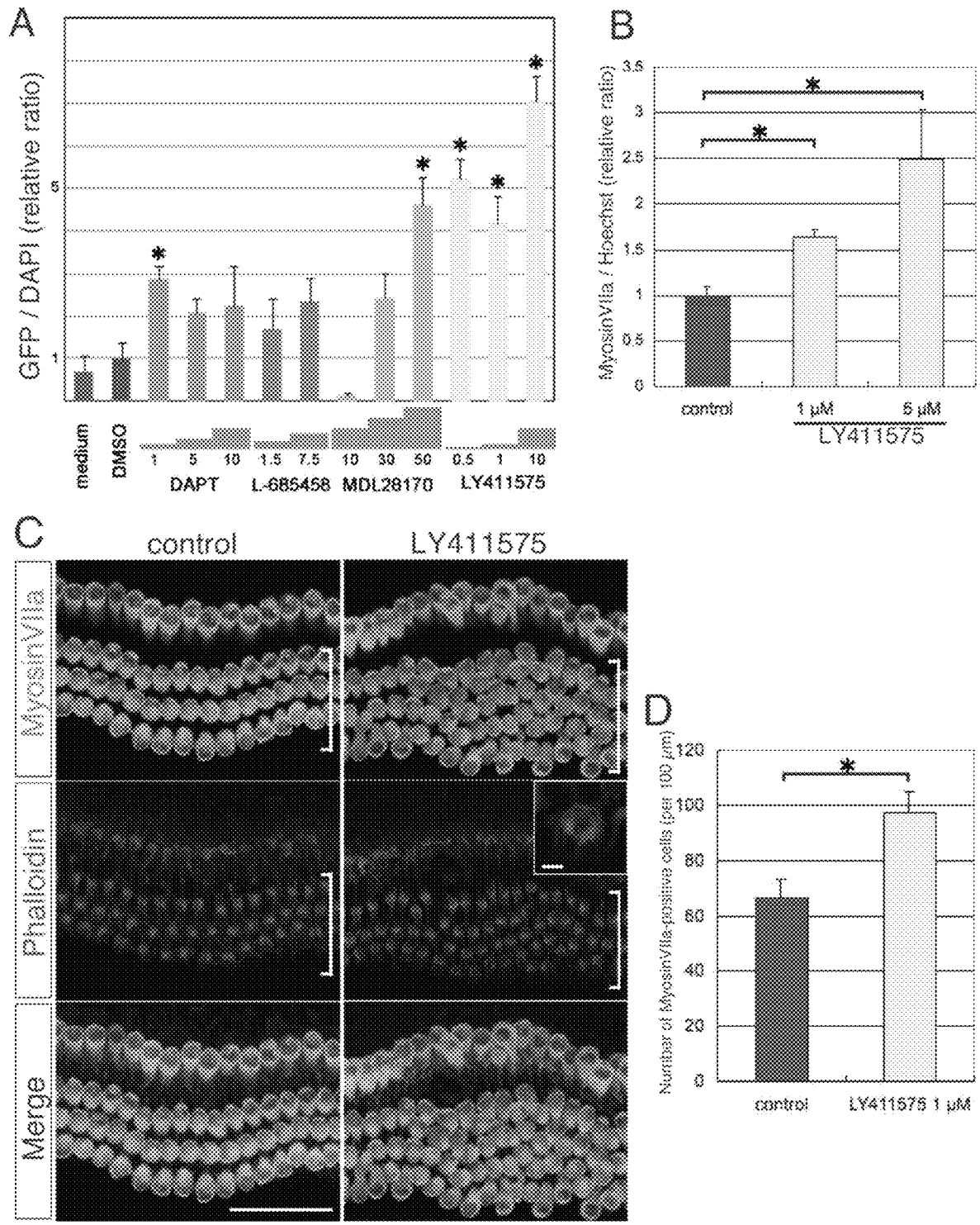
FIGS. 1A-D. In vitro activity of γ-secretase inhibitors in hair cell induction (A) Relative ratio of nGFP-positive cells to DAPI-positive cells after treatment of inner ear spheres made from Math1-nGFP mice with γ-secretase inhibitors at the indicated concentrations (μM) reveals that LY411575 had the greatest potency of 4 inhibitors tested for hair cell induction. Data were normalized to control values obtained by addition of DMSO. Asterisks indicate $p<0.01$.

Example 1. Screening for γ-Secretase Inhibitors that Induce Hair Cell Differentiation from Inner Ear Stem Cells Ligand-triggered γ-secretase activity catalyzes proteolytic release of Notch intracellular domain and thereby mediates the first step of Notch signal transduction. We previously showed that γ-secretase inhibitors promoted hair cell differentiation from inner ear stem cells by an effect on Notch (15). To find the most potent inhibitor several known drugs, DAPT, L-685458, MDL28170, and LY411575 (see FIGS. 10A-B), were tested for their effect on hair cell differentiation from utricular spheres derived from neonatal Math1-nGFP reporter mice (19). In this system, LY411575 had the highest potency (FIG. 1a) among the four γ-secretase inhibitors. To confirm the effect of LY411575 on cochlear cells, spheres derived from organ of Corti were used. Upon treatment with LY411575, the numbers of myosin VIIa-positive cells (myosin VIIa is a specific marker for hair cells) increased 1.5 to 2.5 fold above control (FIG. 1B). These cells were also positive for calretinin, another marker for hair cells, and their hair bundles were positive for espin.

Example 2. LY411575 Increased Hair Cell Number in Organ of Corti Explants

The effect of LY411575 was further characterized on neonatal organ of Corti explants. The addition of LY411575 increased the number of myosin VIIa-positive cells in the outer hair cell region (FIG. 1C) by 30 cells/100 µm compared to the control (FIG. 1D, $p<0.05$). The additional hair cells showed hair bundle structures. These results indicated that the γ-secretase inhibitor, which was chosen by screening using inner ear stem cells, effectively induced extra hair cell differentiation in the neonatal organ of Corti.

Figure 2:
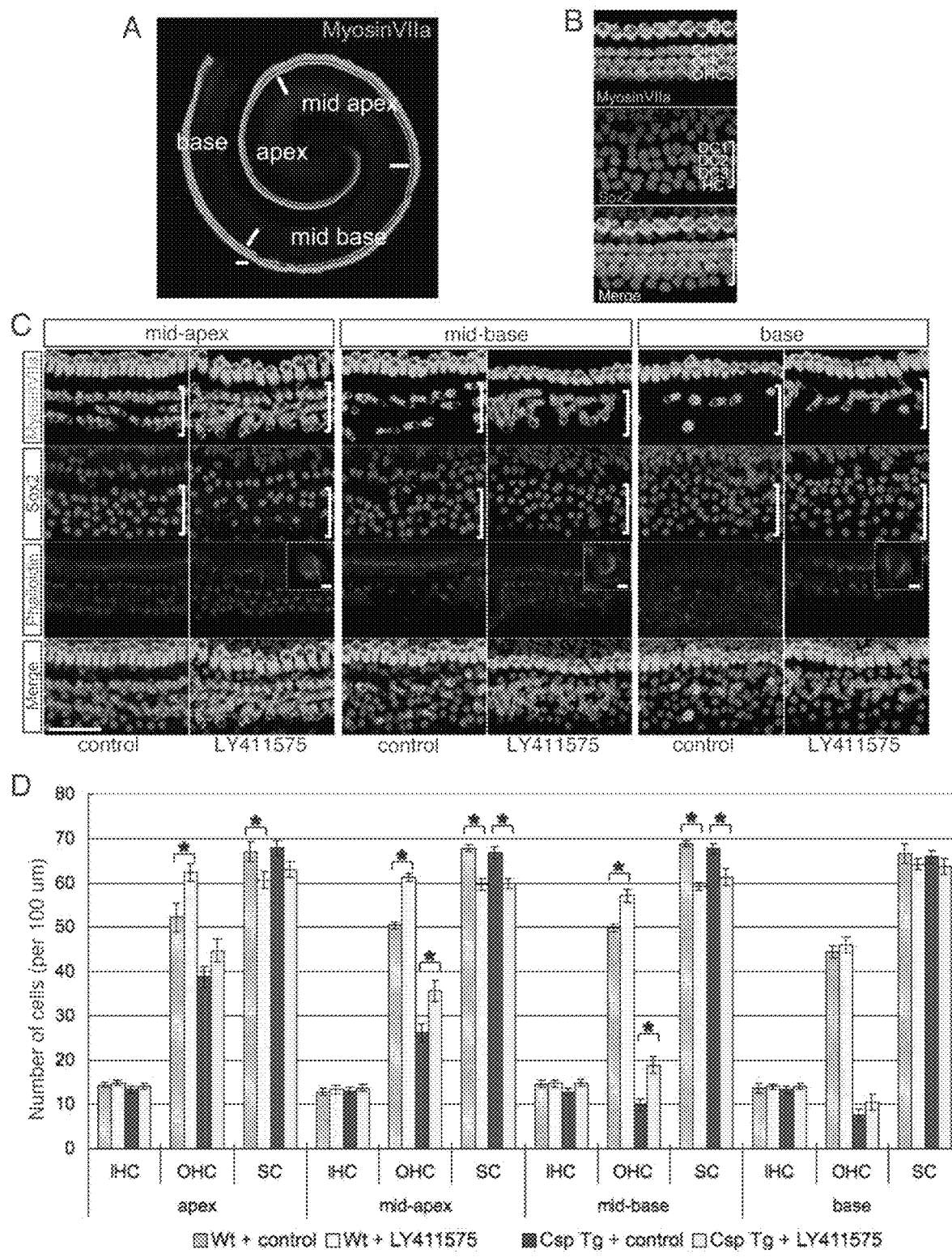

Next, organ of Corti explants from Pou4f3-Cre; Mos-iCsp3 double transgenic mice were used to test whether hair cells could be induced after damage (FIG. 2A). This Mos-iCsp3 mouse has a Cre/lox cassette that produces a drug-regulated dimerizable caspase-3 (20) in hair cells, because Pou4f3, which is expressed transiently in the developing inner ear, is limited to hair cells (21). Thus, after treatment with a drug that dimerizes caspase-3, the dimer leads to hair cell death. Mos-iCsp3 cochleae showed loss of outer hair cells (FIG. 2B vs FIG. 2C, control). LY411575 treatment of Mos-iCsp3 organ of Corti increased the number of myosin VIIa-positive (hair) cells in the outer hair cell region (FIG. 2D; $p<0.05$) and was accompanied by a decrease in the number of Sox2-positive (supporting) cells in the mid-apex and mid-base of the cochlea (FIG. 2D; $p<0.05$). There were no significant differences in the number of inner hair cells in any group. The correlation between the increase in outer hair cells and the decrease in supporting cells after LY411575 treatment suggested that supporting cells transdifferentiated into hair cells when Notch signaling was prevented.

Example 3. Systemic LY411575 Administration Increased Hair Cell Number and Promoted Hearing Recovery in a Noise-Damaged Cochlea To assess whether hair cell differentiation could be induced in a mature ear, mice were first exposed to an acoustic injury (22) producing widespread outer hair cell death and permanent hearing loss with preservation of supporting cells (see Example 5 and FIGS. 7A-C). Oral LY411575 at 50 mg/kg body weight for 5 d decreased the noise-induced threshold shift at 4, 8 and 16 kHz (FIG. 8A). Outer hair cell numbers were increased and the new hair cells had stereociliary bundles (FIG. 8B). The treated mice suffered significant side-effects (see Example 6). A lower dose (10 mg/kg body weight) had no therapeutic benefit.

Example 4. Local LY411575 Administration Promoted Hearing Recovery by Supporting Cell Transdifferentiation into Hair Cells after Noise-Induced Hearing Loss in the Mature Cochlea Due to the dose-limiting toxicity after systemic administration of the drug, direct delivery to the inner ear via the round window membrane, a permeable cellular barrier between the middle and inner ear (23, 24), was tested. The time course of Hes5 and Atoh1 mRNA expression levels were assessed in the deafened mature cochlea in the presence and absence of LY411575 using quantitative RT-PCR. Hes5 is a direct downstream target of Notch signaling that represses Atoh1 (25). LY411575 was administered via the round window niche 1 d after noise exposure. After the noise exposure, Hes5 mRNA expression increased by 2.15±0.26 compared to its pre-noise level and its level gradually decreased to reach the pre-noise level 3 d after noise exposure (FIG. 3A). This induction was completely blocked in the LY411575 treated group at 1 d and stayed at the pre-noise level (significant difference from the control cochlea, $p<0.01$). Three days after LY411575 treatment, the Hes5 expression level was unchanged from the control cochlea. In contrast to Hes5, Atoh1 expression remained stable after noise exposure (FIG. 3B). Its expression was significantly increased 1 d after LY411575 treatment to 2.28× above the level post-noise exposure, and remained elevated 3 d after treatment ($p<0.05$), before returning to the pre-noise level after 7 d. These results showed that a Notch signal could be activated by intense noise trauma, and reduction of Hes5 in the young adult mouse cochlea by local γ-secretase inhibitor treatment led to sustained upregulation of Atoh1.

Figure 4:
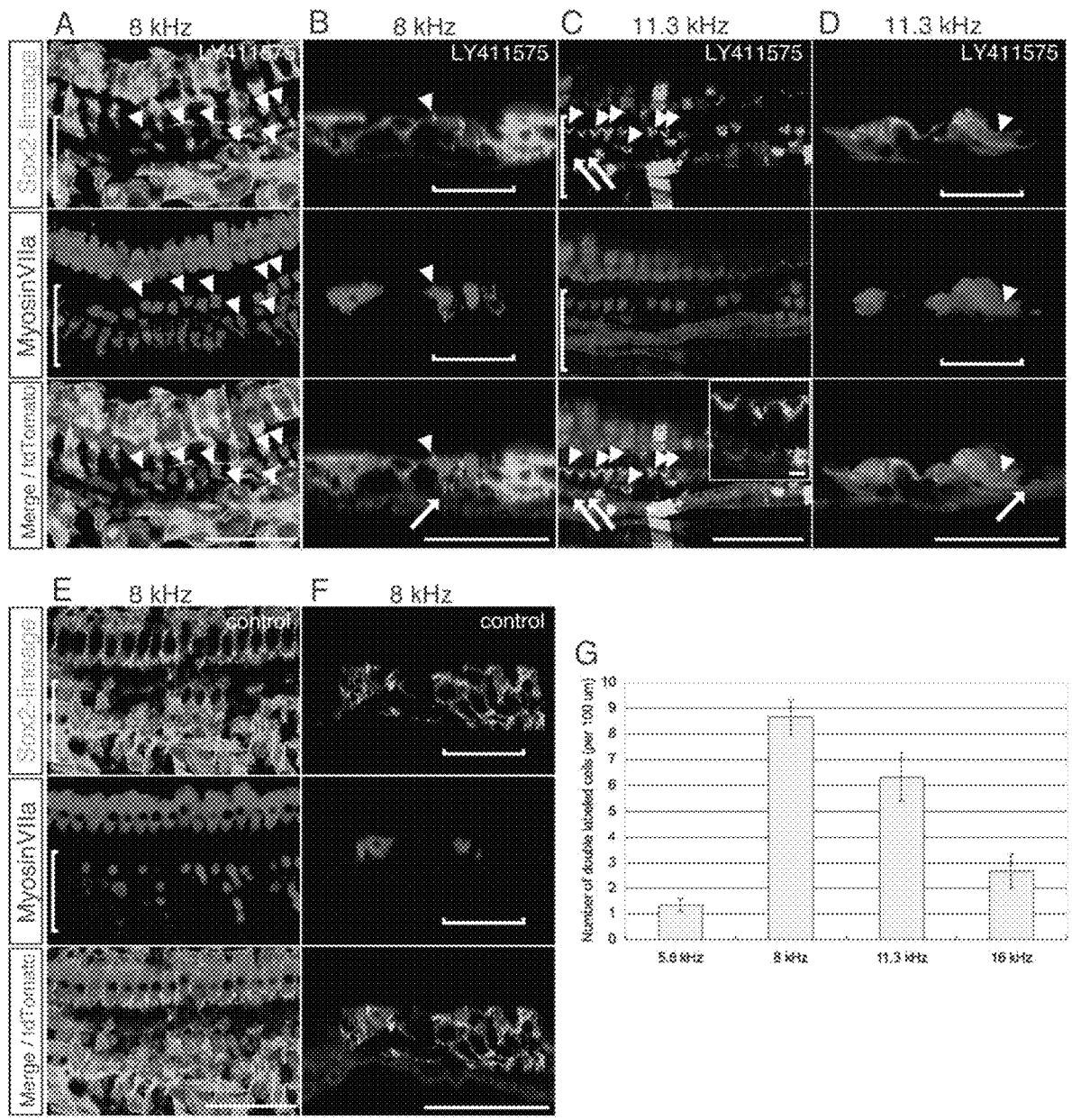

In vivo lineage tracing was used to test whether transdifferentiation could account for new hair cells. A Cre-reporter strain was used to perform lineage tracing of Sox2-positive cells since Sox2 is expressed in supporting cells. In Sox2-CreER; mT/mG mice, cells expressing Sox2 at the time of tamoxifen administration become positive for GFP and retain expression even if they lose Sox2 expression (FIG. 9). Reporter mice were exposed to noise 1 week after tamoxifen treatment, and administered LY411575 to the left ear and carrier to the right ear 1 d after noise exposure. One month after LY411575 treatment, numerous myosin VIIa-positive cells in the deafened cochlea also expressed GFP, demonstrating transdifferentiation from Sox2-positive cells. Hair bundles were observed in the myosin VIIa/GFP double-labeled cells (green in original; FIGS. 4A and 4C), and some of the bundles appeared in a V-shaped arrangement like the original hair cells (FIGS. 4C and D). Furthermore, the GFP-labeled cells showed positive staining for prestin, the motor protein of outer hair cells (Dallos et al., 2006), and were negative for VGLUT3, a marker of inner hair cells (Seal et al., 2008), as well as CtBP2, a synaptic ribbon marker that would be expected to be expressed if the new hair cells were active inner hair cells (Khimich et al., 2005; Liberman et al., 2011). This analysis of markers together with their location and V-shaped bundles identified them as outer hair cells. These double-labeled cells spanned the epithelium from basilar membrane to the endolymphatic surface (FIG. 4D), which is never seen in the normal ear, but has been reported when supporting cells are transfected with Atoh1 (16). The nucleus of these cells was at the base of the cell. Double-labeled cells were found in the upper turns of the cochlea, with the highest numbers in the mid apex (FIG. 4G; n=5). In control ears, no double-labeled cells were observed in any cochlear region (FIGS. 4E and F). This result indicated that blocking Notch with LY411575 promoted supporting cell transdifferentiation into hair cells from the apical to mid-apical turn in the mature cochlea after noise-induced hair cell loss.

At 3 months the number of outer hair cells was increased throughout the middle of the cochlea (8-16 kHz) in LY411575 treated ears, compared to the carrier-treated contralateral ear (FIGS. 5A and B; p<0.05). The number of supporting cells in the outer hair cell region was decreased significantly in the same cochleae as the increase in outer hair cell number at the 8 and 11.3 kHz areas compared to the carrier-treated ear (FIGS. 5A and B; p<0.05). Decreases in supporting cells were also significant (FIG. 5B, p<0.05) similar to the explant cultures. The outer hair cells were completely absent with and without LY411575 treatment in the most basal regions (above 22 kHz), and there were no significant changes in the numbers of inner hair cells in the treated group (data not shown). The differences in outer hair cell number between LY411575 and carrier-treated ears are larger than the corresponding differences in the number of supporting cells. Furthermore, the differences in outer hair cell number showed a similar trend, in regard to cochlear location, as the myosin VIIa-positive cells from the Sox2-lineage observed in Sox2-CreER; mT/mG mice (FIG. 4G).

Figure 6:
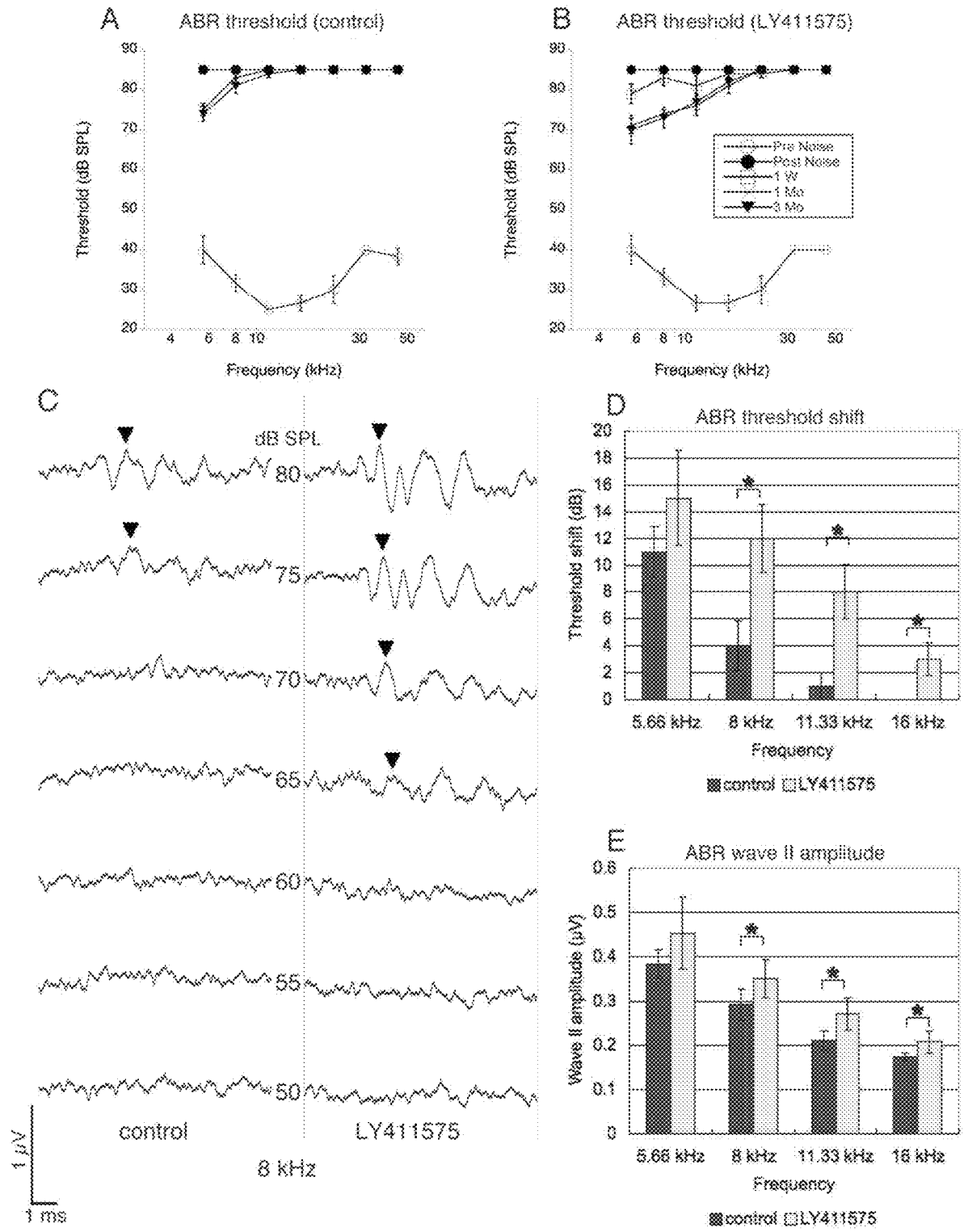

The auditory brainstem response (ABR) was recorded in LY411575 and carrier-treated, control ears to determine the effect of hair cell replacement on the thresholds for a response. Threshold changes were not seen after injection of carrier alone. ABR thresholds 1 d after noise-exposure were >80 dB SPL at all frequencies (FIGS. 6A and B). Post-exposure recovery in control ears (FIG. 6A) was minimal under these conditions, as expected (22). Surprisingly, threshold recoveries after LY411575 treatment were significantly greater than control at 8, 11.33 and 16 kHz (FIG. 6D), and wave I amplitudes were increased at the same frequencies (FIG. 6E). No threshold recoveries were observed in either ear at frequencies above 22.65 kHz by ABR and no recoveries above the noise floor of the distortion product otoacoustic emissions (DPOAE) could be seen. The differences in threshold recovery showed a similar dependence on cochlea location/frequency as outer hair cell number (see FIG. 5).

Example 5. Noise-Induced Hearing Loss in the Mature Cochlea

A noise-induced hearing loss model in young adult mice was also used. At an exposure intensity of 116 dB SPL (8-16 kHz), which leads to permanent hearing loss and major hair cell death especially in the outer hair cells region (22), almost all inner hair cells were preserved (from the apical tip to the 22 kHz area), while the outer hair cells showed severe loss. Moreover, almost all supporting cell were preserved (FIGS. 7A-C). Thus the 116 dB noise exposure model was selected as a hair cell loss model to investigate hair cell regeneration.

Example 6 Systemic LY411575 Treatment Ameliorates Hearing Loss in the Mature Noise-Damaged Cochlea Preliminary range finding experiments for drug treatment were carried out by systemic injection and were limited by toxicity. A minimal dosing regimen for an effect on the thymus weight was chosen (43, 44). Of 12 mice administered 50 mg/kg for 5 d, 6 could be tested for ABR at 3 months, the final time point of the LY411575 treatment. The rest died within the first week due to severe diarrhea and weight loss. Mice that survived also suffered from weight loss (approximately 15% loss in 3 d), with a loss of epithelial cells of their stomach and increase in secreting cells in all gastro-intestinal tract from esophagus to colon and severe atrophy in the spleen in a week; immunosuppression with an atrophy of thymus (total number of the cells were dramatically decreased to ¼₀ and double positive fraction of CD4 and CD8 was decreased from 78.6% to 1.23%), changes in the skin color in the next week. Those changes resulted from Notch inhibition reported by previous papers (44, 45). A small threshold shift (FIG. 8A) that achieved statistical significance by comparison of the control and treated animals after 1 month and persisted to 3 months was observed at 4, 8 and 16 kHz. Hair cell counts indicated an increase in outer hair cells, which were most apparent at the regions where the damage was most severe (low frequency, FIG. 8A) and the hair cells appeared to have stereociliary bundles and synapses visualized by double staining with CtBP2 and neurofilament antibody (FIG. 8B).

Example 7. Model for Lineage Tracing of Supporting Cells

To visualize supporting cell transdifferentiation into hair cells, a reporter line was used: mT/mG mice (46) crossed with Sox2-CreER mice. In the mT/mG mice, cells that have undergone Cre recombination are labeled by expression of membrane-bound GFP (GFP; green fluorescence), and non-recombined cells express td-Tomato (red fluorescence) after tamoxifen treatment. The result is a Cre-reporter line that can be used for lineage tracing of Sox2-positive cells. In the double-transgenic mouse cochlea, after estrogen receptor activation by tamoxifen in Sox2-positive cells, supporting cells expressed green fluorescence from GFP and hair cells retained fluorescence from td-Tomato (red in original; FIG. 9).

REFERENCES

1. A. J. Hudspeth, Making an effort to listen: mechanical amplification in the ear. Neuron 59, 530 (Aug. 28, 2008).
2. G. D. Nayak, H. S. Ratnayaka, R. J. Goodyear, G. P. Richardson, Development of the hair bundle and mechanotransduction. Int J Dev Biol 51, 597 (2007).
3. P. Chen, N. Segil, p27(Kip1) links cell proliferation to morphogenesis in the developing organ of Corti. Development 126, 1581 (April, 1999).
4. A. S. Edge, Z. Y. Chen, Hair cell regeneration. Curr Opin Neurobiol 18, 377 (August, 2008).
5. M. W. Kelley, Regulation of cell fate in the sensory epithelia of the inner ear. Nat Rev Neurosci 7, 837 (November, 2006).
6. C. Sage et al., Proliferation of functional hair cells in vivo in the absence of the retinoblastoma protein. Science 307, 1114 (Feb. 18, 2005).
7. J. T. Corwin, D. A. Cotanche, Regeneration of sensory hair cells after acoustic trauma. Science 240, 1772 (Jun. 24, 1988).
8. B. Fritzsch, K. W. Beisel, L. A. Hansen, The molecular basis of neurosensory cell formation in ear development: a blueprint for hair cell and sensory neuron regeneration? Bioessays 28, 1181 (December, 2006).

9. B. M. Ryals, E. W. Rubel, Hair cell regeneration after acoustic trauma in adult Coturnix quail. Science 240, 1774 (Jun. 24, 1988).
10. J. Adam et al., Cell fate choices and the expression of Notch, Delta and Serrate homologues in the chick inner ear: parallels with Drosophila sense-organ development. Development 125, 4645 (December, 1998).
11. N. Daudet, J. Lewis, Two contrasting roles for Notch activity in chick inner ear development: specification of prosensory patches and lateral inhibition of hair-cell differentiation. Development 132, 541 (February, 2005).
12. S. A. Batts, C. R. Shoemaker, Y. Raphael, Notch signaling and Hes labeling in the normal and drug-damaged organ of Corti. Hear Res 249, 15 (March, 2009).
13. A. Doetzlhofer et al., Hey2 regulation by FGF provides a Notch-independent mechanism for maintaining pillar cell fate in the organ of Corti. Dev Cell 16, 58 (January, 2009).
14. B. H. Hartman et al., Hes5 expression in the postnatal and adult mouse inner ear and the drug-damaged cochlea. J Assoc Res Otolaryngol 10, 321 (September, 2009).
15. S. J. Jeon, M. Fujioka, S. C. Kim, A. S. B. Edge, Notch signaling alters sensory or neuronal cell fate specification of inner ear stem cells. J. Neurosci. 31, 8351 (Jun. 8, 2011).
16. M. Izumikawa et al., Auditory hair cell replacement and hearing improvement by Atoh1 gene therapy in deaf mammals. Nat Med 11, 271 (March, 2005).
17. S. P. Gubbels, D. W. Woessner, J. C. Mitchell, A. J. Ricci, J. V. Brigande, Functional auditory hair cells produced in the mammalian cochlea by in utero gene transfer. Nature 455, 537 (Sep. 25, 2008).
18. J. L. Zheng, W. Q. Gao, Overexpression of Math1 induces robust production of extra hair cells in postnatal rat inner ears. Nat Neurosci 3, 580 (June, 2000).
19. E. A. Lumpkin et al., Math1-driven GFP expression in the developing nervous system of transgenic mice. Gene Expr Patterns 3, 389 (August, 2003).
20. M. Fujioka, H. Tokano, K. S. Fujioka, H. Okano, A. S. Edge, Generating mouse models of degenerative diseases using Cre/lox-mediated in vivo mosaic cell ablation. J Clin Invest 121, 2462 (Jun. 1, 2011).
21. C. Sage et al., Essential role of retinoblastoma protein in mammalian hair cell development and hearing. Proc Natl Acad Sci USA 103, 7345 (May 9, 2006).
22. Y. Wang, K. Hirose, M. C. Liberman, Dynamics of noise-induced cellular injury and repair in the mouse cochlea. J Assoc Res Otolaryngol 3, 248 (September, 2002).
23. M. V. Goycoolea, L. Lundman, Round window membrane. Structure function and permeability: a review. Microsc Res Tech 36, 201 (Feb. 1, 1997).
24. A. N. Salt, S. K. Plontke, Principles of local drug delivery to the inner ear. Audiol Neurootol 14, 350 (2009).
25. A. Zine et al., Hes1 and Hes5 activities are required for the normal development of the hair cells in the mammalian inner ear. J Neurosci 21, 4712 (Jul. 1, 2001).
26. P. M. White, A. Doetzlhofer, Y. S. Lee, A. K. Groves, N. Segil, Mammalian cochlear supporting cells can divide and trans-differentiate into hair cells. Nature 441, 984 (Jun. 22, 2006).
27. H. Lowenheim et al., Gene disruption of p27(Kip1) allows cell proliferation in the postnatal and adult organ of corti. Proc Natl Acad Sci USA 96, 4084 (Mar. 30, 1999).
28. J. Mantela et al., The retinoblastoma gene pathway regulates the postmitotic state of hair cells of the mouse inner ear. Development 132, 2377 (May, 2005).
29. M. Cohen-Salmon et al., Targeted ablation of connexin26 in the inner ear epithelial gap junction network causes hearing impairment and cell death. Curr Biol 12, 1106 (Jul. 9, 2002).
30. A. B. Elgoyhen, L. F. Franchini, Prestin and the cholinergic receptor of hair cells: positively-selected proteins in mammals. Hear Res 273, 100 (March, 2011).
31. G. P. Richardson, J. B. de Monvel, C. Petit, How the genetics of deafness illuminates auditory physiology. Annu Rev Physiol 73, 311 (Mar. 17, 2011).
32. M. Caiazzo et al., Direct generation of functional dopaminergic neurons from mouse and human fibroblasts. Nature 476, 224 (Aug. 11, 2011).
33. T. Vierbuchen et al., Direct conversion of fibroblasts to functional neurons by defined factors. Nature 463, 1035 (Feb. 25, 2010).
34. Y. Kaneko et al., Musashi1: an evolutionarily conserved marker for CNS progenitor cells including neural stem cells. Dev Neurosci 22, 139 (2000).
35. E. C. Oesterle, S. Campbell, R. R. Taylor, A. Forge, C. R. Hume, Sox2 and JAGGED1 expression in normal and drug-damaged adult mouse inner ear. J Assoc Res Otolaryngol 9, 65 (March, 2008).
36. H. Sakaguchi et al., Spatiotemporal patterns of Musashi1 expression during inner ear development. Neuroreport 15, 997 (Apr. 29, 2004).
37. K. Oshima et al., Differential distribution of stem cells in the auditory and vestibular organs of the inner ear. J Assoc Res Otolaryngol 8, 18 (March, 2007).
38. J. S. Stone, D. A. Cotanche, Hair cell regeneration in the avian auditory epithelium. Int J Dev Biol 51, 633 (2007).
39. M. E. Warchol, Sensory regeneration in the vertebrate inner ear: Differences at the levels of cells and species. Hear Res, (May 19, 2010).
40. J. Cafaro, G. S. Lee, J. S. Stone, Atoh1 expression defines activated progenitors and differentiating hair cells during avian hair cell regeneration. Dev Dyn 236, 156 (January, 2007).
41. N. Daudet et al., Notch regulation of progenitor cell behavior in quiescent and regenerating auditory epithelium of mature birds. Dev Biol, (Nov. 5, 2008).
42. V. Lin et al., Inhibition of Notch activity promotes nonmitotic regeneration of hair cells in the adult mouse utricles. J Neurosci 31, 15329 (Oct. 26, 2011).
43. L. A. Hyde et al., Studies to investigate the in vivo therapeutic window of the gamma-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY411,575) in the CRND8 mouse. J Pharmacol Exp Ther 319, 1133 (December, 2006).
44. G. T. Wong et al., Chronic treatment with the gamma-secretase inhibitor LY-411,575 inhibits beta-amyloid peptide production and alters lymphopoiesis and intestinal cell differentiation. J Biol Chem 279, 12876 (Mar. 26, 2004).
45. B. K. Hadland et al., Gamma-secretase inhibitors repress thymocyte development. Proc Natl Acad Sci USA 98, 7487 (Jun. 19, 2001).
46. M. D. Muzumdar, B. Tasic, K. Miyamichi, L. Li, L. Luo, A global double-fluorescent Cre reporter mouse. Genesis 45, 593 (September, 2007).

47. K. Arnold et al., Sox2(+) adult stem and progenitor cells are important for tissue regeneration and survival of mice. Cell Stem Cell 9, 317 (Oct. 4, 2011).
48. G. W. Harding, B. A. Bohne, J. D. Vos, The effect of an age-related hearing loss gene (Ahl) on noise-induced hearing loss and cochlear damage from low-frequency noise. Hear Res 204, 90 (June, 2005).
49. R. Martinez-Monedero, E. Yi, K. Oshima, E. Glowatzki, A. S. Edge, Differentiation of inner ear stem cells to functional sensory neurons. Dev Neurobiol 68, 669 (April, 2008).
50. A. A. Mikulec, J. J. Hartsock, A. N. Salt, Permeability of the round window membrane is influenced by the composition of applied drug solutions and by common surgical procedures. Otol Neurotol 29, 1020 (October, 2008).
51. S. G. Kujawa, M. C. Liberman, Conditioning-related protection from acoustic injury: effects of chronic deafferentation and sham surgery. J Neurophysiol 78, 3095 (December, 1997).
52. S. F. Maison, R. B. Emeson, J. C. Adams, A. E. Luebke, M. C. Liberman, Loss of alpha CGRP reduces sound-evoked activity in the cochlear nerve. J Neurophysiol 90, 2941 (November, 2003).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cochlear dysfunction by restoring hearing at one or more frequencies in a post-neonatal mammal, the method comprising locally administering to the round window of the ear of the mammal a composition comprising a therapeutically effective amount of a gamma secretase inhibitor.

2. The method of claim 1, wherein the therapeutically effective amount is an amount sufficient to improve hearing as measured by one or more tests selected from whispered speech testing, brain stem auditory evoked response (BAER) testing, auditory brain stem evoked potential (ABEP) testing, Auditory Brainstem Response (ABR) testing, electro-cochleography, or distortion product otoacoustic emissions (DPOAE) test.

3. The method of claim 2, wherein the one or more tests are selected from auditory brain stem evoked potential (ABEP) testing and Auditory Brainstem Response (ABR) testing.

4. The method of claim 1, wherein the composition is administered to the ear within four weeks, two weeks, one week, or one day of an exposure to a physical or chemical ototoxic insult.

5. The method of claim 1, wherein the therapeutically effective amount is an amount sufficient to improve hearing as measured by ABR wave I amplitude.

6. The method of claim 1, wherein the composition further comprises a sustained release carrier.

7. The method of claim 6, wherein the carrier is a polyoxyethylene-polyoxypropylene triblock copolymer.

8. The method of claim 1, wherein the gamma secretase inhibitor is RO4929097 [2,2-dimethyl-N—((S)-6-oxo-6,7-dihydro-5H-dibenzo[b, d]azepin-7-yl)-N'-(2,2,3,3,3-pentafluoro-propyl)-malonamidel; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R)hydroxy-(2R) benzylhexanoyl)-L-leu-L-phe-amide); BMS-708163

(Avagacestat); BMS-299897 (2-[(1R)-1-[[(4-Chlorophenyl)sulfonyl](2,5-difluorophenyl)amino]ethyl-5-fluorobenzenebutanoic acid); MK-0752 (3-(4-((4-chlorophenyl)sulfonyl)-4-(2,5-difluorophenyl)cyclohexyl) propanoic acid); YO-01027 ((S)-2-(2-(3,5-Difluorophenyl)acetamido)-N—((S)-5-methyl-6-oxo-6,7-dihydro-5H-dibenzo[b,d]azepin-7-yl)propanamide; MDL28170 (Sigma; Benzyl N-[(2S)-3-methyl-1-oxo-1-[(1-oxo-3-phenylpropan-2-yl)amino]butan-2-yl]carbamate); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide); ELN-46719 (2-hydroxy-valeric acid amide analog of LY411575; PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide); Compound E ((2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide; and Semagacestat (LY450139; (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide), or pharmaceutically acceptable salts thereof.

9. The method of claim 8, wherein the gamma secretase inhibitor is LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide).

10. The method of claim 1, wherein the mammal is a child, adolescent or adult.

11. The method of claim 1, wherein the mammal is an adult of at least 40 years of age.

12. The method of claim 1, wherein the mammal is a human.

13. A method of treating cochlear dysfunction by restoring hearing at one or more frequencies in a post-neonatal human, the method comprising:
identifying a subject with cochlear dysfunction by one or more tests selected from whispered speech testing, brain stem auditory evoked response (BAER) testing, auditory brain stem evoked potential (ABEP) testing, Auditory Brainstem Response (ABR) testing, electrocochleography, or distortion product otoacoustic emissions (DPOAE) test; and
locally administering to the round window of the ear of the subject a composition comprising a therapeutically effective amount of a gamma secretase inhibitor, wherein the therapeutically effective amount is an amount sufficient to improve hearing as measured by the one or more tests.

14. The method of claim 13, wherein the composition further comprises a sustained release carrier.

15. The method of claim 14, wherein the carrier is a polyoxyethylene-polyoxypropylene triblock copolymer.

16. The method of claim 13, wherein the gamma secretase inhibitor is RO4929097 [2,2-dimethyl-N—((S)-6-oxo-6,7-dihydro-5H-dibenzo[b, d]azepin-7-yl)-N'-(2,2,3,3,3-pentafluoro-propyl)-malonamide]; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); MK-0752 (3-(4-((4-chlorophenyl)sulfonyl)-4-(2,5-difluorophenyl)cyclohexyl) propanoic acid); YO-01027 ((S)-2-(2-(3,5-Difluorophenyl)acetamido)-N—((S)-5-methyl-6-oxo-6,7-dihydro-5H-dibenzo[b,d]azepin-7-yl)propanamide; MDL28170 (Sigma; Benzyl N-[(2S)-3-methyl-1-oxo-1-[(1-oxo-3-phenylpropan-2-yl)amino]butan-2-yl]carbamate); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide); ELN-46719 (2-hydroxy-valeric acid amide analog of LY411575; PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide); Compound E ((2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide; and Semagacestat (LY450139; (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide), or pharmaceutically acceptable salts thereof.

17. The method of claim 16, wherein the gamma secretase inhibitor is LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-l-alaninamide).

18. The method of claim 16, wherein the subject is a child, adolescent or adult.

19. The method of claim 16, wherein the subject is an adult of at least 40 years of age.

20. The method of claim 13, wherein the one or more tests are selected from auditory brain stem evoked potential (ABEP) testing and Auditory Brainstem Response (ABR) testing.

* * * * *

UNITED STATES PATENT AND TRADEMARK OFFICE
CERTIFICATE OF CORRECTION

| | | |
|---|---|---|
| PATENT NO. | : 12,161,647 B2 | Page 1 of 1 |
| APPLICATION NO. | : 17/118111 | |
| DATED | : December 10, 2024 | |
| INVENTOR(S) | : Albert Edge et al. | |

It is certified that error appears in the above-identified patent and that said Letters Patent is hereby corrected as shown below:

In the Claims

In Column 32, Line 62, Claim 8, delete "[b, d]" and insert -- [b,d] --

In Column 32, Line 63, Claim 8, delete "-malonamidel;" and insert -- -malonamide; --

In Column 33, Line 4, Claim 8, delete "sulfony1)" and insert -- sulfonyl) --

In Column 34, Line 7, Claim 16, delete "[b, d]" and insert -- [b,d] --

In Column 34, Line 8, Claim 16, delete "-malonamidel;" and insert -- -malonamide; --

In Column 34, Line 16 (approx.), Claim 16, delete "sulfony1)" and insert -- sulfonyl) --

Signed and Sealed this
Eighteenth Day of March, 2025

Coke Morgan Stewart
*Acting Director of the United States Patent and Trademark Office*

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Genotyping primer LacZ F

<400> SEQUENCE: 1
ttcactggcc gtcgttttac aacgtcgtga                                          30

<210> SEQ ID NO 2
<211> LENGTH: 30
<212> TYPE: DNA
<213> ORGANISM: Artificial Sequence
<220> FEATURE:
<223> OTHER INFORMATION: Genotyping primer LacZ R

<400> SEQUENCE: 2
atgtgagcga gtaacaaccc gtcggattct                                          30

<210> SEQ ID NO 3
<211> LENGTH: 20
<212> TYPE: DNA
<213> ORGANISM: Artificial Sequence
<220> FEATURE:
<223> OTHER INFORMATION: Genotyping primer Cre F

<400> SEQUENCE: 3
tgggcggcat ggtgcaagtt                                                     20

<210> SEQ ID NO 4
<211> LENGTH: 20
<212> TYPE: DNA
<213> ORGANISM: Artificial Sequence
<220> FEATURE:
<223> OTHER INFORMATION: Genotyping primer Cre R

<400> SEQUENCE: 4
cggtgctaac cagcgttttc                                                     20

<210> SEQ ID NO 5
<211> LENGTH: 21
<212> TYPE: DNA
<213> ORGANISM: Artificial Sequence
<220> FEATURE:
<223> OTHER INFORMATION: Genotyping primer oIMR7318 wild-type F
```

```
<400> SEQUENCE: 5
ctctgctgcc tcctggcttc t                                              21

<210> SEQ ID NO 6
<211> LENGTH: 21
<212> TYPE: DNA
<213> ORGANISM: Artificial Sequence
<220> FEATURE:
<223> OTHER INFORMATION: Genotyping primer oIMR7319 wild-type R

<400> SEQUENCE: 6
cgaggcggat cacaagcaat a                                              21

<210> SEQ ID NO 7
<211> LENGTH: 19
<212> TYPE: DNA
<213> ORGANISM: Artificial Sequence
<220> FEATURE:
<223> OTHER INFORMATION: Genotyping primer oIMR7320 mutant R

<400> SEQUENCE: 7
tcaatgggcg ggggtcgtt                                                 19

<210> SEQ ID NO 8
<211> LENGTH: 12
<212> TYPE: PRT
<213> ORGANISM: Artificial Sequence
<220> FEATURE:
<223> OTHER INFORMATION: GSK3beta inhibitor L803

<400> SEQUENCE: 8

Lys Glu Ala Pro Pro Ala Pro Pro Gln Ser Pro Pro
1               5                   10

<210> SEQ ID NO 9
<211> LENGTH: 13
<212> TYPE: PRT
<213> ORGANISM: Artificial Sequence
<220> FEATURE:
<223> OTHER INFORMATION: GSK3beta inhibitor L803-mts

<400> SEQUENCE: 9

Gly Lys Glu Ala Pro Pro Ala Pro Pro Gln Ser Pro Pro
1               5                   10
```